(12) United States Patent
Ban et al.

(10) Patent No.: US 7,622,263 B2
(45) Date of Patent: Nov. 24, 2009

(54) KIT FOR IMMOBILIZING ORGANIC SUBSTANCE, ORGANIC SUBSTANCE-IMMOBILIZED STRUCTURE, AND MANUFACTURING METHODS THEREFOR

(75) Inventors: Kazuhiro Ban, Tokyo (JP); Hidenori Shiotsuka, Ebina (JP); Takeshi Imamura, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 449 days.

(21) Appl. No.: 10/555,383

(22) PCT Filed: Jan. 25, 2005

(86) PCT No.: PCT/JP2005/001316

§ 371 (c)(1),
(2), (4) Date: Nov. 3, 2005

(87) PCT Pub. No.: WO2005/071414

PCT Pub. Date: Aug. 4, 2005

(65) Prior Publication Data

US 2008/0108132 A1      May 8, 2008

(30) Foreign Application Priority Data

Jan. 26, 2004   (JP)   ............................. 2004-016858

(51) Int. Cl.
  *G01N 33/53*  (2006.01)
  *G01N 33/00*  (2006.01)
  *C07K 5/00*   (2006.01)

(52) U.S. Cl. ........................... 435/7.1; 436/86; 530/327

(58) Field of Classification Search .................. 435/7.1; 436/86; 530/327
See application file for complete search history.

(56) References Cited

U.S. PATENT DOCUMENTS

| | | | |
|---|---|---|---|
| 5,665,597 A | 9/1997 | Imamura et al. | 435/253.3 |
| 5,679,568 A | 10/1997 | Imamura et al. | 435/262.5 |
| 5,693,527 A | 12/1997 | Imamura | 435/262 |
| 5,803,664 A | 9/1998 | Kawabata et al. | 405/128 |
| 5,807,736 A | 9/1998 | Kozaki et al. | 435/262.5 |
| 5,854,059 A | 12/1998 | Kozaki et al. | 435/262 |
| 5,863,789 A | 1/1999 | Komatsu et al. | 435/262 |
| 5,945,331 A | 8/1999 | Kozaki et al. | 435/262 |
| 5,962,305 A | 10/1999 | Mihara et al. | 435/262.5 |
| 5,993,658 A | 11/1999 | Kato et al. | 210/611 |
| 6,004,772 A | 12/1999 | Imamura et al. | 435/34 |
| 6,017,746 A | 1/2000 | Imamura et al. | 435/252.1 |
| 6,096,530 A | 8/2000 | Kato et al. | 435/253.3 |
| 6,225,131 B1 | 5/2001 | van Damme et al. | 436/524 |
| 6,319,706 B1 | 11/2001 | Kawaguchi et al. | 435/293.1 |
| 6,472,191 B1 | 10/2002 | Yano et al. | 435/189 |
| 6,479,621 B2 | 11/2002 | Honma et al. | 528/361 |
| 6,586,562 B2 | 7/2003 | Honma et al. | 528/361 |
| 6,649,381 B1 | 11/2003 | Honma et al. | 435/135 |
| 6,660,516 B1 | 12/2003 | Imamura et al. | 435/252.8 |
| 6,686,439 B2 | 2/2004 | Kenmoku et al. | 528/272 |
| 6,803,444 B2 | 10/2004 | Suzuki et al. | 528/361 |
| 6,808,854 B2 | 10/2004 | Imamura et al. | 430/110 |
| 6,828,074 B2 | 12/2004 | Yano et al. | 430/109.1 |
| 6,855,472 B2 | 2/2005 | Imamura et al. | 430/109.4 |
| 6,858,367 B2 | 2/2005 | Yano et al. | 430/109 |
| 6,858,417 B2 | 2/2005 | Yano et al. | 435/189 |
| 6,861,496 B2 | 3/2005 | Kenmoku et al. | 528/272 |
| 6,861,550 B2 | 3/2005 | Honma et al. | 560/53 |
| 6,864,074 B2 | 3/2005 | Yano et al. | 435/189 |
| 6,867,023 B2 | 3/2005 | Honma et al. | 435/135 |
| 6,869,782 B2 | 3/2005 | Kenmoku et al. | 435/130 |
| 6,908,720 B2 | 6/2005 | Kenmoku et al. | 430/97 |
| 2002/0106702 A1* | 8/2002 | Wagner et al. | 435/7.9 |
| 2003/0104302 A1 | 6/2003 | Honma et al. | 430/110.2 |
| 2003/0118931 A1 | 6/2003 | Yano et al. | 430/108.22 |
| 2003/0170716 A1 | 9/2003 | Yano et al. | 435/6 |
| 2004/0067576 A1 | 4/2004 | Honma et al. | 435/252.34 |
| 2004/0259026 A1 | 12/2004 | Honma et al. | 430/270.1 |

(Continued)

FOREIGN PATENT DOCUMENTS

EP   1 253 160 A2   10/2002

(Continued)

OTHER PUBLICATIONS

Coletti-Previero Anal. Biochem. 180:1-10; 1989.*

(Continued)

*Primary Examiner*—Fereydoun G Sajjadi
(74) *Attorney, Agent, or Firm*—Fitzpatrick, Cella, Harper & Scinto

(57) ABSTRACT

To provide an organic substance-immobilized structure employing a novel immobilizing technique and a manufacturing method thereof using the novel immobilizing technique, where, when an organic substance, particularly a biological substance is immobilized on the surface of a substrate, the organic substance, particularly the biological substance can be stably immobilized on the surface of the substrate through orientation of the organic substance, particularly the biological substance suitable for exerting physiological functions thereof. At least part of the substrate's surface is constructed of one or more substrates containing aluminum oxide. The immobilization of the organic substance to the surface of the substrate is carried out by binding at least part of the binding domain to the surface of the substrate through a binding domain containing a peptide having an affinity to aluminum oxide and composed of at least one or more amino acids, which is coupled with the organic substance.

1 Claim, 3 Drawing Sheets

U.S. PATENT DOCUMENTS

2006/0115861 A1     6/2006     Shiotsuka et al. ............ 435/7.9
2006/0183235 A1     8/2006     Hashimoto et al. ............ 436/86

FOREIGN PATENT DOCUMENTS

JP            6-3317         1/1994
WO       2005/016971 A1     2/2005

OTHER PUBLICATIONS

Coletti-Previero et al. Anal. Biochem. 180:1-10, 1989.*

Andrew Bradbury, et al., "Use of Living Columns to Select Specific Phage Antibodies", Bio/Technology, vol. 11, Dec. 1993, pp. 1565-1569.

Alain Charbit, et al., "Versatility of a vector for expressing foreign polypeptides at the surface of Gram-negative bacteria", Gene, vol. 70, 1988, pp. 181-189.

Steven E. Cwirla, et al., "Peptides on phage: A vast library of peptides for identifying ligands", Proceedings of the National Academy of Sciences, vol. 87, Aug. 1990, pp. 6378-6382.

Joseph A. Francisco, et al., "Production and fluorescence-activated cell sorting of *Escherichia coli* expressing a functional antibody fragment on the external surface", Proceedings of the National Academy of Sciences, vol. 90, Nov. 1993, pp. 10444-10448.

Patrick Fuchs, et al., "Targeting Recombinant Antibodies to the Surface of *Escherichia coli*: Fusion to a Peptidoglycan Associated Lipoprotein", Bio/Technology, vol. 9, Dec. 1991, pp. 1369-1372.

Lisbeth Hedegaard, et al., "Type 1 fimbriae of *Escherichia coli* as carriers of heterologous antigenic sequences", Gene, vol. 85, 1989, pp. 115-124.

A. Nyamsi Hendji, et al., "Covalent immobilization of glucose oxidase on silanized platinum microelectrode for the monitoring of glucose", Sensors and Actuators B, vols. 15-16, 1993, pp. 127-134.

Maurice Hofnung, "Expression of Foreign Polypeptides at the *Escherichia coli* Cell Surface", Method in Cell Biology, vol. 34, 1991, pp. 77-105.

Thomas Klauser, et al., "Extracellular transport of cholera toxin B subunit using *Neisseria* IgA protease β-domain: conformation-dependent outer membrane translocation", EMBO Journal, vol. 9, 1990, pp. 1991-1999.

S. Pistor, et al., "Expression of Viral Hemagglutinin on the Surface of *E. coli*", Klin Wochenschr, vol. 66, 1988, pp. 110-116.

J. Sambrook, et al., Molecular Cloning, A Laboratory Manual, Second Edition, Cold Spring Harbor Laboratory Press, 1989, p. 5.72.

Jamie K. Scott, et al., "Searching for Peptide Ligands with an Epitope Library", Science, vol. 249, 1990, pp. 386-390.

M-A. Coletti-Previero et al., "Alumina-Phosphate Complexes for Immobilization of Biomolecules," 180 *Anal. Biochem.* 1-10 (1989).

Shirley Furtado et al., "Biocatalyst-Adsorbant Systems: A Viable Alternative to Proteolytic Processes in Solution," 32(3) *Prep. Biochem. Biotechnol.* 217-37 (2002).

* cited by examiner

KIT FOR IMMOBILIZING ORGANIC SUBSTANCE, ORGANIC SUBSTANCE-IMMOBILIZED STRUCTURE, AND MANUFACTURING METHODS THEREFOR

TECHNICAL FIELD

The present invention relates to an organic substance-immobilized substrate prepared by immobilizing an organic substance on a substrate's surface at least part of which has an aluminum oxide layer and to a method of manufacturing the same, and further relates to a peptide having an affinity to a layer containing aluminum oxide and used for immobilization of the organic substance and to a DNA that encodes the peptide having the affinity. More particularly, the present invention relates to a biological substance-immobilized substrate which is applicable to a target substance-detecting element, a target substance-converting element, a target substance-separating element, and a protein structure-optimizing element by the utilization of a biological substance immobilized on the substrate, and to a manufacturing method therefor.

BACKGROUND ART

Many studies and developments have been conducted for a wide range of applications of so-called biosensors and bioreactors that utilize molecular recognition ability and substance-converting ability of biological substances such as enzymes and antibodies as well as nucleic acid molecules (e.g., DNA and RNA) including genes.

For the biosensors, there are growing demands on further technical developments for applications on various detection targets in conjunction with growing interests in health as well as matters of environmental pollutants and public safety thereof. Recently, furthermore, the bioreactors have attracted much attention as eco-friendly clean processing technologies. Therefore, for example, there are increasing demands on further technical developments such as those in processes of producing products utilizing various bioprocesses.

For the biosensors, specifically, detectors for detecting objective ones by utilizing the selective molecular recognition of respective biological substance molecules have been developed extensively. For example, detectors developed on the basis of various kinds of detection procedures include a DNA sensor chip that utilizes a base-sequence-dependent complimentary hydrogen bonding between deoxyribonucleic acid (hereinafter, referred to as DNA) sequences (i.e., a hybridization reaction between the complimentary strands), an antibody sensor that detects a disease marker or the like to be eluted in blood, by utilizing a molecular recognition ability, originated from a specific binding ability between a protein molecule and a low-molecular substance or between protein molecules such as an antigen-antibody reaction, and an enzyme sensor for detecting the level of a substrate substance by utilizing an oxidation-reduction enzyme or a hydrolytic enzyme, as typified by a glucose sensor for a diabetic patient.

Currently, the biosensor that makes use of any of these biological substances, generally employs a system of using, in the form of a biological substance-immobilized substrate, a biological substance to be used, for example a nucleic acid molecule such as DNA, or proteins of antibodies, enzymes, etc., which is immobilized on the surface of a substrate such as a flat plate, a sphere or a materials, or the like.

In addition, one of the performance qualities required for the biosensors being developed nowadays is "high sensitivity and downsizing", which is typified by μ-TAS. For attaining an object of "high sensitivity and downsizing", an important technical issue is how to effectively utilize a minute space of a reaction field or detection field and how to increase the sensitivity of the biosensor.

For instance, in the detection field where the biological substance is immobilized on the substrate, in addition to the specific binding to a target substance to be detected, there is a possibility of causing much non-specific adsorption of biological substances except the substance to be detected or a possibility of causing a non-specific binding of the substance to be detected itself on the substrate. These non-specific adsorbing phenomena will become one of the factors that decrease a Signal/Noise ratio of the biosensor. In particular, the total amount of the specific binding of the target substance to be detected falls off as the detection field decreases. Therefore, the biosensor tends to be influenced by noises due to the non-specific adsorption, resulting in difficulty in high sensitive measurement. Also, in terms of an effective utilization of a sample in minute amounts, it is difficult to carry out measurement at a sufficiently high accuracy when the non-specific adsorption of the target substance to be detected is caused in large quantities. Hereafter, therefore, an important technical problem which remains to be improved is to reduce or prevent the non-specific adsorption phenomenon.

On the other hand, for the bioreactors, there have developed procedures for producing food additives such as amino acids, candidate substances for medicines and antibiotics by enzymatic reactions that mainly employ the position-selective catalytic functions of enzymes as one type of proteins instead of procedures that utilize microorganisms having the abilities of producing objective products. Besides, the applications of enzymatic reactions to the productions of chemicals and polymer materials have been also under study. In the development of bioreactors using such enzymatic reactions, because the development of devices suitable for high-mix low-volume production has been also mainstream, for example, with the spread of a technique for screening a candidate substance by means of combinatorial chemistry, there are increasing demands for miniaturizing individual biosensors by means of a device on which an enzyme to be used in a reaction just as in the case with the biosensor described above is immobilized (i.e., for high-mix low-volume production).

In addition, materials, which can be employed for substrates, flat plates, spheres and porous materials, or the like, for biological substance-immobilized substrates to be used in the biosensors and bioreactors, generally include organic polymers, glass, ceramics, metal flat plates, and other materials known in the art, depending on the types and applications of the biological substances.

As a method of immobilizing a biological substance such as protein, on the surface of substrate, for example, there is an immobilizing procedure using physical adsorption, which includes the steps of forming a coating layer of a protein solution on the surface of a substrate by using means for dipping the substrate into the protein solution or applying the protein solution thereon, and then removing a solvent from the coating layer and drying it to allow the protein to be immobilized on the surface of the substrate as a result of physical adsorption. Alternatively, there is another procedure that includes next two steps, the first step is chemically modifying the surfaces of a substrate or the protein molecules to provide the high activity functional groups, and second step is immobilization of the protein molecules on the surface of the substrate through the chemical bonding by forming of chemical bonding between the introduced the high activity functional groups and other functional groups. These procedures have been hitherto known as those for immobilizing biological substances on the surfaces of substrate. As an example of the immobilizing method using physical adsorption, JP 06-003317 A discloses a method of manufacturing an enzymatic electrode by the application of a method including the steps of forming a charge-transporting organic complex layer on the surface of a conductive substrate and then applying a protein solution on the charge-transporting organic complex layer, followed by drying the protein layer to allow an enzyme protein to be physically adsorbed and immobilized on the surface of the substrate through the charge-transporting organic complex layer.

As an example of the immobilizing method using the chemical bonding, Sensor and Actuators B15-16 p 127 (1993) discloses a method including the steps of subjecting a platinum-deposited surface of a silicon substrate to treatment with an amine-based silane coupling agent and then coupling between an amino group derived from the amino-silane coupling and a peptide chain by means of a cross-linking agent such as glutaric aldehyde to carry out immobilization. In addition, for making a detector such as a biosensor-composed of antibodies immobilized on a glass substrate, a method is applied, in which reactive functional groups are introduced to the surface of the glass substrate by means of treatment with a silane coupling agent and a peptide chain is immobilized through a chemical bonding using a cross-lining agent as described above.

However, in the immobilizing method based on physical adsorption or the chemically-immobilizing method based on chemical cross-linking, the portion of a protein, which is used for adsorption or binding to the substrate can be selected at random. Therefore, when a portion, which directly or indirectly relates to the binding ability required for the protein, the enzymatic activity of the protein, or the like, also becomes one relating to the binding to the surface of a substrate, there is a fear that a desired function of the protein will deteriorate remarkably if the protein binds to the substrate.

Therefore, it becomes important to develop means for previously determining an immobilizing portion of a molecule to be immobilized, which will be used for binding to the surface of the substrate, for example, a technology capable of previously controlling the orientation of a biological substance to be immobilized on the surface of the substrate.

Furthermore, for attaining "high sensitivity and downsizing", the biological substance should be integrated very densely in a very small area on the surface of the substrate and then immobilized thereon.

As an example of a method of integrating the biological substance very densely and immobilizing the same, there is a method well known in the art, where a substrate having a large specific surface area, for example a porous material having a regular nanoporous structure, is adopted as a substrate, and a biological substance is then immobilized on the surface having a porous structure with a large specific surface area. As a conventional method for forming the porous structure having regularity with a scale in the order of nanometers, which can be used for the above purpose, a polymer membrane filter, porous glass, anodized aluminum oxide film, and so on are well known in the art. For the anodized aluminum oxide film, in particular, the pore size thereof can be regulated by means of a voltage applied at the time of oxidation to make a film having a given pore size in the order of nanometers.

Making the porous material into the substrate enables a reaction field on which a biological substance is immobilized in an amount enough for high-sensitivity detection even in a very small area.

Conventional examples of the method using the porous substrate described above as a substrate, particularly the method by which a biological substance such as a protein is immobilized on an anodized aluminum oxide film, include the following procedures:

As an example of a procedure for covalently binding a protein using a cross-linking agent after surface treatment with an amino-silane coupling agent, U.S. Pat. No. 6,225,131 discloses a method including the steps of providing a commercially-available aluminum oxide film as a substrate, subjecting the surface thereof to treatment with 3-aminopropyl-triethoxysilane (APS), and covalently binding anti-human chorionic gonadotropin mouse monoclonal antibodies using glutaric aldehyde as a cross-linking agent to immobilize them on the surface of the substrate.

Furthermore, as an example of a procedure using intermolecular binding between an organic substance and a peptide, US 2002/0106702 A1 discloses a method by which an organic thin film for binding a protein is arranged on an aluminum oxide film to immobilize a protein fused with a peptide chain having affinity to an organic substrate that constitutes an organic thin film described above.

The above substrate having a large specific surface area, such as a porous material having a regular nanoporous structure, is adopted as a substrate to allow a larger amount of the biological substance to be immobilized on the surface of the substrate. However, when the biological substance immobilized on the substrate does not take an orientation suitable for the binding to a target substance to be detected, the detection sensitivity corresponding to the amount of the biological substance immobilized may not be attained. Also, when a biological substance does not have an orientation suitable for the substrate substance on which the biological substance acts, the reactivity corresponding to an amount of the biological substance to be immobilized is not attained in some cases. That is, unless a biological substance to be immobilized on a substrate is immobilized after controlling the orientation suitable for the use thereof, the biological substance will be insufficient to exert its advantage accompanying immobilization of a larger amount of the biological substance on the surface of the substrate through the use of a substrate having a large specific surface area.

In other words, unless a biological substance to be immobilized on a substrate is immobilized after controlling the orientation suitable for the use thereof, it becomes necessary to further increase the amount of the biological substance to be immobilized on the substrate to obtain the desired detection sensitivity or reactivity. Thus, there is a possibility that an excess amount of the biological substance per unit area of the substrate should be immobilized or the area of the substrate on which the biological substance is immobilized should be excessively extended. When the area of the substrate on which the biological substance is immobilized is extended excessively, it may become a large obstacle to the downsizing of a device itself.

Furthermore, in the case of ingredients in the biological substance, which will cost high upon their preparation, there is a possibility of increasing the total cost of the device when they will be used in large amounts. Furthermore, a procedure of forming an additional adhesion layer for binding an organic substance to a substrate (i.e., a layer formed between the substrate and the organic substance and having a configuration different from that of the organic substance to be immobilized) may involve an increase in the number of steps required and become a large obstacle to a decrease in device cost.

In addition, a high technical level is also required for completely forming the adhesion layer on the inner-wall surface of the porous portion of the nanoporous structure. If the formation of the adhesion layer in the inside of the pore is insufficient, an effect obtained by increasing the specific surface area by means of the porous structure may be insufficiently exerted.

In view of the present situation, such a problem cannot be coped with any publicly known technology of immobilizing ingredients in the biological substance by means of chemical bonding between the ingredients and the substrate with physical adsorption through the adhesion layer or non-specific modification using a cross-linking agent.

Therefore, it has been desired to provide a structure composed of a substrate and an organic substance immobilized on the surface of the substrate such that the molecular orientation of the organic substance is regulated so as to exert its desired functions, and a concise immobilizing procedure that allows the organic substance to be immobilized on the surface of the substrate.

DISCLOSURE OF THE INVENTION

An object of the present invention is to provide an organic substance-immobilized structure that adopts novel immobilizing means that enables stable immobilization of an organic substance used for a biosensor or bioreactor on the surface of a substrate with orientation suitable for exerting physiological functions of the organic substance, especially, biological substance when the organic substance, particularly the biological substance, is immobilized on the surface of the substrate, and a manufacturing method utilizing the novel immobilizing means. In addition, another object of the present invention is to provide a peptide having an affinity to an aluminum oxide-containing layer which is available as the novel immobilizing means and a DNA that encodes the peptide, and an expression vector for providing a fused product of the organic substance and a binding domain containing the peptide having the affinity to aluminum oxide. In addition, still another object of the present invention is to provide a fused product of an organic substance and a binding domain.

For attaining the above objects, the inventors of the present invention have made studies on novel immobilizing means which is available when an organic substance, especially biological substance is immobilized on the surface of a substrate and found that the organic substance may be stably immobilized on the surface of a substrate with an orientation suitable for exerting physiological functions of the organic substance, particularly the biological substance, when a portion used for immobilization is arranged separately from a main portion of the organic substance, and a procedure utilizing a physical interaction specific to the portion to be utilized in immobilization instead of a procedure utilizing a chemical reagent, is chosen for binding to the surface of the substrate in the portion utilized in immobilization in order to allow an immobilized organic substance, particularly a biological substance, to exert sufficiently original physiological functions.

In the procedure that utilizes the physical interaction specific to the portion utilized for immobilization, a peptide having an affinity to aluminum oxide can be selected when a substrate containing aluminum oxide is used as a material of the surface to be immobilized. It was confirmed that an organic substance, particularly a biological substance, may be immobilized on the substrate having the surface made of an aluminum-oxide-containing material through a physical interaction between the aluminum oxide on the surface and the binding domain having an affinity to the aluminum oxide with high reproducibility and stability while keeping its orientation suitable for exerting physiological functions thereof when a binding domain containing the peptide having the affinity to aluminum oxide is in the form of a fused product coupled with a functional domain made of the organic substance, particularly the biological substance.

The present invention has been completed on the basis of those findings.

That is, according to the present invention, an organic substance-immobilized structure includes:

a substrate having an organic substance immobilized on a surface thereof and the surface at least part of which contains aluminum oxide; and a binding domain for immobilizing the organic substance on the substrate, having an ability to bind to the aluminum oxide and being coupled with the organic substance, wherein:

the binding domain contains at least a peptide composed of one or more amino acids; and the organic substance is immobilized on the surface of the substrate through the binding domain by means of specific binding of the peptide to the aluminum oxide.

In the organic substance-immobilized structure according to the present invention, a capture molecule for capturing a target substance can be used as the organic substance. Alternatively, as the organic substance, a molecule having a function to convert the substance can be used.

In addition, the present invention also provides a method of manufacturing the organic substance-immobilized structure. That is, the method of manufacturing the organic substance-immobilized structure according to the present invention is a method of manufacturing a structure having an organic substance immobilized on a substrate, including the steps of:

preparing an organic substance-binding domain fused product composed of the substrate having a surface at least part of which contains aluminum oxide and a binding domain, having an ability to bind to the aluminum oxide and coupled with the organic substance; and immobilizing the organic substance on the surface of the substrate by bringing the fused product into contact with the surface of the substrate to cause a peptide having an ability to bind to the aluminum oxide to specifically bind to the aluminum oxide.

In this case, the organic substance may be a biological substance containing a protein. The method may further include the step of obtaining the organic substance-binding domain fused product by inducing expression of a fused product-type protein formed by coupling a peptide portion included in the binding domain with the protein included in the biological substance on the basis of a coupling gene having a sequence of bases coupled with each other so as to encode a combination of an amino acid sequence of the protein and an amino acid sequence included in the binding domain which are coupled.

On the other hand, a peptide having an ability to bind to aluminum oxide, which is a feature of the organic substance-immobilized structure of the present invention, is a peptide, which has any one of at least one amino acid sequence selected from the group consisting of amino acid sequences of SEQ ID NOS: 1 to 32, an altered amino acid sequence obtained such that the amino acid sequence is subjected to a deletion, substitution, or addition of one or more amino acids, and a complex amino acid sequence containing two or more of these amino acid sequences, and a repetitive sequence of the amino acid sequences, the amino acid sequence including a peptide having an affinity to aluminum oxide.

```
                                          (SEQ ID NO: 1)
Val-Tyr-Ala-Asn-Gln-Thr-Pro-Pro-Ser-Lys-Ala-Arg (SEQ ID NO: 2)
Gln-Ser-Ser-Ile-Thr-Thr-Arg-Asn-Pro-Phe-Met-Thr (SEQ ID NO: 3)
Phe-Met-Asn-His-His-Pro-Asn-Ser-Gln-Gln-Tyr-His (SEQ ID NO: 4)
Gln-Tyr-Thr-Ser-Ser-Gly-Ile-Ile-Thr-Ser-Ser-Ala (SEQ ID NO: 5)
His-His-His-Pro-Glu-Asn-Leu-Asp-Ser-Thr-Phe-Gln (SEQ ID NO: 6)
Gln-Pro-His-Met-His-Arg-Ser-Ser-His-Gln-Asp-Gly (SEQ ID NO: 7)
Asn-Thr-Thr-Met-Gly-Pro-Met-Ser-Pro-His-Ser-Gln (SEQ ID NO: 8)
Ala-Ala-His-Phe-Glu-Pro-Gln-Thr-Met-Pro-Met-Ile (SEQ ID NO: 9)
Asp-His-Gln-Leu-His-Arg-Pro-Pro-His-Met-Met-Arg (SEQ ID NO: 10)
Val-Ser-Arg-His-Gln-Ser-Trp-His-Pro-His-Asp-Leu (SEQ ID NO: 11)
Met-Met-Gln-Arg-Asp-His-His-Gln-His-Asn-Ala-Gln (SEQ ID NO: 12)
Val-Thr-Leu-His-Thr-Val-Asp-His-Ala-Pro-Gln-Asp (SEQ ID NO: 13)
Ser-Val-Ser-Val-Gly-Met-Lys-Pro-Ser-Pro-Arg-Pro (SEQ ID NO: 14)
His-Leu-Gln-Ser-Met-Lys-Pro-Arg-Thr-His-Val-Leu (SEQ ID NO: 15)
Ile-Pro-Asn-Ala-Glu-Thr-Leu-Arg-Gln-Pro-Ala-Arg (SEQ ID NO: 16)
Val-Gly-Val-Ile-Ser-Ser-Trp-His-Pro-His-Asp-Leu (SEQ ID NO: 17)
Thr-Val-Pro-Ile-Tyr-Asn-Thr-Gly-Ile-Leu-Pro-Thr (SEQ ID NO: 18)
Tyr-Thr-Met-His-His-Gly-Ser-Thr-Phe-Met-Arg-Arg (SEQ ID NO: 19)
Ser-Met-Met-His-Val-Asn-Ile-Arg-Leu-Gly-Ile-Leu (SEQ ID NO: 20)
Ala-Pro-Met-His-His-Met-Lys-Ser-Leu-Tyr-Arg-Ala (SEQ ID NO: 21)
Met-Met-Gln-Arg-Asp-His-His-Gln-His-Met-Arg-Arg (SEQ ID NO: 22)
Met-Lys-Thr-His-His-Gly-Asn-Asn-Ala-Val-Phe-Leu (SEQ ID NO: 23)
Leu-Glu-Pro-Leu-Pro-His-Thr-Pro-Arg-Met-Tyr-Ala (SEQ ID NO: 24)
Gln-Leu-Tyr-Glu-Pro-Asp-Ser-Gly-Pro-Trp-Ala-Pro (SEQ ID NO: 25)
Trp-Met-Thr-Lys-Met-Pro-Thr-Thr-His-Thr-Arg-Tyr (SEQ ID NO: 26)
His-His-Pro-Met-Tyr-Ser-Met-Thr-Arg-Ala-Leu-Pro (SEQ ID NO: 27)
Gly-Ser-Ala-His-Ser-Arg-Asn-Asp-Ala-Ala-Pro-Val (SEQ ID NO: 28)
His-Ser-Pro-Leu-Met-Gln-Tyr-His-Met-Ser-Gly-Thr (SEQ ID NO: 29)
Thr-Ala-His-Met-Thr-Met-Pro-Ser-Arg-Phe-Leu-Pro (SEQ ID NO: 30)
Ala-Cys-Pro-Pro-Thr-Gln-Ser-Arg-Tyr-Cys (SEQ ID NO: 31)
Ala-Cys-Asn-Gly-Met-Leu-Ala-Phe-Gln-Cys (SEQ ID NO: 32)
Ala-Cys-Thr-Pro-Lys-Pro-Gly-Lys-His-Cys
```

In addition, the present invention provides a DNA molecule to be used in making a peptide chain having an ability to bind to the aluminum oxide as a part of a fused product-type protein in the method of manufacturing the organic substance-immobilized structure.

In other words, the DNA molecule that encodes the peptide chain having the ability to bind to aluminum oxide according to the present invention is a DNA molecule, which encodes a peptide chain, the peptide chain having any one of at least one amino acid sequence selected from the group consisting of amino acid sequences of SEQ ID NOS: 1 to 32, an altered amino acid sequence obtained such that the amino acid sequence is subjected to a deletion, substitution, or addition of one or more amino acids, and a complex amino acid sequence containing two or more of the amino acid sequences, and a repetitive sequence of any of the amino acid sequences, the amino acid sequence having an affinity to aluminum oxide.

In addition, the present invention also provides an expression vector to be used for expression of a fused product-type protein that includes a peptide chain having an ability to bind to the aluminum oxide in the method of manufacturing the organic substance-immobilized structure. That is, the expression vector according to the present invention includes a coupling gene, wherein the coupling gene can induce expression of a fused product-type protein formed by coupling a peptide portion included in a binding domain with a protein included in an organic substance in a host cell with respect to an organic substance-binding domain fused product composed of:

the organic substance containing a protein in at least part thereof; and the binding domain coupled with the organic substance, containing at least a peptide having an affinity to aluminum oxide and made of one or more amino acids and having an ability to bind to the aluminum oxide, with the peptide having the affinity to the aluminum oxide containing any one of at least one amino acid sequence selected from the group consisting of amino acid sequences of SEQ ID NOS: 1 to 32, an altered amino acid sequence obtained such that the amino acid sequence is subjected to a deletion, substitution, and addition of one or several amino acids, or a complex amino acid sequence containing two or more of the amino acid sequences, and a repetitive sequence of the amino acid sequences, on the basis of a coupling gene having a sequence of bases being coupled with each other to encode a combination of an amino acid sequence of the protein and an amino acid sequence included in the binding domain, which constitute the organic substance-binding domain fused product.

Therefore, the expression vector according to the present invention can be provided as an expression vector made by inserting DNA by which at least amino acid sequence of a fused product-type protein among peptide chains that constitute the organic substance-binding domain fused product into various vectors, for example plasmids, phagemids, and cosmids, to be used in molecular biological procedures such as transformation of host cells by transferring genes into the host cells and expression of proteins.

Furthermore, the present invention also provides a kit for manufacturing an organic substance-immobilized structure exclusively used for the manufacture of the organic substance-immobilized structure according to the present invention. That is, the kit for manufacturing the organic substance-immobilized structure according to the present invention is a kit for immobilizing an organic substance on a substrate, including:

a substrate having a surface at least part of which contains aluminum oxide; and a binding domain for immobilizing the organic substance on the substrate, having an ability to bind to the aluminum oxide and being coupled with the organic substance, wherein:

the binding domain contains at least a peptide composed of one or more amino acids; and the organic substance is immobilized on the substrate by means of specific binding of the peptide to the aluminum oxide when the substrate and the binding domain are brought into contact with each other.

In addition, an organic substance-binding domain fused product contains an organic substance and a binding domain having an ability to bind to aluminum oxide, wherein the binding domain contains at least a peptide composed of one or more amino acids, and the peptide contains any one of at least one amino acid sequence selected from the group consisting of amino acid sequences of SEQ ID NOS: 1 to 32, an altered amino acid sequence obtained such that the amino acid sequence is subjected to a deletion, substitution, or addition of one or several amino acids, and a complex amino acid sequence containing two or more of the amino acid sequences, and a repetitive sequence of the amino acid sequences.

Furthermore, in the organic substance-immobilized structure according to the present invention, for example a substrate on which an organic substance is immobilized, an aluminum oxide layer is formed to form a surface of the substrate on which the organic substance is to be immobilized, while the organic substance to be immobilized is provided itself as a functional domain and is constructed such that a binding domain formed of a peptide constructed of one or more amino acids having an ability to bind to the aluminum oxide layer is coupled with the functional domain. Thus, the organic substance provided as the functional domain is allowed to be selectively immobilized on the surface of the substrate through the ability of the binding domain coupled to bind to aluminum oxide without directly contacting the surface of the substrate. The organic substance is immobilized on the surface of the substrate through the binding domain formed independently, so that the functions inherent in the organic substance will not be influenced by immobilization and also any chemical reagent is not used in the immobilization. Therefore, the organic substance is not subjected to a chemical reaction that affects the desired function of the organic substance.

In the organic substance-immobilized structure according to the present invention, an amino acid sequence of a peptide included in the binding domain is appropriately selected from peptides having an affinity to the aluminum oxide of the present invention. Thus, a fused product can be provided as one having the functions of the organic substance, particularly the biological substance, as an immobilization target, which are comparable with the inherent functional levels at all, allowing the organic substance to be used for various immobilization target organic substrates. Besides, the functions of the organic substance to be immobilized are selected and used, so the organic substance-immobilized structure of the present invention can be applied to a more excellent target substance-capturing element, target substance-converting element, target substance-separating element, and protein structure-optimizing element.

BEST MODE FOR CARRYING OUT THE INVENTION

Figure 1:
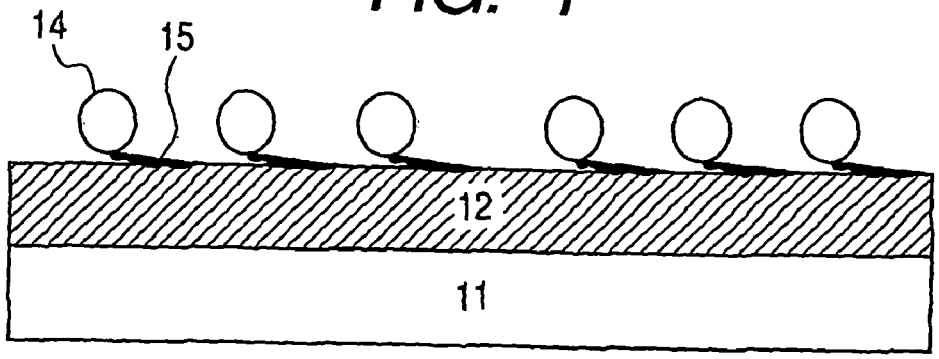
FIG. 1 is a cross sectional diagram schematically showing a configuration of a structure of an example of an organic substance-immobilized structure according to the present invention.

The organic substance-immobilized structure of the present invention is a structure where an organic substance is immobilized on the surface of the substrate, characterized by including: a substrate having a surface at least part of which contains aluminum oxide; and an organic substance being immobilized on the surface of the substrate through a binding domain containing a peptide composed of at least one or more amino acids. In particular, the peptide included in the binding domain is characterized by containing an amino acid sequence having an ability to bind to the aluminum oxide.

On the other hand, the organic substance may include a biological substance and the biological substance may include a protein or a part thereof. At this time, in a coupling portion between the biological substance and the binding domain, a linker composed of one or more amino acids may be included between a peptide containing an amino acid sequence having an ability to bind to the aluminum oxide in the binding domain and the biological substance.

The peptide, which contains the amino acid sequence having the ability to bind to the aluminum oxide in the binding domain, is a peptide containing the whole of at least one amino acid sequence selected from the group consisting of SEQ ID NOS: 1 to 32 described below, or an amino acid sequence having a part thereof, or a peptide having a repetitive structure of any of these amino acid sequences, or a peptide containing a complex composed of these amino acid sequences, and alternatively the peptide may contain one or more sequences of the amino acid sequences of SEQ ID NOS: 30 to 32 and may form a cyclic structure with an intramolecular disulfide binding in the sequence.

(SEQ ID NO: 1)
Val-Tyr-Ala-Asn-Gln-Thr-Pro-Pro-Ser-Lys-Ala-Arg (SEQ ID NO: 2)
Gln-Ser-Ser-Ile-Thr-Thr-Arg-Asn-Pro-Phe-Met-Thr (SEQ ID NO: 3)
Phe-Met-Asn-His-His-Pro-Asn-Ser-Gln-Gln-Tyr-His (SEQ ID NO: 4)
Gln-Tyr-Thr-Ser-Ser-Gly-Ile-Ile-Thr-Ser-Ser-Ala (SEQ ID NO: 5)
His-His-His-Pro-Glu-Asn-Leu-Asp-Ser-Thr-Phe-Gln (SEQ ID NO: 6)
Gln-Pro-His-Met-His-Arg-Ser-Ser-His-Gln-Asp-Gly (SEQ ID NO: 7)
Asn-Thr-Thr-Met-Gly-Pro-Met-Ser-Pro-His-Ser-Gln (SEQ ID NO: 8)
Ala-Ala-His-Phe-Glu-Pro-Gln-Thr-Met-Pro-Met-Ile (SEQ ID NO: 9)
Asp-His-Gln-Leu-His-Arg-Pro-Pro-His-Met-Met-Arg (SEQ ID NO: 10)
Val-Ser-Arg-His-Gln-Ser-Trp-His-Pro-His-Asp-Leu (SEQ ID NO: 11)
Met-Met-Gln-Arg-Asp-His-His-Gln-His-Asn-Ala-Gln (SEQ ID NO: 12)
Val-Thr-Leu-His-Thr-Val-Asp-His-Ala-Pro-Gln-Asp (SEQ ID NO: 13)
Ser-Val-Ser-Val-Gly-Met-Lys-Pro-Ser-Pro-Arg-Pro (SEQ ID NO: 14)
His-Leu-Gln-Ser-Met-Lys-Pro-Arg-Thr-His-Val-Leu (SEQ ID NO: 15)
Ile-Pro-Asn-Ala-Glu-Thr-Leu-Arg-Gln-Pro-Ala-Arg (SEQ ID NO: 16)
Val-Gly-Val-Ile-Ser-Ser-Trp-His-Pro-His-Asp-Leu (SEQ ID NO: 17)
Thr-Val-Pro-Ile-Tyr-Asn-Thr-Gly-Ile-Leu-Pro-Thr (SEQ ID NO: 18)
Tyr-Thr-Met-His-His-Gly-Ser-Thr-Phe-Met-Arg-Arg (SEQ ID NO: 19)
Ser-Met-Met-His-Val-Asn-Ile-Arg-Leu-Gly-Ile-Leu (SEQ ID NO: 20)
Ala-Pro-Met-His-His-Met-Lys-Ser-Leu-Tyr-Arg-Ala (SEQ ID NO: 21)
Met-Met-Gln-Arg-Asp-His-His-Gln-His-Met-Arg-Arg (SEQ ID NO: 22)
Met-Lys-Thr-His-His-Gly-Asn-Asn-Ala-Val-Phe-Leu (SEQ ID NO: 23)
Leu-Glu-Pro-Leu-Pro-His-Thr-Pro-Arg-Met-Tyr-Ala (SEQ ID NO: 24)
Gln-Leu-Tyr-Glu-Pro-Asp-Ser-Gly-Pro-Trp-Ala-Pro (SEQ ID NO: 25)
Trp-Met-Thr-Lys-Met-Pro-Thr-Thr-His-Thr-Arg-Tyr (SEQ ID NO: 26)
His-His-Pro-Met-Tyr-Ser-Met-Thr-Arg-Ala-Leu-Pro (SEQ ID NO: 27)
Gly-Ser-Ala-His-Ser-Arg-Asn-Asp-Ala-Ala-Pro-Val (SEQ ID NO: 28)
His-Ser-Pro-Leu-Met-Gln-Tyr-His-Met-Ser-Gly-Thr (SEQ ID NO: 29)
Thr-Ala-His-Met-Thr-Met-Pro-Ser-Arg-Phe-Leu-Pro (SEQ ID NO: 30)
Ala-Cys-Pro-Pro-Thr-Gln-Ser-Arg-Tyr-Cys (SEQ ID NO: 31)
Ala-Cys-Asn-Gly-Met-Leu-Ala-Phe-Gln-Cys (SEQ ID NO: 32)
Ala-Cys-Thr-Pro-Lys-Pro-Gly-Lys-His-Cys

That is, for the organic substance-immobilized structure of the present invention, there is used a procedure in which, when an organic substance is immobilized on the surface of a substrate where at least part of the surface thereof contains aluminum oxide, the binding domain containing the peptide having an amino acid sequence representing an ability to bind to the aluminum oxide is designed to provide an organic substance-binding domain fused product formed by previously binding the binding domain to a desired organic substance to specifically immobilize the organic substance-binding domain fused product to the surface of the substrate containing aluminum oxide through the binding domain portion having an ability to bind to the aluminum oxide.

Therefore, in the organic substance-binding domain fused product formed by previously binding the binding domain, when the organic substance is a biological substance, a chemical reaction that utilizes a reagent that affects the functions (e.g., molecular recognition and catalytic ability) is not used at the time of immobilization of the biological substance-binding domain fused product to the surface of the substrate containing aluminum oxide. Thus, the biological substance to be immobilized will be kept in a state of being able to exert the functions thereof sufficiently.

In addition, depending on an aluminum oxide substrate used for the surface of the substrate, an amino acid sequence having a desired binding ability can be selected in advance through screening. Besides, depending on the objective biological substance, a design for optimizing the binding configuration of the binding domain to be previously bound to the biological substance and the amino acid sequence representing an ability to bind to aluminum oxide in the binding domain can be worked out. Therefore, the organic substance-immobilized structure according to the present invention can be applied extensively to both the aluminum oxide and the organic substance, particularly the biological substance.

In addition, the manufacturing method of an organic substance-immobilized structure in accordance with the present invention is a method of manufacturing an organic substance-immobilized structure characterized by including:

a substrate having a surface at least part of which contains aluminum oxide; and an organic substance immobilized on the surface of the substrate through a binding domain containing at least one or more amino acids, the method being characterized by including the steps of:

(1) making an organic substance-binding domain fused product constructed by coupling the binding domain with the organic product; and (2) immobilizing the organic substance on the surface of the substrate through the binding domain by bringing the organic substance-binding domain fused product into contact with the surface of the substrate to allow at least part of the binding domain in the organic substance-binding domain fused product to bind to the surface of the substrate.

Furthermore, it is preferable that the organic substance be a biological substance containing a protein and the above step (1) of making the organic substance-binding domain fused product include a step of expressing a fused product-type protein constructed by coupling a peptide portion included in the binding domain with a protein included in the biological substance on the basis of a coupling gene having a base sequence constructed by coupling a base sequence encoding the amino acid sequence of a protein included in the biological substance with a base sequence encoding the amino acid sequence of a peptide portion included in the binding domain to encode a combination of two amino acid sequences described above.

Furthermore, a manufacturing method is one characterized in that the above coupling gene has a base sequence in which a base sequence encoding a linker constructed of one or more amino acids is coupled between the base sequence encoding the amino acid sequence of the protein included in the biological substance and the base sequence encoding the amino acid sequence of the peptide portion contained in the binding domain so as to encode a combination of two amino acid sequences described above.

Furthermore, depending on the selection of an organic substance used, the organic substance-immobilized structure of the present invention can be a component to be available in a target substance-capturing element, a target substance-detecting element, a substance-converting element, or a target substance-separating element, or available in all of these elements.

Moreover, the present invention utilizes the present invention of a certain amino acid sequence of a peptide in the binding domain used in the configuration of the above organic substance-immobilized structure of the present invention. In other words, the aluminum oxide affinity peptide of the present invention may be an aluminum oxide affinity peptide characterized by including the whole of at least one amino acid sequence or an amino acid sequence containing at least part thereof selected from the group consisting of amino acid sequences represented by SEQ ID NOS: 1 to 32 described above, or a repetitive structure of any of these amino acid sequences or a complex of these amino acid sequences.

Furthermore, the peptide may be an aluminum oxide affinity peptide containing one or more amino acids selected from those of SEQ ID NOS: 30 to 32, characterized in that the one or more amino acids form a cyclic structure with an intramolecular disulfide binding in the sequence.

Furthermore, the DNA molecule according to the present invention is a DNA molecule characterized by including a DNA encoding an aluminum oxide affinity peptide chain containing the whole of at least one amino acid sequence or an amino acid sequence containing at least part thereof selected from the group consisting of amino acid sequences represented by SEQ ID NOS: 1 to 32 described above, or a repetitive structure of any of these amino acid sequences.

The vector according to the present invention is an expression vector capable of expressing the binding domain containing a peptide composed of the whole of at least one amino acid sequence or an amino acid sequence containing at least part thereof selected from the group consisting of amino acid sequences represented by SEQ ID NOS: 1 to 32 described above, or a repetitive structure of any of these amino acid sequences or a complex of these amino acid sequences and an organic substance containing a protein in at least part thereof as a fused product in a host cell, characterized by including a coupling gene containing a base sequence made of a combination of a base sequence encoding an amino acid sequence of the protein included in the binding domain and a base sequence encoding an amino acid sequence of the protein included in the organic substance so as to encode a combination of the binding domain and the organic substance.

Hereinafter, the configuration of the organic substance-immobilized structure of the present invention and the manufacturing method thereof will be described in more detail.

In the organic substance-immobilized structure of the present invention, at least part of the surface of a substrate is provided with a region from which aluminum oxide is exposed. In the aluminum oxide-exposed region, the organic substance is immobilized in the organic substance-binding domain fused product through the binding domain containing a peptide composed of at least one or more amino acids, which is formed independently from the functional domain derived from the organic substance.

Figure 2:
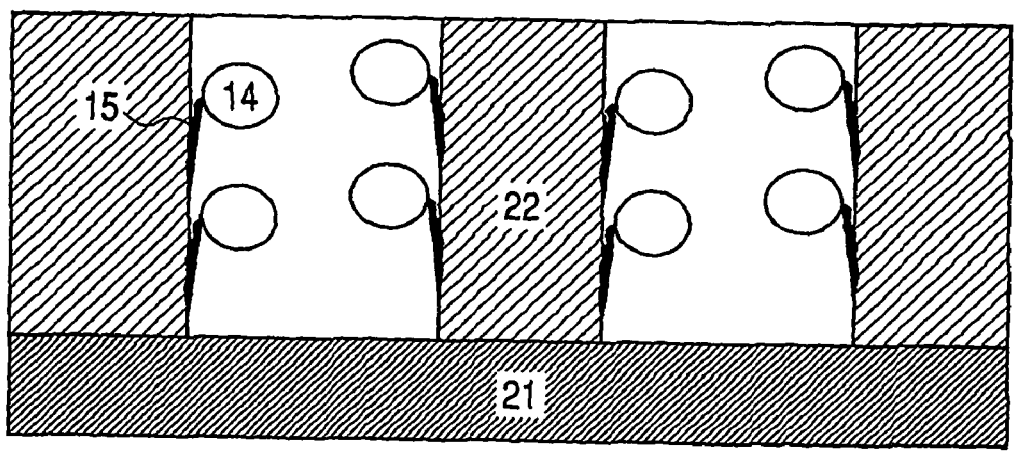
FIG. 2 is a cross sectional diagram schematically showing the configuration of the structure of an example of the organic substance-immobilized structure according to the present invention.
Figure 3:
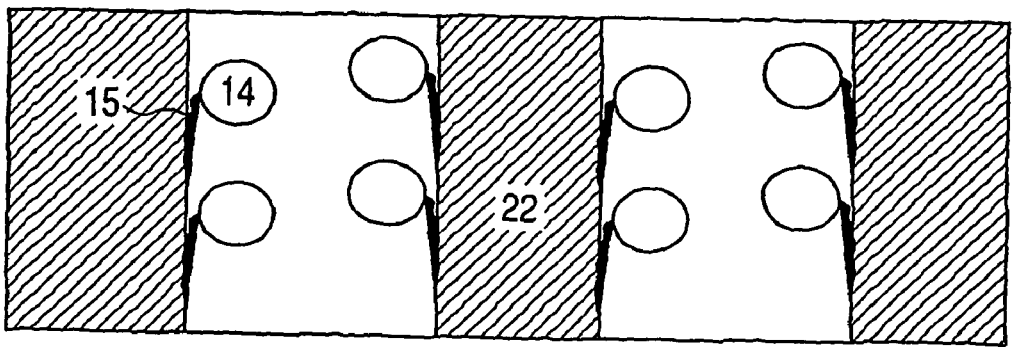
FIG. 3 is a cross sectional diagram schematically showing the configuration of the structure of an example of the organic substance-immobilized structure according to the present invention.

FIGS. 1 to 3 each schematically show an example of the embodiment of the organic substance-immobilized structure in accordance with the present invention.

In the configuration shown in FIG. 1, a substrate is a flat substrate lithe surface of which is provided with an aluminum oxide layer 12 as a coating layer composed of a substrate containing aluminum oxide. The immobilization of the organic substance is carried out on the surface of the aluminum oxide layer 12 alternatively with the binding domain 15. On the other hand, the organic substance itself, which corresponds to the functional domain 14 being coupled with the binding domain 15, is able to perform weak physical adsorption non-selectively on the aluminum oxide layer 12. However, part of the binding domain 15, which specifically binds to the aluminum oxide, binds more dominantly. As a result, due to such a competing process, the organic substance itself corresponding to the functional domain 14 has a low frequency of causing physical adsorption on the surface of the substrate, and it is possible to reduce the non-specific weak adsorption by selecting the immobilization condition. Reference numeral 21 represents a conductive substrate, and reference numeral 22 represents an aluminum oxide porous material.

(Substrate)

As far as the surface of a substrate, for example a substrate, can be provided with a coating layer constructed of a substrate containing aluminum oxide, any of substrates made of various materials known in the art can be appropriately selected and used in accordance with the intended use. The substrate can be appropriately selected from substrates formed using metal materials such as iron, copper, gold, silver, and platinum, a polystyrene-methyl methacrylate copolymer (PMMA), synthetic resin materials typified by polycarbonate (PC), semiconductor materials such as silicon, oxides of silica, sapphire, and so on, and ceramics materials, or complex materials made of combinations of two or more of these materials.

Variations of physical or chemical values caused in the vicinity of the organic substance of the present invention when the substrate is made of an electroconductive material or a complex material prepared by stacking layers of electroconductive layers. Alternatively, the substrate may be made of a translucent material to determine the variations caused in the vicinity of the organic substance of the present invention as, for example, a change in refractive index by means of an optical procedure.

In the case of a detecting element, a converting element, or the like using the structure of the present invention, it is more desirable to select the substrate in sufficient consideration of the matters described above.

(Aluminum Oxide Layer)

At least part of the surface of the substrate is configured such that the surface layer of aluminum oxide is exposed. When the thickness of the aluminum oxide layer 12 formed on the surface of the substrate is determined in the order of nanometers, it is preferable to apply a gas-phase deposition method such as a CVD method more suitable to the thin film formation.

At first, for instance, an aluminum oxide layer is formed on the surface of a substrate by means of a CVD method. Then, in the atmosphere or by means of a heating or electrochemical procedure, an aluminum oxide layer can be obtained by facilitating the oxidation of the aluminum oxide layer formed on the surface of the substrate. In the case of applying the aluminum oxide layer-forming method, there is a need of selecting a substrate that does not cause an alteration or a degrease in characteristics of the substrate itself during the deposition process of the aluminum oxide layer by the CVD method or the oxidation process by the heating or electric procedure.

Furthermore, preliminarily, aluminum oxide material particles are formed and suspended in a dispersion solvent which is selected in consideration of the nature of the substrate material. Then, the suspension of aluminum oxide material particles is applied in a predetermined film thickness and if desired the dispersion solvent is removed by heating, allowing the formation of a layer containing particulate aluminum oxide.

In the case of using any procedure, if there is a large difference in coefficient of thermal expansion between the aluminum oxide layer formed and the substrate, mechanical distortion may be induced in the aluminum oxide layer at the time of a heat treatment to cause peeling or warping of the aluminum oxide layer formed. In consideration of this fact, it is preferable to determine the thickness of the aluminum oxide layer in addition to the selection of the substrate material.

Furthermore, when the aluminum oxide layer 12 is provided as a porous material-coating structure, the specific surface area of the aluminum oxide layer 12 increases because of the presence of fine pores in the porous material. Thus, the total surface area available for the immobilization can be increased.

In addition, comparing with the immobilization of the organic substance on the flat substrate, the porous material-coating structure can be considered to have reduced reaction fields in the respective fine pores. For example, when the structure of the present invention is used as a target material capturing element or a converting element, the average moving distance between the target substance and the organic substance immobilized on the structure of the present invention can be reduced to a large extent, so an effect of increasing the reaction efficiency of molecular recognition can be also expected.

Furthermore, by selecting the pore sizes of the fine pores, the target substance and other contaminate substances can be separated from each other on the basis of the pore sizes of the fine pores.

According to the present invention, when the aluminum oxide layer is provided as a porous material, it is preferable to properly select a suitable pore size so that the characteristics of the above porous material can be exerted, and also depending on the use of the element. In addition, it is preferable to adjust the thickness of the aluminum oxide layer in consideration of the strength of the aluminum oxide layer or the adhesiveness thereof to the substrate, while depending on the demanded characteristics of the adaptive element or the like.

A method of providing the aluminum oxide layer as the porous material layer can be selected from the methods known in the art. For example, an anodic oxidation process may be used for the formation of a porous aluminum oxide layer. The use of the anodic oxidation method allows the formation of the fine pores in the resulting aluminum oxide porous material in the order of nanometers. In addition, the pore size may be adjusted by regulation of an oxidation condition such as an applied voltage.

In FIG. 2 and FIG. 3, an example of the configuration of the aluminum oxide in the organic substance-immobilized structure of the present invention is represented by the respective schematic cross-sectional diagrams.

In FIG. 2, an example of the porous material of the aluminum oxide layer formed on the substrate material is represented by the schematic cross-sectional diagram.

FIG. 3 represents a schematic cross-sectional diagram of an example of a thin film of the aluminum oxide porous material.

(Organic Substance)

In the present invention, the organic substance immobilized on the surface of the substrate can be properly selected depending on the intended use of the organic substance-immobilized substrate to be manufactured. As far as the organic substance used as a functional domain can be coupled with a binding domain containing a peptide constructed of at least one or more amino acids, the type of the organic substance used as a functional domain is not particularly limited. Each of various biological substances, which can be coupled with the binding domain containing a peptide composed of one or more amino acids, can be selected as an organic substance to be immobilized on the surface of the substrate. Specific examples of a biological substance that can be selected as an organic substance to which the present invention is applicable include nucleic acid molecules, amino acids, peptides or proteins, and sugar chains and sugar chain-protein complexes. Of those, the peptides or proteins, and the sugar chains or sugar chain-protein complexes are more preferable.

The peptides include various peptides capable of specifically binding to the target substances and peptide hormones typified by insulin.

In addition, examples of protein molecules, which can be selective for the organic substance to which the present invention can be applied, include enzymes, antibodies, receptor molecules, and scaffolding protein molecules. Those known in the art can be used as the enzymes.

For example, in consideration of the target substance-detecting element for the organic substance-immobilized structure of the present invention, the enzymes include glucose dehydrogenase and glucose oxidase. In consideration of the target substance-converting element for the organic substance-immobilized structure of the present invention, a preferable enzyme is one that converts a substance provided as a raw material into the desired substance. Specific examples thereof include converting enzymes known in the art, such as aminoacylase, lipase, and phosphodiesterase. Furthermore, various protein-refolding assisting proteins including GroEL referred to as molecular chaperones can be immobilized. The antibody molecules to which the present invention can be applied include immunoglobulin molecules collected by various kinds of methods, such as immune-antibody molecules produced as a result of immune reactions caused by the introduction of antigenic substances into test animals and recombinant antibody molecules obtained by partially or wholly altering the structures of the immune antibodies by means of genetic engineering.

The antibodies used in the present invention may be monoclonal or polyclonal antibodies. Those antibody molecules are included in any immunoglobulin class, and can be selected from, for example, human IgG, IgM, IgA, IgD, and IgE. Of those classes, the IgG-class antibody molecules can be used more preferably.

In addition to the immunoglobulin molecules, antibody fragment molecules, including Fab, Fab', and F(ab')$_2$, can be used. For example, the Fab fragment molecule is a fragment molecule almost identical to an antibody fragment molecule obtained by subjecting antibody globulin to papain digestion. F(ab')$_2$ is a fragment molecule almost identical to an antibody fragment molecule obtained by subjecting antibody globulin to pepsin digestion.

Even though there is a method by which those antibody fragment molecules can be prepared by enzymatically or chemically decomposing antibody globulin, a method of recombinant production with genetic engineering can be also applied to most of the cases. Furthermore, a single-chain Fv (scFv), which is considered to be a genetically-engineered recombinant peptide having an antigen-recognizing ability by coupling a heavy chain (VH) with a light chain (VL), which constitute a variable region (Fv), an antigen recognition site in an immunoglobulin molecule, through a peptide constructed of several amino acids of the carboxyl end of one of them and of the amino end of the other.

The scaffolding proteins are proteins or call-adhesion molecules which themselves cannot carry out functions of capturing, converting, and separating target substances, but are capable of binding substances having those functions such as enzymes and antibodies, so the scaffolding proteins can be selected from various known proteins and used.

When the functional domain 14 is the protein as described above and can be produced as a recombinant using a host cell, the binding domain 15 that contains a peptide constructed of one or more amino acids coupled with the functional domain 14 may be configured as a fused protein in which their peptide chains are coupled with each other in line. In this case, a linker sequence having an appropriate number of amino acid residues may be inserted between the functional domain 14 portion and the binding domain 15 portion.

On the other hand, when the organic substance to which the present invention is applied has a sequence corresponding to an unknown protein, nucleic acid molecule, or sugar chain, the biological substance, the binding domain containing the peptide structure, or both of them are previously subjected to chemical modification/conversion such as introduction of a reactive functional group used for their combination as far as the modification and the conversion are within the scope of having no serious impact on their functions, allowing the production of a complex in which the substance and the domain are coupled with each other through chemical bonding. In particular, a binding domain fused product containing a biological substance-peptide structure can be formed by chemically binding between functional groups after previously subjecting the biological substance and/or the binding domain containing the peptide structure to chemical modification/conversion such that the reactive functional groups which can be used for their combination will make a combination of: a maleimide group and a sulfonyl group (—SH); a succinimide group and an amino group; an isocyanate group and an amino group; a halogen and a hydroxy group; a halogen and a sulfonyl group (—SH); an epoxy group and an amino group; or an epoxy group and a sulfonyl group (—SH).

Furthermore, when the organic substance to which the present invention is applied is a lipid molecule, a binding domain complex containing a lipid-peptide structure is produced by: making the "binding domain" having a "hydrophobic peptide structure" containing a plurality of amino acids having free hydrophobic groups such as alanine, valine, leucine, isoleucine, methionine, tryptophan, and phenylalanine in addition to the aluminum oxide binding peptide structure, and then performing hydrophobic binding to the "hydrophobic peptide structure" of the lipid molecule, and may be used instead of the fused product.

(Binding Domain)

In the organic substance-immobilized structure according to the present invention, the binding domain 15 used for immobilization to the surface of the aluminum oxide layer formed on the surface of the substrate can take advantage of a molecule containing a peptide chain constructed of one or more amino acids having an ability to specifically bind to the aluminum oxide layer 12 or a protein containing an amino acid sequence of the peptide chain.

In a preferred embodiment, the binding domain 15 to be used in the present invention has an amino acid sequence constructed of one or more amino acids having an affinity to the aluminum oxide layer 12.

Preferred examples of the amino acid sequence having the affinity to the aluminum oxide layer, which is included in the binding domain, include an amino acid containing the whole of at least one amino acid sequence selected from the group consisting of amino acid sequences represented by SEQ ID NOS: 1 to 32 described above, or an amino acid sequence containing a part thereof. Furthermore, the amino acid sequence may be one containing a repetitive structure of the above amino acid sequence or a complex of plural sequences selected from the amino acid sequences. Besides, the amino acid sequence of any of SEQ ID NOS: 30 to 32 may form a cyclic structure with an intramolecular disulfide binding between cysteines being contained. Those amino acid sequences are those of peptides having affinities to aluminum oxide, which have been finally obtained as a result of concentrated studies of the inventors of the present invention.

The binding domain at least part of which has the peptide can be selectively bound through the aluminum oxide affinity peptide to the substrate having a surface from which aluminum oxide is exposed. In other words, the organic substance-immobilized structure of the present invention can be constructed by those aluminum oxide affinity peptides and the target substance-detecting element, converting element, and separating element using the above structure can obtain their desired characteristic features, respectively.

It can be expected that a higher affinity to aluminum oxide can be attained by forming a repetitive structure made of one or more amino acid sequences described above or a complex of two or more amino acid sequence described above. In addition, the formation of an intramolecular disulfide binding structurally stabilizes the binding domain containing the aluminum oxide affinity peptide and also improves the binding affinity and molecular orientation.

The aluminum oxide affinity peptide as described above may be one having an amino acid sequence defined by screening of a random peptide library or an amino acid sequence reasonably designed on the basis of chemical properties of the aluminum oxide layer.

Hereinafter, a screening method of a random peptide library for acquiring an amino acid sequence having an affinity to the aluminum oxide layer will be described.

The random peptide libraries available in screening include random synthetic peptide libraries in which random peptides are chemically synthesized in soluble forms, solid-phase immobilized peptide libraries in which random peptides are synthesized on resin beads, peptide libraries in which DNA of random sequences chemically synthesized are biosynthesized in ribosomal cell-free systems, for example a phage display peptide library prepared by coupling a random synthetic gene with a gene for the N-terminal end of a surface protein of M13 phage (such as a gene III protein), and a random peptide library displayed using similar procedures by fusing a bacterial layer protein, Omp A (Francisco, 1993, Proc. Natl., Acad. Sci. USA, 90, 10444-10448 or Pistor and Hoborn, 1989, KIin. Wochenschr., 66, 110-116), PAL (Fuchs et al., 1991, Bio/Technology, 9, 1369-1372), Lamb (Charbit et al., 1988, Gene, 70, 181-189 and Bradbury et al., 1993, Bio/Technology, 1565-1568), finbrin (Hedeg Aard and Klem M., 1989, Gene, 85, 115-124 and Hofnung, 1991, Methods Cell Biol., 34, 77-105), and an IgA protease-6 region (Klauser et al., 1990, EMBO J., 9, 1991-1999).

As a procedure of screening an amino acid sequence having an affinity to aluminum oxide using those random peptide libraries, when a chemical synthetic peptide library is used, a peptide library is brought into contact with (or adsorbed to) a support or a substrate such as a column support or a plate, a fine particle, or the like, which is made of aluminum oxide and represents the surface characteristics which are the same as or similar to those of the structure of the present invention, and then a peptide having no affinity to the aluminum oxide layer is removed by a washing step, followed by collecting a peptide binding to the aluminum oxide layer. After that, by using the Edman degradation method or the like, an amino acid sequence thereof can be determined.

On the other hand, when the phage display peptide library is used, a phage library that displays the above various peptides is added to and brought into contact with the surface of the above support, substrate covered with the aluminum oxide, or fine particle, followed by washing the non-specific binding phages out under selected washing conditions. After washing, the remaining phages are eluted with acid or the like and are then neutralized, followed by infecting E. coli bacteria to amplify the phage. Repeating such selection (panning) several times allows a plurality of clones each having an affinity to the target aluminum oxide layer to be concentrated.

Here, for obtaining a single clone, colonies are formed on a culture plate in a state of being infected again with E. coli. Each of the respective single colonies is incubated in a liquid medium, and then phages that reside in the supernatant of the medium are purified by means of precipitation with polyethylene glycol or the like to collect phagemids. By analyzing the base sequence of the phagemids, an amino acid sequence of the peptide having an ability to bind to the objective aluminum oxide can be known.

A screening procedure using the phage display peptide library described above is able to concentrate phages that represent a peptide more strongly binding to the aluminum oxide layer among a wide variety of peptide display phage libraries (typically $10^9$ or more), so that it can be preferably used for the purpose of the present invention.

An example of a method of constructing a phage display random peptide library involves coupling a gene for the N-terminal end of the surface protein (e.g., gene III protein) of M13 phage with a synthetic gene encoding a random amino acid sequence. The method may be one of those reported in Scott, J. K. and Smith, G. P., Science Vol. 249, 386 (1990), Cwirla, S. E. et al., Proc. Natl. Acad. Sci. USA Vol. 87, 6378, (1990), and so on. The size of the inserted gene is not particularly limited as far as a peptide can be stably expressed. However, it is preferable that the inserted library have a suitable length corresponding to 6 to 40 amino acids (corresponding to a molecular weight of about 600 to 4,000), preferably 7 to 18 amino acids for allowing the resulting-library to include all of the random sequences and to have the affinity.

In addition, it is also possible to display, on a phage surface protein, a cyclic peptide having an affinity to aluminum oxide, in which two or more cysteines are provided in a peptide sequence which can be displayed on the phage surface and an intramolecular disulfide binding is formed between the cysteines. The amino acid sequence of the aluminum oxide affinity peptide obtained by screening of the phage display peptide library may be also constructed of a serial repetitive structure as described above. When two or more amino acid sequences are obtained, a sequence constructed of an appropriate combination of amino acid sequences, which are connected in series, of the whole or part of at least one amino acid sequence selected from the group consisting of those amino acid sequences may be used as an amino acid sequence having an affinity to the aluminum oxide layer. In this case, it is preferable to provide an appropriate spacer sequence between two different amino acid sequences. The spacer sequence is preferably of about 3 to 400 amino acids, and also the spacer sequence may include any kind of amino acid. Most preferably, the spacer sequence is one that does not prevent the functions of the functional domain and does not prevent the binding of an organic substance to the aluminum oxide layer.

The amino acid sequences each having an affinity to aluminum oxide, which can be used in the present invention, are amino acid sequences determined by screening of a random peptide library, as well as amino acid sequences reasonably designed on the basis of the chemical properties of the aluminum oxide layer. A library may be constructed of those amino acid sequences, and thus an amino acid sequence having a higher affinity can be selected from the library using the screening method as described above.

A fused protein obtained by coupling the binding domain containing the amino acid sequence having the aluminum oxide affinity peptide constructed of one or more amino acids with a protein having desired characteristic features to be provided as a functional domain is one stably produced by constructing an expression vector such that a gene encoding an amino acid sequence of the binding domain containing at least one or more aluminum oxide affinity peptides according to the present invention is inserted into the upstream or downstream of a gene encoding the functional domain, while their reading frames are coincident with each other.

Furthermore, when one or more amino acid linkers are provided between the binding domain and the functional domain, a base sequence that encodes the linker sequence can be inserted into a base sequence encoding the binding domain and the functional domain, while their reading frames are kept to be matched. Consequently, the aluminum oxide layer affinity portion can be expressed by coupling with the N- or C-terminal end of a protein being considered to be the functional domain 14. In addition, an appropriate liner sequence may be inserted so as to be expressed as a binding domain.

The linker sequence is preferably of about 3 to 400 amino acid, and also the linker sequence may include any kind of amino acids. Most preferably, the linker sequence is one that does not prevent the functions of a protein provided as the functional domain 14 and does not prevent the binding of the binding domain 15 to the aluminum oxide layer.

A promoter sequence used in the expression vector, an antibiotic resistance base sequence for confirming transformation, and so on can be appropriately selected from those known in the art and used.

The immobilization of the fused protein thus obtained to the aluminum oxide layer is carried out through an amino acid sequence (hereinafter, referred to as an aluminum oxide layer affinity portion 15a) obtained by the screening procedure in the binding domain 15 which is fused with the functional domain 14 and then translated.

In the aluminum oxide layer 12 having a hydrophilic surface, the immobilization to the aluminum oxide layer 12 through the binding domain 15 can be strengthened by selecting, as the aluminum oxide layer affinity portion 15a to be fused with the functional domain 14 and to be translated, a sequence containing a number of amino acids having hydrophilic groups, particularly cationic residues or hydroxy groups, from the amino acid sequences.

A method of isolating and purifying a fused protein constructed by coupling the protein provided as the functional domain 14 and the binding domain containing the aluminum oxide layer affinity portion 15a can be any of methods as far as the method retains the activity of the protein provided as the functional domain.

Hereinafter, a method of manufacturing the organic substance-immobilized structure of the present invention will be described.

A step of immobilizing an organic substance on the aluminum oxide layer 12 through a binding domain containing the aluminum oxide layer affinity portion 15a can be attained by bringing a fused product constructed of the organic substance and the binding domain into contact with the aluminum oxide layer 12 in an aqueous medium.

In the present invention, the composition of the aqueous medium used in the step of carrying out the immobilization through the binding domain may be one that does not prevent binding or converting reaction of the objective compound, which is performed by an organic substance to be immobilized, such as a biological substance. However, in order to skip the subsequent steps, the composition of the aqueous medium may be one capable of exerting a binding or converting reaction activity represented by the biological substance. Here, for example, a buffer may be used as the composition of the aqueous medium that exerts the activity. Examples of the buffer include general buffers used in biological reactions, such as an acetic acid buffer, a phosphoric acid buffer, a potassium phosphate buffer, a 3-(N-morpholino)propanesulfonic acid (MOPS) buffer, an N-tris(hydroxymethyl)methyl-3-aminopropane sulfonic acid (TAPS) buffer, a tris-HCl buffer, a glycine buffer, and a 2-(cyclohexylamino)ethane sulfonic acid (CHES) buffer, which are preferably used. For instance, when the biological substance is a PHA synthetic enzyme protein as described below, the concentration of a buffer used for exerting an enzymatic activity is generally in the range of 5 mM to 10 M, preferably in the range of 10 mM to 200 mM. In addition, pH is adjusted to 5.5 to 9.0, preferably 7.0 to 8.5.

The immobilization of the fused product constructed of the organic substance and the binding domain on the aluminum oxide layer 12 of the substrate's surface through the binding domain 15 can be attained by providing a liquid, in which a substrate on which the aluminum oxide layer 12 is mounted is immersed, as a solution where a fused product composed of the organic substance and the binding domain is dissolved in the aqueous medium so as to become a predetermined concentration. At this time, it is preferable to shake a reaction container or stir the contents thereof appropriately so as to allow the binding domain portion containing the aluminum oxide layer affinity portion 15a included in the fused product constructed of the organic substance and the binding domain to bind uniformly to the surface of the aluminum oxide layer.

In the above immobilization process, the composition of the aqueous medium used is preferably set in consideration of a change in electrical charges of the surface charges or hydrophobic property of the aluminum oxide layer affinity portion 15a contained in the binding domain and the aluminum oxide layer because those factors vary depending on a pH or a salt concentration of the aqueous medium. For example, the hydrophobicity of both of them can be increased by an increase in salt concentration.

In addition, it is also possible to set the composition of the solution suitable for the binding of the binding domain by investigating whether the aluminum oxide layer 12 is hydrophilic or hydrophobic by previously measuring the wetting angle of the solvent to the aluminum oxide layer 12 provided on the surface of the substrate. Furthermore, the binding amount of the aluminum oxide layer affinity portion 15a to the surface of the aluminum oxide layer 12 may be directly determined to set the composition of the solution. The determination of the binding amount may be carried out using, for example, a method by which a fused product solution constructed of an organic substance and the binding domain at known concentrations is added to a certain area of an aluminum oxide layer and subjected to immobilization treatment, and then the concentration of the fused product constructed of the organic substance and the binding domain remaining in the solution is determined, followed by calculating a binding amount by a subtraction procedure.

Duration of the immobilization treatment for the biological substance is preferably in the range of 1 minute to 48 hours, more preferably in the range of 10 minutes to 3 hours. In general, it is not preferable to leave the substance standing or leave the substance for a much longer period because the desired functional activity of the immobilized biological substance is likely to lower.

EXAMPLES

Hereinafter, the present invention will be described in more detail by way of examples. In addition, those examples are illustrative of the best mode of the present invention. However, the present invention is not limited to configurations described in those examples.

In the examples described below, as for the organic substance immobilized structure, particularly the biological substance immobilized substrate of the present invention, a polyhydroxyalkanoate (PHA) synthetic enzyme protein is employed as a biological substance that corresponds to a functional domain and an aluminum oxide layer affinity peptide is employed as a binding domain. Then, a biological substance-immobilized substrate, in which the fused product PHA synthetic enzyme protein constructed of the aluminum oxide layer affinity peptide being coupled with the N-terminal of the PHA synthetic enzyme protein through a linker sequence is immobilized on a substrate having a surface covered with an aluminum oxide layer, is exemplified for describing the configuration of the biological substance immobilized substrate and a manufacturing method therefor, specifically.

Furthermore, a method of obtaining an amino acid sequence of the aluminum oxide layer affinity peptide used as the binding domain will be described specifically.

Prior to those examples, in Reference Example 1, a method of producing a PHA synthetic enzyme protein as the biological substance corresponding to the functional domain by means of gene recombination, an enzymatic activity of the recombinant PHA synthetic enzyme protein, and a method of determining the enzymatic activity will be described in advance.

Furthermore, in the examples, for a biological substance immobilized substrate having a fused product type PHA synthetic enzyme protein immobilized on a substrate having a surface covered with an aluminum oxide layer, an enzymatic activity retained by the fused product type PHA synthetic enzyme protein being immobilized can be examined through evaluation on the basis of an enzymatic activity of the recombinant PHA synthetic enzyme protein.

Reference Example 1

A transformant having an ability to produce a PHA synthetic enzyme and a transformant having an ability to produce a PHA synthetic enzyme by production of the PHA synthetic enzyme with recombination were manufactured by the following methods:

At first, strain YN2 (*Pseudomonas cichorii* YN2, FERM BP-7375) having an ability to produce a PHA synthetic enzyme was incubated overnight at 30° C. in 100 ml of an LB medium (1% polypepton, 0.5% yeast extract, and 0.5% sodium chloride, pH 7.4), and then chromosomal DNA of the strain YN2 was isolated and collected by the method of Manner et al. The chromosomal DNA thus obtained was completely digested with the restriction enzyme HindIII. A cloning vector used was pUC18 and cleaved by the restriction enzyme HindIII. The end of the product was subjected to a dephosphorization process (Molecular Cloning, 1, 572 (1989); Cold Spring Harbor Laboratory Press), and then a chromosomal DNA fragment completely digested with HindIII was coupled and inserted into a cleaved site (cloning site) of the vector using a DNA ligation kit Ver. II (Takara Shuzo Co., Ltd.). By using the plasmid vector incorporated with the chromosomal DNA fragment, *E. coli* (*Escherichia coli*) strain HB101 was transformed to make a DNA library of the strain YN2.

Next, for selecting a DNA fragment containing a PHA synthetic enzyme gene originated from the strain YN2, a probe for colony hybridization was prepared. Oligonucleotides consisting of base sequences of SEQ ID NO: 37 and SEQ ID NO: 38 were synthesized, respectively (Amersham Pharmacia Biotech). Then, by using these two different origonucleotides as a pair of primers and the chromosomal DNA as a template, PCR amplification was carried out. A DNA fragment was isolated as PCR amplification product and then used as a probe for colony hybridization. The probe was labeled using a commercially-available alkaline phosophatase-labelling enzyme, AlkPhosDirect (Amersham Pharmacia Biotech). By using the resulting enzyme-labeled probe, A *E. coli* strain having a recombinant plasmid containing the objective PHA synthetic enzyme gene was selected from the chromosomal DNA library of the strain YN2 by means of a colony hybridization method. From the selected bacterial strain, the plasmid was collected by an alkaline process. Consequently, a DNA fragment containing a PHA synthetic enzyme gene originated from the strain YN2 was obtained.

(SEQ ID NO: 37) Base sequence of forward primer 5'-TGCTGGAACT GATCCAGTAC-3'

(SEQ ID NO: 38) Base sequence of reverse primer 5'-GGGTTGAGGA TGCTCTGGAT GTG-3'

The PHA synthetic enzyme gene DNA fragment obtained herein was incorporated by gene recombination in a vector pBBR 122 (Mo Bi Tec) containing a wide host range replication region which does not belong to an incompatible group of IncP, IncQ, or IncW. The recombinant plasmid was transformed into *Pseudomonas cichorii* strain YN2ml (PHA synthetic ability defective strain) by an electroporation process. The transformed strain YN2ml recovered its PHA synthetic ability and showed complementarity. Therefore, it was confirmed that the selected gene DNA fragment contains a PHA synthetic enzyme gene region which can be translated into a PHA synthetic enzyme at least in *Pseudomonas cichorii* strain YN2ml.

The base sequence of the respective DNA fragments containing the PHA synthetic enzyme gene originated from the strain YN2 was determined. As a result, it was confirmed that the defined base sequence includes two different base sequences represented by SEQ ID NO: 33 and SEQ ID NO: 34 encoding the respective peptide chains. Proteins composed of two different peptide chains encoded by the two base sequences had PHA synthetic enzyme activities as described below, respectively. Thus, it was confirmed that the base sequences represented by SEQ ID NO: 33 and SEQ ID NO: 34 were PHA synthetic enzyme genes, respectively. That is, an amino acid sequence represented by SEQ ID NO: 35 was encoded by the base sequence of SEQ ID NO: 33, while an amino acid sequence represented by SEQ ID NO: 36 was encoded by the base sequence of SEQ ID NO: 34. The PHA synthetic ability could be also exerted from either of the proteins containing these two different amino acid sequences.

For the PHA synthetic enzyme gene having the base sequence represented by SEQ ID NO: 33, a full-length PHA synthetic enzyme gene was prepared again by carrying out PCR amplification using the chromosomal DNA as a template.

For the base sequence represented by SEQ ID NO: 34, an oligonucleotide (SEQ ID NO: 41) provided as an upstream primer and having a base sequence that is upstream of its initiation codon and an oligonucleotide (SEQ ID NO: 39) provided as a downstream primer and having a base sequence that is downstream of its terminal codon were designed and synthesized (Amersham Pharmacia Biotech). PCR amplification was carried out such that these two different oligonucleotides were used as a pair of primers and the chromosomal DNA was used as a template, amplifying a full-length PHA synthetic enzyme gene (LA-PCR kit; Takara Shuzo Co., Ltd.).

(SEQ ID NO: 41) Base Sequence of Primer on Upstream Side

5'-GGACCAAGCT TCTCGTCTCA GGGCAATGG-3'

(SEQ ID NO: 39) Base sequence of primer on downstream side

5'-CGAGCAAGCT TGCTCCTACA GGTGAAGGC-3'

Similarly, for the PHA synthetic enzyme gene having the base sequence represented by SEQ ID NO: 34, PCR amplification was carried out using the chromosomal DNA as a template, re-preparing a full-length PHA synthetic enzyme gene. For the base sequence represented by SEQ ID: 34, an oligonucleotide (SEQ ID NO: 40) provided as an upstream primer and having a base sequence that is upstream of its initiation codon and an oligonucleotide (SEQ ID NO: 42) provided as a downstream primer and having a base sequence that is downstream of its terminal codon were designed and synthesized, respectively (Amersham Pharmacia Biotech). By using this oligonucleotide as a primer, PCR amplification was carried out, amplifying the full-strength of the PHA synthetic enzyme gene (LA-PCR kit; Takara Shuzo Co., Ltd.).

(SEQ ID NO: 40) Base Sequence of Primer on Upstream Side

5'-GTATTAAGCT TGAAGACGAA GGAGTGTTG-3'

(SEQ ID NO: 42) Base Sequence of Primer on Downstream Side

5'-CATCCAAGCT TCTTATGATC GGGTCATGCC-3'

Next, two different PCR-amplified fragments, which contained the full-length PHA synthetic enzyme gene, obtained as described above were completely digested using the restriction enzyme HindIII, respectively. In addition, the expression vector pTrc99A was also cleaved by the restriction enzyme HindIII, followed by subjecting it to a dephosphorization process (Molecular Cloning, 1, 572 (1989); Cold Spring Harbor Laboratory Press). Then, each of the two different PCR-amplified fragments containing the full-length PHA synthetic enzyme gene, in which unnecessary base sequences were removed from both ends, was coupled with the HindIII-cleaved sites of the expression vector pTrc99A using a DNA ligation kit Ver. II (Takara Shuzo Co., Ltd.), making two different recombinant plasmids.

From the recombinant plasmids thus obtained, $E.\ coli$ ($Escherichia\ Coli$ HB101, Takara Shuzo, Co., Ltd.) was transformed by a calcium chloride method. The resulting recombinants were incubated and then the application of the recombinant plasmids was performed, followed by collecting the respective recombinant plasmids. The recombinant plasmid that retains the full-length PHA synthetic enzyme gene DNA containing the base sequence of SEQ ID: 33 was referred to as pYN2-C1 (originated from SEQ ID: 37). Also, the recombinant plasmid that retains the full-length PHA synthetic enzyme gene DNA containing the base sequence of SEQ ID NO: 34 was referred to as pYN2-C2 (originated from SEQ ID NO: 38).

By using each of the recombinant plasmids pYN2-C1 and pYN2-C2, $E.\ coli$ ($Escherichia\ coli$ HB101fB fadB defective strain) was transformed by a calcium chloride method to obtain recombinant $E.\ coli$ strains that retain the respective recombinant plasmids, a pYN2-C1 recombinant strain and a pYN2-C2 recombinant strain were obtained, respectively.

Each of the pYN2-C1 and pYN2-C2 recombinant strains was inoculated in 200 ml of an M9 medium containing 0.5% of yeast extract and 0.1% of octanoic acid, followed by incubating at 37° C. while shaking at 125 strokes/min. After 24 hours passed, bacterial cells were collected by centrifugation and then plasmid DNA was collected by an ordinary method.

For the pYN2-C1, an oligonucleotide (SEQ ID NO: 43) provided as an upstream primer and an oligonucleotide (SEQ ID NO: 44) provided as a downstream primer were designed and synthesized, respectively (Amersham Pharmacia Biotech). PCR amplification was carried out such that these two different oligonucleotides were used as a pair of primers and the pYN2-C1 was used as a template, resulting in a DNA as an amplified product having BamHI and SacI restriction sites on its upstream side and SpeI and XhoI restriction sites on its downstream side (LA-PCR kit; Takara Shuzo Co., Ltd.).

Upstream Primer (SEQ ID NO: 43):

5'-AGTGGATCCT CCGAGCTCAG TAACAAGAGT AACGATGAGT

TGAAG-3'

Downstream Primer (SEQ ID NO: 44):

5'-ATACTCGAGA CTACTAGTCC GTTCGTGCAC GTACGTGCCT

GGCGC-3'

Similarly, for the pYN2-C2, an oligonucleotide (SEQ ID NO: 45) provided as an upstream primer and an oligonucleotide (SEQ ID NO: 46) provided as a downstream primer were designed and synthesized, respectively (Amersham Pharmacia Biotech). PCR amplification was carried out such that these two different oligonucleotides were used as a pair of primers and the pYN2-C2 was used as a template, resulting in a DNA including a full-length PHA synthetic enzyme gene as an amplified product, which has a BamHI restriction site on its upstream side and an XhoI restriction site on its downstream side (LA-PCR kit; Takara Shuzo Co., Ltd.).

Upstream Primer (SEQ ID NO: 45):

5'-ATACTCGAGA CTACTAGTGC GCACGCGCAC GTAAGTCCCG

GGCGC-3'

Downstream Primer (SEQ ID NO: 46):

5'-AGTGGATCCT CCGAGCTCCG CGATAAACCT GCGAGGGAGT

CACTA-3'

The purified PCR-amplified products were digested with the restriction enzymes BamHI and XhoI and then inserted into the corresponding sites of plasmid pGEX-6P-1 (Amersham Pharmacia Biotech), respectively. By using these two different vectors (pGEX-C1 and pGEX-C2), $E.\ coli$ (JM109) was transformed to obtain expression bacterial strains. The introduction of expression vectors into the respective bacterial cells was confirmed by checking the molecular weights of DNA fragments obtained by treating plasmid DNA prepared in large quantity using Miniprep (Wizard Minipreps DNA Purification Systems, manufactured by PROMEGA Co., Ltd.) with the restriction enzymes BamHI and XhoI. Each of the resulting expression bacterial cells was pre-cultured overnight in 10 ml of an LB-Amp medium, and then 0.1 ml of the culture was added to 10 ml of the LB-Amp medium, followed by incubating at 37° C. while shaking at 170 rpm for 3 hours. Subsequently, IPTG (1 mM in final concentration) was added and further incubated at 37° C. for 4 to 12 hours.

The IPTG-induced $E.\ coli$ cells were centrifuged (800×g, 2 minutes, 4° C.) and collected, followed by re-suspending in 1/10 volume of PBS at 4° C. The bacterial cells were crushed by freeze-thawing, and sonication and then centrifuged (8000×g, 10 minutes, 4° C.) to remove solid residual matters. By using SDS-PAGE, the presence of the objective protein being expressed (GST-fused protein) in a supernatant was confirmed. Then, the GST-fused protein being induced and expressed was purified using glutathione-sepharose 4B (Glutathion Sepharose 4B beads: manufactured by Amersham Pharmacia Biotech, Co., Ltd.).

The glutathion sepharose used was processed in advance to prevent non-specific adsorption. That is, the glutathion sepharoseu was washed three times with an equal volume of PBS (8,000×g, 1 minute, 4° C.), followed by adding an equal volume of a 4%-BSA-containing PBS to carry out treatment at 4° C. for 1 hour. After the treatment, it was washed twice with an equal volume of PBS and then re-suspended in a ½-volume of PBS. Subsequently, 40 μl of pre-treated glutathion sepharose was added to 1 ml of a cell-free extract and gently stirred at 4° C. The stirring treatment allows the GST-fused proteins GST-YN2-C1 and GST-YN2-C2 to be adsorbed on the glutathion sepharose using the binding ability of the fusion partner GST.

After adsorption, the resultant was centrifuged (8,000×g, 1 minute, 4° C.) to collect glutathion sepharose, followed by washing three times with 400 μl of PBS. Subsequently, 40 μl of 10-mM glutathion was added and stirred at 4° C. for 1 hour, eluting the adsorbed GST-fused protein. A supernatant containing the GST-fused protein was collected, followed by dialysis with respect to PBS to purify the GST-fused protein. After the purification, the SDS-PAGE confirmed that the product showed a single band.

Each 500-μg GST-fused protein was digested with PreScission protease (Amersham Pharmacia Biotech, 5U) and then a fusion partner GST portion at the N-terminal and a PHA synthetic enzyme protein at the C-terminal were separated from each other, followed by removing the protease and GST through a glutathione sepharose column. A flow-through fraction of the glutathione sepharose column was passed through a Sephadex G200 column being equilibrated with PBS, obtaining final purified products of the expression proteins YN2-C1 and YN2-C2, respectively. By using the SDS-PAGE, the expression proteins YN2-C1 and YN2-C2 being finally purified were confirmed to show single bands of 60.8 kDa and 61.5 kDa, respectively.

The activity of each purified enzyme protein was determined.

Activity measurement of the PHA synthetic enzyme was carried out according to the following procedures based on an evaluating method including coloring CoA with 5,5'-dithio-bis-(2-nitrobenzoic acid) and measuring the amount of the CoA released in the process of converting 3-hydroxyacyl CoA provided as a substrate to PHA by polymerization with a catalytic action of the PHA synthetic enzyme.

Reagent 1:
Bovine serum albumin (manufactured by Sigma Co., Ltd.) was dissolved in 0.1 M tris-HCl buffer (pH 8.0) in an amount of 3.0 mg/mM.

Reagent 2:
3'-hydroxyoctanoyl CoA was dissolved in 0.1 M tris-HCl buffer (pH 8.0) in an amount of 3 mg/ml.

Reagent 3:
Trichloroacetic acid was dissolved in 0.1 M tris-HCl buffer (pH 8.0) in an amount of 10 mg/ml.

Reagent 4:
5,5'-dithiobis-(2-nitrobenzoic acid) was dissolved in 0.1 M tris-HCl buffer (pH 8.0) in an amount of 2.0 mM.

A first reaction (PHA synthetic reaction): 100 μl of Regent 1 was added and mixed in 100 μl of a sample (enzyme) solution, and pre-incubated at 30° C. for 1 minute, and the mixture was then added and mixed with 100 μl of Reagent 2 and pre-incubated at 30° C. for 1 to 30 minutes, followed by terminating an enzymatic reaction by the addition of Reagent 3.

A second reaction (coloring reaction of free CoA): The first reaction solution that stopped the reaction was centrifuged (15,000×g, 10 minutes) to collect a supernatant. Then, 500 μl of the supernatant was added with 500 μl of Reagent 4 and incubated at 30° C. for 10 minutes, followed by measuring the absorbance at 412 nm to determine the level of the contained CoA.

Calculation of enzymatic activity: An amount of enzyme that causes the release of CoA in an amount of 1 μmol per minute is defined as 1 unit (U). In addition, the concentration of protein in the sample was measured using a micro-BCA protein quantitative assay reagent kit (manufactured by Pierce Chemical Co., Ltd.). The results of the activity measurement on each purified enzyme are shown in Table 1.

TABLE 1

| PHA synthetic enzyme | Activity | Specific activity |
|---|---|---|
| YN2-C1 | 2.1 U/ml | 4.1 U/mg protein |
| YN2-C2 | 1.5 U/ml | 3.6 U/mg protein |

Depending on the measured activities, the above enzyme solution was concentrated using an agent for concentrating a biological solution sample ("Mizubutori Kun" AB-1100, manufactured by ATTO Corporation), resulting in 10 U/ml of a purified enzyme solution.

In the examples described below, the PHA synthetic enzyme protein YN-C1 having a high specific activity will be used.

Example 1

Procurement of Amino Acid Sequence Having Affinity to Aluminum Oxide Nanoholes

1) Selection of Aluminum Oxide Affinity Phage by Panning Technique (Step 1)
With 0.1% Tween-20/TBS buffer (50 mM tris-HCl, pH 7.5, 150 mM NaCl (hereinafter, referred as to TBST buffer)), $2 \times 10^{11}$ pfu of the PhD.-12 phage display peptide library (NEW ENGLAND BIOLAB) was diluted to 0.5 ml to obtain a library suspension.

(Step 2)
For procurement of the amino acid sequence, 0.5 ml of the above library suspension was added into one well of a flat-bottomed 24-well titer plate in which one aluminum oxide membrane (60 μm in thickness, 13 mm in diameter, pore size 0.2 μm, trade name: Anodisc Membrane, manufactured by Whatman) was placed, and left to stand at 25° C. for 30 minutes.

(Step 3)
The supernatant was discarded and the Anodisc Membrane was washed ten times with 2 ml of TBST buffer within the above well.

(Step 4)
After 0.5 ml of elution buffer (0.2M Glycine-HCl (pH 2.2), 1 mg/ml BSA) was added to the Anodisc Membrane which had been already washed, and then gently shaken for 10 minutes, the supernatant was transferred into another well in the microtiter plate. To the dispensed supernatant, 75 µl of 1 M tris-HCl (pH 9.1) was added for neutralization to obtain a phage eluted from the Anodisc Membrane.

(Step 5)

The eluted phage was infected with E. coli ER2537 (manufactured by NEW ENGLAND BIOLAB) at the early stage of logarithmic growth phase and amplified according to the following procedures.

Following infection, the E. coli was cultured at 37° C. for 4.5 hours. Subsequently, by centrifugation, the phage was separated from the E. coli and precipitated from the supernatant by polyethyleneglycol to be purified. The phage which had been amplified and purified was suspended into TBS buffer. The above phage suspension was infected with the E. coli in appropriate dilution series, thereby measuring its titer.

(Step 6)

For the phage contained in the suspension which had been primary screened to the Anodisc Membrane, the screening procedure in Step 1 to Step 5 described above was additionally repeated four times. However, for the secondary and subsequent screening, the washing condition in Step 3 was made more rigorous by increasing the concentration of Tween-20 in TBST buffer utilized for washing to 0.5% (hereinafter, 0.5% TBST buffer) to sort out the phage showing a higher affinity to the Anodisc Membrane. In addition, for the tertiary (the second time) and subsequent screening, the phage separated from the Anodisc Membrane by washing in Step 3 was applied to the same procedure and its titer was measured. This separated phage would be used as control.

Table 2 shows the titer of the phages eluted from the Anodisc Membrane in each time of the primary screening to the fifth screening.

TABLE 2

Titer of phage eluted in each time of screenings

| | Stock Solution (A) | Control Binding (B) | Anodisc Membrane Binding (C) | C/A | C/B |
|---|---|---|---|---|---|
| 1$^{st}$ time | $2.0 \times 10^{11}$ | | $4.7 \times 10^{3}$ | $2.4 \times 10^{-8}$ | |
| 2$^{nd}$ time | $2.0 \times 10^{11}$ | $5.3 \times 10^{2}$ | $1.8 \times 10^{3}$ | $9.0 \times 10^{-9}$ | 3.4 |
| 3$^{rd}$ time | $2.0 \times 10^{11}$ | $8.0 \times 10^{1}$ | $7.0 \times 10^{3}$ | $3.5 \times 10^{-8}$ | $8.8 \times 10^{1}$ |
| 4$^{th}$ time | $2.0 \times 10^{11}$ | $2.0 \times 10^{1}$ | $1.8 \times 10^{4}$ | $9.0 \times 10^{-8}$ | $9.0 \times 10^{2}$ |
| 5$^{th}$ time | $2.0 \times 10^{11}$ | 1.0 | $3.5 \times 10^{4}$ | $1.8 \times 10^{-7}$ | $3.5 \times 10^{4}$ |

(Units of A, B, and C = pfu/µl)

The phage eluted in the final screening step, which was sorted out in the above screening procedure, was cloned by its infection with a large excess of E. coli.

After each of the separated clones was infected with E. coli and amplified, ssDNA was prepared from the phages of each clone and the base sequence in the random region was decoded, thereby obtaining the phages of 51 clones having high affinities to the Anodisc Membrane.

The obtained phages of 51 clones were evaluated for affinity to aluminum oxide by the phage ELISA. In addition, the DNA sequences encoding each phage-displayed peptide portion were analyzed to determine the amino acid sequence of the peptide showing the binding ability to aluminum oxide.

2) Evaluation of Aluminum Oxide Affinity by Phage ELISA (Step 1)

For the phage suspensions of individual clones of the above 51 clones which had been sorted out in screening described above, $2 \times 10^{11}$ pfu equivalents of these suspensions were diluted with 0.5% TBST buffer to be brought to 0.5 ml.

(Step 2)

All of the above phage suspensions were each added to one well in a flat-bottomed 24-well titer plate in which one Anodisc Membrane was placed, and were left to stand at 25° C. for 30 minutes.

(Step 3)

The supernatant was discarded and the Anodisc Membrane was washed ten times with 2 ml of 0.5% TBST buffer within the above well.

(Step 4)

To the Anodisc Membrane in the above well which had been already washed, 0.5 ml of an HRP binding anti-M13 antibody solution (1 µl of anti-M13 antibody (manufactured by NEW ENGLAND BIOLAB) was suspended in 10 ml of TBST) was added, and the whole was gently shaken for 60 minutes. Subsequently, the supernatant was discarded and the mixture was washed 5 times by repeating the washing procedure with 2 ml of 0.5% TBST buffer.

(Step 5)

The treatment was applied to the phage bound on the Anodisc Membrane, in which this phage was reacted with the above HRP binding anti-M13 antibody. To the well in which this treated Anodisc Membrane was placed, 0.5 ml of Detection Reagent 1 (Amersham Pharmacia, #RPN2209) was added.

Furthermore, 0.5 ml of Detection Reagent 2 (Amersham Pharmacia #RPN2209) was added thereto. After a lapse of three minutes, the emission intensity from luminol at 420 nm generated by the effect of the labeled enzyme HRP in the HRP binding anti-M13 antibody was measured.

The result of evaluation for each clone is shown in Table 3. $I_{420}$ indicates the emission intensity at 420 nm.

TABLE 3

Result of evaluation for aluminum oxide affinity by phage ELISA

| Clone No | 1 | 2 | 3 | 4 | 5 | 6 | 7 | 8 |
|---|---|---|---|---|---|---|---|---|
| $I_{420}$ | 0.358 | 0.524 | 0.413 | 0.256 | 0.482 | 0.563 | 0.641 | 0.240 |
| Clone No | 9 | 10 | 11 | 12 | 13 | 14 | 15 | 16 |
| $I_{420}$ | 0.269 | 0.462 | 0.324 | 0.650 | 0.470 | 0.584 | 0.419 | 0.581 |
| Clone No | 17 | 18 | 19 | 20 | 21 | 22 | 23 | 24 |
| $I_{420}$ | 0.265 | 0.741 | 0.623 | 0.491 | 0.489 | 0.612 | 0.444 | 0.523 |
| Clone No | 25 | 26 | 27 | 28 | 29 | 30 | 31 | 32 |
| $I_{420}$ | 0.223 | 0.551 | 0.542 | 0.469 | 0.378 | 0.380 | 0.264 | 0.701 |
| Clone No | 33 | 34 | 35 | 36 | 37 | 38 | 39 | 40 |
| $I_{420}$ | 0.610 | 0.528 | 0.290 | 0.300 | 0.314 | 0.268 | 0.701 | 0.467 |

TABLE 3-continued

Result of evaluation for aluminum oxide affinity by phage ELISA

| Clone No | 41 | 42 | 43 | 44 | 45 | 46 | 47 | 48 |
|---|---|---|---|---|---|---|---|---|
| $I_{420}$ | 0.345 | 0.516 | 0.410 | 0.432 | 0.489 | 0.236 | 0.521 | 0.584 |

| Clone No | 49 | 50 | 51 |
|---|---|---|---|
| $I_{420}$ | 0.642 | 0.513 | 0.498 |

The emission intensity was 0.001, which was observed when the phage was not mixed with a solution brought into contact with the Anodisc Membrane in Step 2 in the above phage ELISA measurement system (control).

The foregoing evaluation confirmed that any of the peptides which 51 obtained phage clones displayed had an affinity to aluminum oxide.

3) Amino Acid Sequence Showing Binding Ability to Aluminum Oxide

By comparison with the amino acid sequences of the random peptide display regions of each phage from the result of the DNA sequence analysis of the above phages, the amino acid sequences estimated to participate in an affinity to aluminum oxide were identified for the 51 phage clones sorted out. Table 4 shows the identified amino acid sequences showing affinities to aluminum oxide and their incidence.

TABLE 4

Identified amino acid sequence and Incidence

| Identified amino acid sequence | Number (A) | Incidence (A/51) |
|---|---|---|
| Val-Tyr-Ala-Asn-Gln-Thr-Pro-Pro-Ser-Lys-Ala-Arg (Sequence No: 1) | 11 | 0.22 |
| Gln-Ser-Ser-Ile-Thr-Thr-Arg-Asn-Pro-Phe-Met-Thr (Sequence No: 2) | 6 | 0.12 |
| Phe-Met-Asn-His-His-Pro-Asn-Ser-Gln-Gln-Tyr-His (Sequence No: 3) | 4 | 0.08 |
| Gln-Tyr-Thr-Ser-Ser-Gly-Ile-Ile-Thr-Ser-Ser-Ala (Sequence No: 4) | 3 | 0.06 |
| His-His-His-Pro-Glu-Asn-Leu-Asp-Ser-Thr-Phe-Gln (Sequence No: 5) | 3 | 0.06 |
| Gln-Pro-His-Met-His-Arg-Ser-Ser-His-Gln-Asp-Gly (Sequence No: 6) | 1 | 0.02 |
| Asn-Thr-Thr-Met-Gly-Pro-Met-Ser-Pro-His-Ser-Gln (Sequence No: 7) | 1 | 0.02 |
| Ala-Ala-His-Phe-Glu-Pro-Gln-Thr-Met-Pro-Met-Ile (Sequence No: 8) | 1 | 0.02 |
| Asp-His-Gln-Leu-His-Arg-Pro-Pro-His-Met-Met-Arg (Sequence No: 9) | 1 | 0.02 |
| Val-Ser-Arg-His-Gln-Ser-Trp-His-Pro-His-Asp-Leu (Sequence No: 10) | 1 | 0.02 |
| Met-Met-Gln-Arg-Asp-His-His-Gln-His-Asn-Ala-Gln (Sequence No: 11) | 1 | 0.02 |
| Val-Thr-Leu-His-Thr-Val-Asp-His-Ala-Pro-Gln-Asp (Sequence No: 12) | 1 | 0.02 |
| Ser-Val-Ser-Val-Gly-Met-Lys-Pro-Ser-Pro-Arg-Pro (Sequence No: 13) | 1 | 0.02 |
| His-Leu-Gln-Ser-Met-Lys-Pro-Arg-Thr-His-Val-Leu (Sequence No: 14) | 1 | 0.02 |
| Ile-Pro-Asn-Ala-Glu-Thr-Leu-Arg-Gln-Pro-Ala-Arg (Sequence No: 15) | 1 | 0.02 |
| Val-Gly-Val-Ile-Ser-Ser-Trp-His-Pro-His-Asp-Leu (Sequence No: 16) | 1 | 0.02 |
| Thr-Val-Pro-Ile-Tyr-Asn-Thr-Gly-Ile-Leu-Pro-Thr (Sequence No: 17) | 1 | 0.02 |
| Tyr-Thr-Met-His-His-Gly-Ser-Thr-Phe-Met-Arg-Arg (Sequence No: 18) | 1 | 0.02 |

TABLE 4-continued

Identified amino acid sequence and Incidence

| Identified amino acid sequence | Number (A) | Incidence (A/51) |
|---|---|---|
| Ser-Met-Met-His-Val-Asn-Ile-Arg-Leu-Gly-Ile-Leu (Sequence No: 19) | 1 | 0.02 |
| Ala-Pro-Met-His-His-Met-Lys-Ser-Leu-Tyr-Arg-Ala (Sequence No: 20) | 1 | 0.02 |
| Met-Met-Gln-Arg-Asp-His-His-Gln-His-Met-Arg-Arg (Sequence No: 21) | 1 | 0.02 |
| Met-Lys-Thr-His-His-Gly-Asn-Asn-Ala-Val-Phe-Leu (Sequence No: 22) | 1 | 0.02 |
| Leu-Glu-Pro-Leu-Pro-His-Thr-Pro-Arg-Met-Tyr-Ala (Sequence No: 23) | 1 | 0.02 |
| Gln-Leu-Tyr-Glu-Pro-Asp-Ser-Gly-Pro-Trp-Ala-Pro (Sequence No: 24) | 1 | 0.02 |
| Trp-Met-Thr-Lys-Met-Pro-Thr-Thr-His-Thr-Arg-Tyr (Sequence No: 25) | 1 | 0.02 |
| His-His-Pro-Met-Tyr-Ser-Met-Thr-Arg-Ala-Leu-Pro (Sequence No: 26) | 1 | 0.02 |
| Gly-Ser-Ala-His-Ser-Arg-Asn-Asp-Ala-Ala-Pro-Val (Sequence No: 27) | 1 | 0.02 |
| His-Ser-Pro-Leu-Met-Gln-Tyr-His-Met-Ser-Gly-Thr (Sequence No: 28) | 1 | 0.02 |
| Thr-Ala-His-Met-Thr-Met-Pro-Ser-Arg-Phe-Leu-Pro (Sequence No: 29) | 1 | 0.02 |

Example 2

Procurement of Cyclic Amino Acid Sequence Having Affinity to Aluminum Oxide

1) Selection of Aluminum Oxide Affinity Phage by Panning Technique (Step 1)

With 0.1% Tween-20/TBS buffer (50 mM tris-HCl, pH 7.5, 150 mM NaCl (hereinafter, referred as to TBST buffer)), $2 \times 10^{11}$ pfu of the PhD.-C7C phage display peptide library (NEW ENGLAND BIOLAB) was diluted to 0.5 ml to obtain a library suspension.

(Step 2)

For procurement of the amino acid sequence, 0.5 ml of the library suspension was added into one well of a flat-bottomed 24-well titer plate in which one aluminum oxide membrane (60 μm in thickness, 13 mm in diameter, pore size 0.2 μm, Anodisc Membrane, manufactured by Whatman) was placed, and left to stand at 25° C. for 30 minutes.

(Step 3)

The supernatant was discarded and the Anodisc Membrane was washed ten times with 2 ml of TBST buffer within the above well.

(Step 4)

After 0.5 ml of elution buffer (0.2M Glycine-HCl (pH 2.2), 1 mg/ml BSA) was added to the Anodisc Membrane which had been already washed, and then gently shaken for 10 minutes, the supernatant was transferred into another well in the microtiter plate. To the dispensed supernatant, 75 μl of 1 M tris-HCl (pH 9.1) was added for neutralization to obtain a phage eluted from the Anodisc Membrane.

(Step 5)

The eluted phage was infected with E. coli ER2537 (manufactured by NEW ENGLAND BIOLAB) at the early stage of logarithmic growth phase and amplified according to the following procedures.

Following infection, the E. coli was cultured at 37° C. for 4.5 hours. Subsequently, by centrifugation, the phage was separated from the E. coli and precipitated from the supernatant by polyethyleneglycol to be purified. The phage which had been amplified and purified was suspended into TBS buffer. The phage suspension was infected with the E. coli in appropriate dilution series, thereby measuring its titer.

(Step 6)

With respect to the affinity of the peptide which the above phage displayed to the Anodisc Membrane, for the phage contained in the suspension which had been primary screened, the screening procedure in Step 1 to Step 5 described above was additionally repeated three times. However, for the secondary and subsequent screening, the washing condition in Step 3 was made more rigorous by increasing the concentration of Tween-20 in TBST buffer utilized for washing to 0.5% (hereinafter, 0.5% TBST buffer) to sort out the phage showing a higher affinity to the Anodisc Membrane. In addition, for the tertiary (the second time) and subsequent screening, the phage separated from the Anodisc Membrane by washing in the above Step 3 was applied to the same procedure and its titer was measured. This separated phage would be used as control.

Table 5 shows the titer of the phages eluted from the Anodisc Membrane in each time of the primary screening to the forth screening.

TABLE 5

| | Titer of Phage eluted in each time of screenings | | | | |
|---|---|---|---|---|---|
| | Stock Solution (A) | Control Binding (B) | Anodisc Membrane Binding (C) | C/A | C/B |
| $1^{st}$ time | $2.0 \times 10^{11}$ | | $1.1 \times 10^2$ | $5.5 \times 10^{-10}$ | |
| $2^{nd}$ time | $2.0 \times 10^{11}$ | $1.2 \times 10^1$ | $4.6 \times 10^1$ | $2.3 \times 10^{-10}$ | 4 |
| $3^{rd}$ time | $2.0 \times 10^{11}$ | 3.0 | $1.5 \times 10^2$ | $7.5 \times 10^{-10}$ | $5.0 \times 10^1$ |
| $4^{th}$ time | $2.0 \times 10^{11}$ | 1.0 | $1.0 \times 10^3$ | $5.0 \times 10^{-9}$ | $1.0 \times 10^3$ |

(Units of A, B, and C = pfu/μl)

The phage eluted in the final screening step, which was sorted out in the above screening procedure, was cloned by its infection with a large excess of E. coli.

After each of the separated clones was infected with E. coli and amplified, ssDNA was prepared from the phages of each clones and the base sequence in the random region was decoded, thereby obtaining the phages of 11 clones having high affinities to the Anodisc Membrane.

The obtained phages of 11 clones were evaluated for affinity to aluminum oxide by the phage ELISA. In addition, the DNA sequences encoding each phage-displayed peptide portion were analyzed to determine the amino acid sequence of the peptide showing the binding ability to aluminum oxide.

2) Evaluation of Aluminum Oxide Affinity by Phage ELISA (Step 1)

For the phage suspensions of individual clones of the above 11 clones which had been sorted out from the PhD.-C7C phage display peptide library (NEW ENGLAND BIOLAB), $2 \times 10^{11}$ pfu equivalents of these suspensions were diluted with 0.5% TBST buffer to be brought to 0.5 ml.

(Step 2)

All of the phage suspensions were each added to one well in a flat-bottomed 24-well titer plate in which one Anodisc Membrane was placed, and were left to stand at 25° C. for 30 minutes.

(Step 3)

The supernatant was discarded and the Anodisc Membrane was washed ten times with 2 ml of 0.5% TBST buffer within the above well.

(Step 4)

To the Anodisc Membrane in the above well which had been already washed, 0.5 ml of an HRP binding anti-M13 antibody solution (1 μl of anti-M13 antibody (manufactured by NEW ENGLAND BIOLAB) was suspended in 10 ml of TBST)) was added, and the whole was gently shaken for 60 minutes. Subsequently, the supernatant was discarded and the mixture was washed 5 times by repeating the washing procedure with 2 ml of 0.5% TBST buffer.

(Step 5)

The treatment was applied to the phage bound on the Anodisc Membrane, in which this phage was reacted with the above HRP binding anti-M13 antibody. To the well in which this treated Anodisc Membrane was placed, 0.5 ml of Detection Reagent 1 (Amersham Pharmacia, #RPN2209) was added.

Furthermore, 0.5 ml of Detection. Reagent 2 (Amersham Pharmacia #RPN2209) was added thereto. After a lapse of three minutes, the emission intensity from luminol at 420 nm generated by the effect of the labeled enzyme HRP in the HRP binding anti-M13 antibody was measured.

The result of evaluation for each clone is shown in Table 6. $I_{420}$ indicates the emission intensity at 420 nm.

TABLE 6

| | Result of evaluation for aluminum oxide affinity by phage ELISA | | | | | | | | | | |
|---|---|---|---|---|---|---|---|---|---|---|---|
| Clone No | 1 | 2 | 3 | 4 | 5 | 6 | 7 | 8 | 9 | 10 | 11 |
| $I_{420}$ | 0.508 | 0.354 | 0.224 | 0.321 | 0.432 | 0.579 | 0.241 | 0.249 | 0.235 | 0.198 | 0.364 |

The emission intensity was 0.001, which was observed when the phage was not mixed with a solution brought into contact with the Anodisc Membrane in Step 2 in the above phage ELISA measurement system (control).

The foregoing evaluation confirmed that any of the peptides which 11 obtained phage clones displayed had an affinity to aluminum oxide.

3) Amino Acid Sequence Showing Binding Ability to Aluminum Oxide

By comparison with the amino acid sequences of the random peptide display regions of each phage from the result of the DNA sequence analysis of the phages, the amino acid sequences estimated to participate in an affinity to aluminum oxide were identified for the 51 phage clones sorted out. Table 7 shows the identified amino acid sequences showing affinities to aluminum oxide and their incidence.

TABLE 7

| Identified amino acid sequence and Incidence | | |
|---|---|---|
| Identified amino acid sequence | Number (A) | Incidence (A/15) |
| Ala-Cys-Pro-Pro-Thr-Gln-Ser-Arg-Tyr-Cys (Sequence No: 30) | 7 | 0.64 |

TABLE 7-continued

Identified amino acid sequence and Incidence

| Identified amino acid sequence | Number (A) | Incidence (A/15) |
|---|---|---|
| Ala-Cys-Asn-Gly-Met-Leu-Ala-Phe-Gln-Cys (Sequence No: 31) | 3 | 0.27 |
| Ala-Cys-Thr-Pro-Lys-Pro-Gly-Lys-His-Cys (Sequence No: 32) | 1 | 0.09 |

Example 3

Aluminum Oxide Affinity Peptide-Fused PHA Synthetic Enzyme

1) Production of DNA Fragment Encoding Aluminum Oxide Affinity Peptide-Fused PHA Synthetic Enzyme An *E. coli* expression vector expressing the anodisc membrane binding peptide-PHA synthetic enzyme fused product which was produced by fusing the amino acid sequence showing an affinity to the above anodisc membrane, Val-Tyr-Ala-Asn-Gln-Thr-Pro-Pro-Ser-Lys-Ala-Arg (SEQ ID NO: 1), to the N-terminal of the PHA synthetic enzyme through the linker sequence GGGS was constructed as follows.

The DNA fragment encoding this anodisc membrane binding peptide and the linker sequence portion was created as double-stranded DNA and ligated into the appropriate restriction cleavage sites (BamHI and SacI) of the pGEX-C1 plasmid for expressing the fused protein GST-YN2-C1. In this case, the ends of two synthesized oligonucleotides O1 (5'-GATCCGTTTATGCGAATCAGACTCCGC-CTTCTAAGGCGCGGGGTGGAGGTTCG GAGCT-3', SEQ ID NO: 47) and O2 (5'-CGAACCTCCACCCCGCGC-CTTAGAAGGCGGAGTCTGATTCGCATAAAC-3', SEQ ID NO: 4) were phosphorylated using T4 polynucleotide kinase (manufactured by Gibco) according to the manufacturer's instruction. Subsequently, two equimolar synthesized DNAs were mixed and heated at 80° C. for 5 minutes, followed by slow cooling to room temperature, thereby forming the double-stranded DNA fragment. The formed double-stranded DNA fragment was directly used for subsequent cloning.

2) Gene Transfer and Expression and Purification of Fused Product

The plasmid pGEX-C1 created in Reference Example 1 was digested with the restriction enzymes BamHI and SacI, into which in turn the above double-stranded DNA fragment was inserted. *E. coli* (JM109) was transformed with this vector to obtain a strain for expression. The confirmation of the introduction of the expression vector into each strain was carried out by determining the base sequence inserted between BamHI and SacI sites of the restriction enzymes by the sequencing of the plasmid DNA as a template which had been prepared using Miniprep (Wizard Minipreps DNA. Purification Systems, manufactured by PROMEGA), with pGEX 5' Sequencing Primer (manufactured by Amersham Pharmacia Biotech). After the resulting strain for expression was pre-cultured overnight in 10 ml of LB-Amp medium, 0.1 ml of that cultured product was added to 10 ml of LB-Amp medium and cultured while being stirred at 37° C. for 3 hours at 170 rpm. IPTG (final concentration 1 mM) was then added thereto and the culture was continued at 37° C. for 4-12 hours.

IPTG-derived *E. coli* was harvested (8000×g, 2 min., 4° C.) and resuspended into 1/10 volume of 4° C. PBS. The fungus cells was ruptured by freeze-thaw and sonication and centrifuged (8000×g, 10 min., 4° C.) to remove solid impurities. The expressed protein of interest was confirmed to exist in the supernatant by SDS-PAGE. Subsequently, from the supernatant, the GST-fused protein which had been derived and expressed was purified with Glutathion Sepharose 4B beads (manufactured by Amersham Pharmacia Biotech).

It is noted that the GST-fused protein which is derived and expressed is the fused protein GST-A01-GS-YN2-C1 into which the peptide chain is inserted where the amino acid sequence of the above SEQ ID NO: 1 and the linker sequence GGGS are coupled between the C-terminal of the GST protein as a fusion partner and the N-terminal of the PHA synthetic enzyme protein YN2-C1.

The glutathione sepharose used was previously treated for suppressing nonspecific absorption. That is, after the glutathione sepharose was washed (8000×g, 1 min., 4° C.) three times in the equal volume of PBS, the equal volume of 4% BSA-containing PBS was added thereto and the whole was treated at 4° C. for 1 hour. Following the treatment, the glutathione sepharose was washed twice in the equal volume of PBS and resuspended into ½ volume of PBS. 40 μL of the glutathione sepharose pretreated was added to 1 mL of a cell-free extract (supernatant) and the whole was gently stirred at 4° C. By this stirring, the fused protein GST-A01-GS-YN2-C1 was absorbed to the glutathione sepharose.

After the absorption, the glutathione sepharose was collected by centrifugation (8000×g, 1 min., 4° C.) and washed three times in 400 μl of PBS. Subsequently, 40 μl of 10 mM glutathione was added and the whole was stirred at 4° C. for 1 hour to elute the fused protein which was absorbed. The supernatant containing the fused protein was collected by centrifugation (8000×g, 2 min., 4° C.) and dialyzed against PBS to purify the GST-fused protein. Following the purification, SDS-PAGE showed that the purified product showed a single band.

With PreScission protease (Amersham Pharmacia Biotech, 5 U), 500 μg of each GST-fused protein was digested and the fusion partner GST portion at the N-terminal was separated by cleavage. This solution was loaded onto a glutathione sepharose column to remove protease and GST. The flow-through fraction of the glutathione sepharose column was further loaded onto the Sephadex G200 column equilibrated with PBS to obtain, as a final purified product, the peptide-fused protein A01-YN2-C1. SDS-PAGE showed that the expressed protein A01-GS-YN2-C1 which had been already finally purified showed a single band.

The enzymatic activity of the resulting expressed protein A01-GS-YN2-C1 which had been already finally purified was measured by the method described in the above Reference Example 2. Moreover, the concentration of the protein in the sample was measured with the Micro BCA Protein Quantification Reagent Kit (manufactured by Pierce Chemical). The enzymatic activity of the sample was 1.9 U/ml with the specific activity of 4.0 U/mg protein. The enzymatic solution which had been already finally purified was concentrated using a biological solution sample concentrating agent (Mizubutorikun AB-1100, manufactured by ATTO Co., LTD.) to obtain 10 U/ml of the purified enzymatic solution.

3) Affinity Evaluation for Aluminum Oxide Particle of Aluminum Oxide Affinity Peptide-Fused Protein The aluminum oxide particle AW40-74 (manufactured by Micron) was suspended into 0.1% Tween-20/TBS buffer so as to be 0.5% (w/v). In a centrifuge tube made from Teflon, 10 ml of this suspension was placed and 0.5 U equivalents of the peptide-fused PHA synthetic enzyme A01-GS-YN2-C1 prepared in Example 2 or the PHA synthetic enzyme YN2-C1 prepared in Reference Example 2 was added thereto and the whole was shaken at room temperature for 30 minutes. By the centrifugation procedure (10,000×g, 4° C., 10 min.), the AW40-74 particle as a precipitate was collected and separated from the supernatant containing the enzyme protein which had not been bound to the AW40-74. The AW40-74 which had been collected as a precipitate fraction was suspended again into TBS buffer containing 0.1% Tween-20 and centrifuged. The AW40-74 was washed by repeating the procedure of collecting the precipitate fraction. Table 8 shows the result of the enzymatic activity of the washed AW40-74 suspension measured by the measuring method described in the above Reference Example 2.

TABLE 8

Enzymatic activity of each PHA synthetic enzyme protein bound on aluminum oxide particle

| PHA synthetic enzyme complex | Enzymatic activity (U) |
|---|---|
| A 01-GS-YN2-C1 | 0.11 |
| YN 2-C1 | 0.01 |

Similarly, for thirty-one aluminum oxide affinity sequences shown in SEQ ID NO: 2 to SEQ ID NO: 32, the aluminum oxide particle-PHA synthetic enzyme complexes: A02-GS-YN2-C1 to A32-GS-YN2-C1 were prepared in the same manner as in Example 2 using synthesized oligonucleotides shown in SEQ ID NO: 49 to SEQ ID NO: 110, and the enzymatic activity of each PHA synthetic enzyme bound to the aluminum oxide particle was measured in the same way in order to evaluating the binding ability to the aluminum oxide particle. The result of measurement is shown in Table 9.

TABLE 9

Enzymatic activity of each PHA synthetic enzyme protein bound on aluminum oxide particle

| PHA synthetic enzyme | Enzymatic activity (U) |
|---|---|
| A02-GS-YN2-C1 | 0.09 |
| A03-GS-YN2-C1 | 0.08 |
| A04-GS-YN2-C1 | 0.08 |
| A05-GS-YN2-C1 | 0.08 |
| A06-GS-YN2-C1 | 0.09 |
| A07-GS-YN2-C1 | 0.07 |
| A08-GS-YN2-C1 | 0.06 |
| A09-GS-YN2-C1 | 0.07 |
| A10-GS-YN2-C1 | 0.08 |
| A11-GS-YN2-C1 | 0.07 |
| A12-GS-YN2-C1 | 0.07 |
| A13-GS-YN2-C1 | 0.06 |

TABLE 9-continued

Enzymatic activity of each PHA synthetic enzyme protein bound on aluminum oxide particle

| PHA synthetic enzyme | Enzymatic activity (U) |
|---|---|
| A14-GS-YN2-C1 | 0.08 |
| A15-GS-YN2-C1 | 0.08 |
| A16-GS-YN2-C1 | 0.07 |
| A17-GS-YN2-C1 | 0.06 |
| A18-GS-YN2-C1 | 0.06 |
| A19-GS-YN2-C1 | 0.07 |
| A20-GS-YN2-C1 | 0.09 |
| A21-GS-YN2-C1 | 0.08 |
| A22-GS-YN2-C1 | 0.06 |
| A23-GS-YN2-C1 | 0.08 |
| A24-GS-YN2-C1 | 0.05 |
| A25-GS-YN2-C1 | 0.06 |
| A26-GS-YN2-C1 | 0.07 |
| A27-GS-YN2-C1 | 0.07 |
| A28-GS-YN2-C1 | 0.07 |
| A29-GS-YN2-C1 | 0.06 |
| A30-GS-YN2-C1 | 0.10 |
| A31-GS-YN2-C1 | 0.08 |
| A32-GS-YN2-C1 | 0.05 |
| YN2-C1 | 0.01 |

Comparison to the control enzyme protein YN2-C1 confirmed that the enzyme proteins A01-GS-YN2-C1 and A30-GS-YN2-C1 fusing, at the N-terminal, the peptide chain of the amino acid sequence having the binding ability to aluminum oxide were observed to have higher enzymatic activity and that the enzyme protein was allowed to be effectively immobilized on the surface of the substrate composed of the aluminum oxide through the peptide chain of the amino acid sequence having the binding ability to the aluminum oxide, which was fused at the N-terminal.

Example 4

Production of Aluminum Oxide Affinity Peptide-Fused Horseradish Peroxidase (HPR)

An *E. coli* expression vector expressing the anodisc membrane binding peptide-HPR fused protein which is produced by fusing the amino acid sequence showing an affinity to the anodisc membrane, Val-Tyr-Ala-Asn-Gln-Thr-Pro-Pro-Ser-Lys-Ala-Arg (SEQ ID NO: 1), to the N-terminal of the HPR through the linker sequence GGGS is constructed as follows.

1) Production of DNA Fragment Encoding Aluminum Oxide Affinity Peptide-Fused HPR and Preparation of Primer.

At first; the double-stranded DNA encoding the above anodisc membrane binding peptide-fused protein-linker sequence (GGGS)-HPR (A01-GS-HPR) (SEQ ID NO: 111) is synthesized.

This example utilized the procedure by Fujimoto et al., known as a synthetic method of long-chain DNA (Hideya Fujimoto, "the Production of Synthetic Gene", Plant Cell Technology Series 7 PCR Experiment Protocol for Plant, Shujunsha, pp. 95-100 (1997)). The principle of this method is that the oligonucleotide primers on the order of 120 mer are created to have the overlaps on the order of 20 mer at the 3' end, and the deficient portion is extended utilizing the overlap regions of the oligonucleotide primers and further amplified by performing PCR using the primers at both ends. This procedure is successively repeated to synthesize long-chain DNA of interest.

Figure 4:
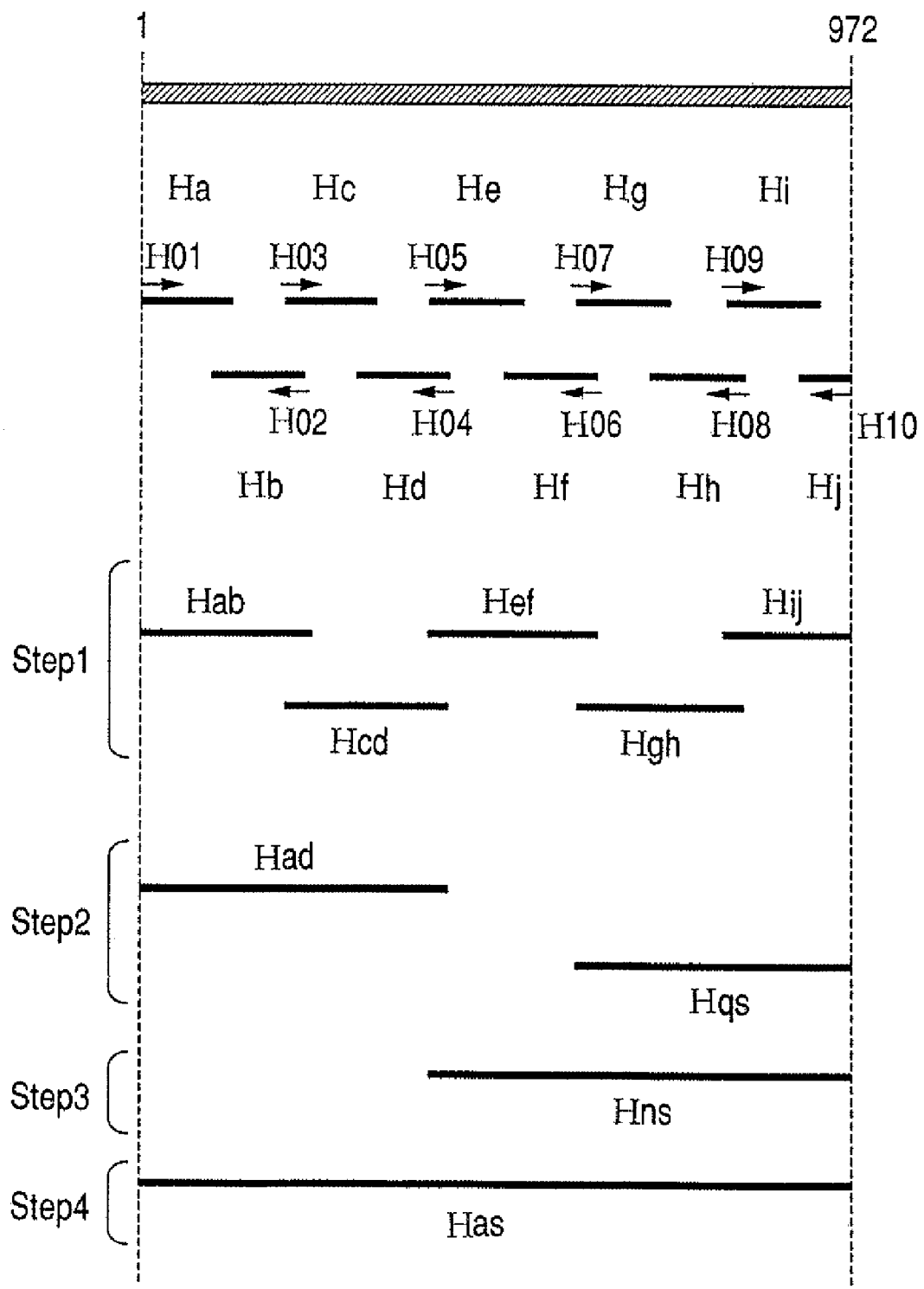
FIG. 4 is a diagram showing primer configurations used for synthesis of a long-chain DNA by PCR used in Example 4 and synthetic steps (Steps 1 to 4)

A series of overlap PCR method is successively carried out according to FIG. 4. The DNA sequences of twenty various primers (Ha, H01, Hb, H02, Hc, H03, Hd, H04, He, H05, Hf, H06, Hg, H07, Hh, H08, H1, H09, Hj, H10) shown in FIG. 4 are shown in SEQ ID NOs. 112-131, respectively. After the completion of extension reaction in Step 4 shown in FIG. 4, it is confirmed whether the full-length A01-GS-HRP gene has been synthesized.

Oligonucleotide (SEQ ID NO: 132) which is an upstream primer and oligonucleotide (SEQ ID NO: 133) which is a downstream primer, relative to the A01-GS-HRP gene, are designed and synthesized, respectively. Those two oligonucleotides are used as a primer pair and PCR amplification is carried out using the A01-GS-HRP gene as a template to obtain, as an amplified product, DNA containing the full-length PHA synthetic enzyme gene having the BamHI restriction site upstream and the XhoI restriction site downstream (LA-PCR Kit; Takara Shuzo).

Upstream Primer (SEQ ID NO: 132):

```
5'-AGTCGGATCC GTTTATGCGA ATCAGACTCC GCCTTCTAAG

GCGCGGGGTG GAGGTTCG-3'
```

Downstream Primer (SEQ ID NO: 133):

```
5'-AGGCCTCGAG AGAGTTGGAG TTCACCACCC TACA-3'
```

2) Gene Transfer and Expression of Fused Product

Ligation into the appropriate restriction cleavage sites (BamHI and SacI) of the pGEX-C1 plasmid for expressing the above fused protein GST-YN2-C1 is performed.

The plasmid pGEX-C1 made in Reference Example 2 and the PCR product obtained as above are digested with the restriction enzymes BamHI and XhoI.

Next, the above fragments are bound using T4 ligase.

By using this ligation solution, transformation into 40 µl of the E. coli solution (JM109 Competent Cell) is performed by the heat shock method. To the E. coli solution where transformation has been made, 750 µL of LB is further added and cultured while being shaken at 37° C. for 1 hour. Subsequently, the above cultured solution is inoculated over LB/amp. Plate and left to stand overnight at 37° C.

The confirmation of the base sequence of the insert introduced into the expression vector is carried out by determining the base sequence inserted between BamHI and XhoI sites of the restriction enzymes by the sequencing of the plasmid DNA as a template which has been prepared using Miniprep (Wizard Minipreps DNA Purification Systems, manufactured by PROMEGA), with pGEX 5' Sequencing Primer (manufactured by Amersham Pharmacia Biotech).

The resulting expression vector for the GST-A01-GS-HPR-fused protein is transformed into the BL21 (DE3) competent cell by the heat shock method. After the resulting strain for expression is pre-cultured overnight in 10 ml of LB-Amp medium, 5 ml of that cultured product is added to 1.5 L of LB-Amp medium and cultured while being stirred at 28° C. for 15 hours at 150 rpm. IPTG (final concentration 1 mM) is then added thereto and the culture is continued at 37° C. for 12 hours.

IPTG-derived E. coli is harvested (8000×g, 30 min., 4° C.) and resuspended into 1/10 volume of 4° C. PBS. The fungus cells is ruptured by freeze-thaw and sonication and centrifuged (8000×g, 10 min., 4° C.) to remove solid impurities. The expressed protein of interest is confirmed to exist in the supernatant by SDS-PAGE.

3) Purification of Fused Protein

From the supernatant, the GST-fused protein which has been derived and expressed is purified with Glutathion Sepharose 4B beads (manufactured by Amersham Pharmacia Biotech).

It is noted that the GST-fused protein which is derived and expressed is the fused protein GST-A01-GS-HPR into which the peptide chain is inserted where the amino acid sequence of the above SEQ ID NO: 1 and the linker sequence GGGS are coupled between the C-terminal of the GST protein as a fusion partner and the N-terminal of the HRP protein.

The glutathione sepharose used is previously treated for suppressing nonspecific absorption. That is, after the glutathione sepharose is washed (8000×g, 10 min., 4° C.) three times in the equal volume of PBS, the equal volume of 4% BSA-containing PBS is added thereto and the whole is treated at 4° C. for 1 hour. Following treatment, the glutathione sepharose is washed twice in the equal volume of PBS and resuspended into ½ volume of PBS. 400 µL of the glutathione sepharose pretreated is added to 10 mL of a cell-free extract (supernatant) and the whole is gently stirred at 4° C. By this stirring, the fused protein GST-A01-GS-HRP is absorbed to the glutathione sepharose.

After the absorption, the glutathione sepharose is collected by centrifugation (8000×g, 10 min., 4° C.) and washed three times in 5 ml of PBS. Subsequently, 40 µl of 10 mM glutathione is added and the whole is stirred at 4° C. for 1 hour to elute the fused protein which has been absorbed. The supernatant containing the fused protein is collected by centrifugation (8000×g, 3 min., 4° C.) and dialyzed against PBS to purify the GST-fused protein. Following the purification, a single band is shown by SDS-PAGE.

With PreScission protease (Amersham Pharmacia Biotech, 5U), 500 µg of each GST-fused protein is digested and the fusion partner GST portion at the N-terminal is separated by cleavage. This solution is loaded onto a glutathione sepharose column to remove protease and GST. The flow-through fraction of the glutathione sepharose column is further loaded onto the Sephadex G200 column equilibrated with PBS to obtain, as a final purified product, the peptide-fused protein A01-GS-HRP/PBS.

4) Biosensor Using Affinity Peptide-Fused HRP

The resulting A01-GS-HRP is immobilized onto the aluminum oxide-deposited platinum substrate by the following method.

The above substrate is dipped into the A01-GS-HPR/PBS obtained as above and stirred overnight at room temperature. Subsequently, the aluminum oxide substrate is pulled out of the solution and dipped into 0.05% Tween 20/phosphate aqueous solution, followed by washing the front and back of the plate while stirring for 3 min (100 rpm). This procedure is repeated three times. This results in the HRP-immobilized substrate.

The resulting HRP-immobilized substrate as a working electrode, as well as platinum as a counter electrode and silver/silver chloride as a reference electrode are dipped into the container filled with 30 mM of potassium iodide/phosphate aqueous solution (pH 7.4) to create the enzymatic electrode measurement system.

Next, after the potential E1=−300 mV vs. Ag/AgCl is applied to the working electrode for 40 seconds, the potential at the working electrode is changed to 0 mV vs. Ag/AgCl and maintained for 240-320 seconds, followed by stepping the potential to −300 mV vs. Ag/AgCl. As such, the potential step between 0 mV vs. Ag/AgCl and −300 mV vs. Ag/AgCl is repeated until the current behavior between the working electrode and the counter electrode is allowed to have reproducibility. Subsequently, a hydrogen peroxide solution is added such that the final concentration is brought to 10 µM, and the value of the current of the HRP-immobilized electrode at this point is measured. Stirring is carried out for 5 seconds every addition of the hydrogen peroxide solution and after a lapse of 30-40 seconds the potential step proceeds from 0 mV to E1=−300 mV vs. Ag/AgCl. Next, the potential is stepped to E2=0 mV vs. Ag/AgCl and at this point the current response which has flowed between the working electrode and the counter electrode is monitored.

Then, current responses at final concentrations of the hydrogen peroxide solution of 50, 100, and 500 µM are monitored in the same way. As a result, increase in current of the HRP-immobilized electrode proportional to the amount of hydrogen peroxide added is observed.

The above hydrogen peroxide electrode is expected to function as a hydrogen peroxide sensor.

Example 5

Production of Aluminum Oxide Affinity Peptide-Fused GroEL

An *E. coli* expression vector expressing the anodisc membrane binding peptide-GroEL fused protein which is produced by fusing the amino acid sequence showing an affinity to the anodisc membrane, Val-Tyr-Ala-Asn-Gln-Thr-Pro-Pro-Ser-Lys-Ala-Arg (SEQ ID NO: 1), to the N-terminal of the GroEL through the linker sequence GGGS is constructed as follows.

1) Production of DNA Fragment Encoding Aluminum Oxide Affinity Peptide-Fused GroEL and Preparation of Primer At first, DNA encoding the above anodisc membrane binding peptide-fused protein-linker sequence GGGS-GroEL (A01-GS-GroEL) (SEQ ID NO: 134) is synthesized.

Figure 5:
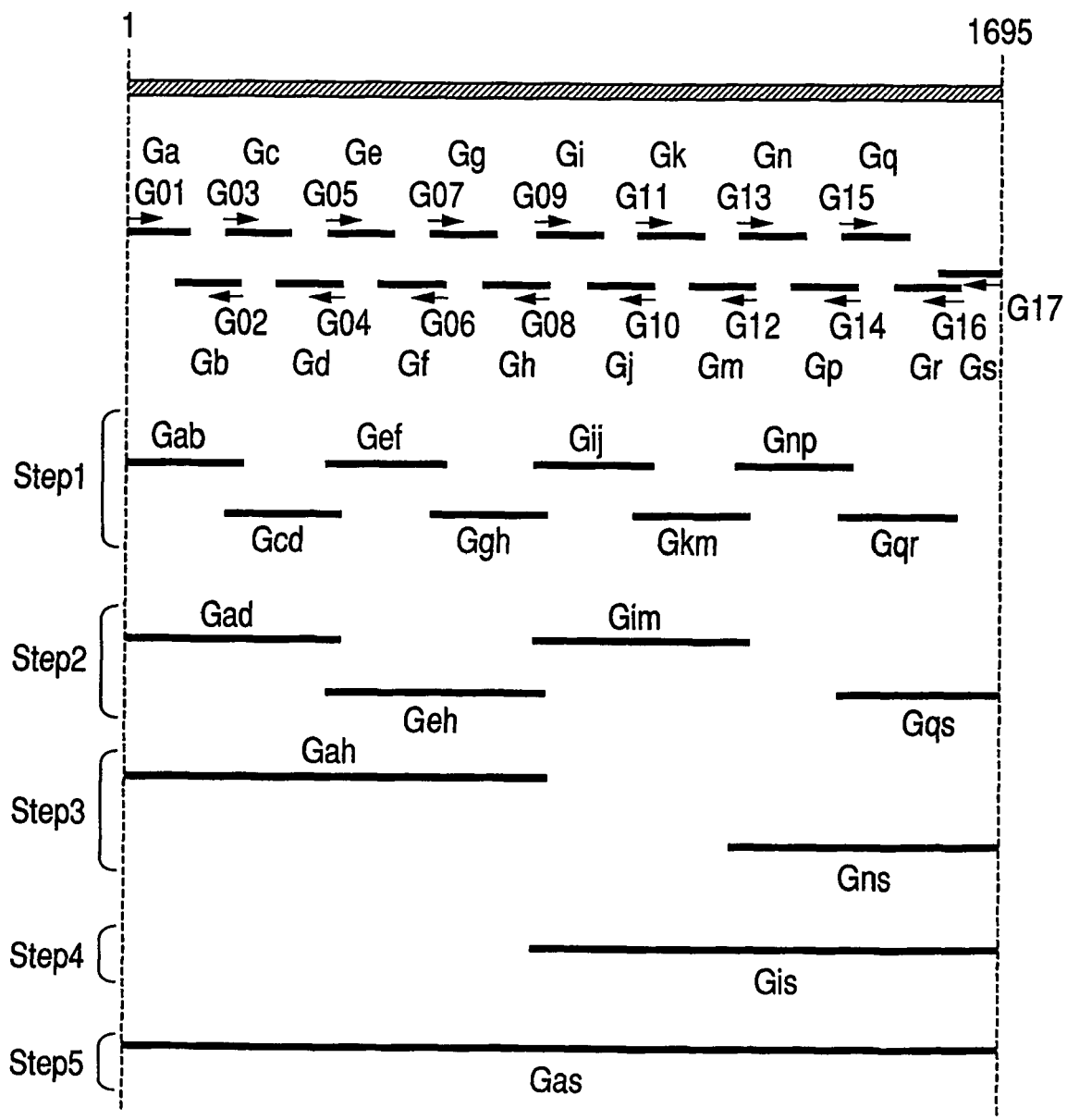
FIG. 5 is a diagram showing the primer configurations used for synthesis of a long-chain DNA by PCR used in Example 5 and synthetic steps (Steps 1 to 5).

A series of overlap PCR method is successively carried out according to FIG. 5 in the same manner as in Example 5-1). The DNA sequences of twenty in total of various primers (Ga, G01, Gb, G02, Gc, G03, Gd, G04, Ge, G05, Gf, G06, Gg, G07, Gh, G08, G1, G09, Gj, G10, Gk, G11, Gm, G12, Gn, G13, Gp, G14, Gq, G15, Gr, G16, Gs, G17) shown in FIG. 5 are shown in SEQ ID NOs. 135-168, respectively. After the completion of extension reaction in Step 5 shown in FIG. 5, it is confirmed whether the full-length A01-GS-GroEL gene has been synthesized.

Oligonucleotide (SEQ ID NO: 132) which is an upstream primer and oligonucleotide (SEQ ID NO: 169) which is a downstream primer, relative to the A01-GS-GroEL, are designed and synthesized, respectively. Those two oligonucleotides are used as a primer pair and PCR amplification is carried out using the A01-GS-GroEL gene as a template to obtain, as an amplified product, DNA containing the full-length PHA synthetic enzyme gene having the BamHI restriction site upstream and the XhoI restriction site downstream (LA-PCR Kit; Takara Shuzo).

Upstream Primer (SEQ ID NO: 132):

```
5'-AGTCGGATCC GTTTATGCGA ATCAGACTCC GCCTTCTAAG
GCGCGGGGTG GAGGTTCG-3'
```

Downstream Primer (SEQ ID NO: 169):

```
5'-AGGCCTCGAG TTACATCATG CCGCCCATGC CAC-3'
```

2) Gene Transfer and Expression and Purification of Fused Product

After the same procedure is performed as in Example 5-2) using the synthesized base sequence and the above primers, from the supernatant, the GST-fused protein which has been derived and expressed is purified with Glutathion Sepharose 4B beads (manufactured by Amersham Pharmacia Biotech).

It is noted that the GST-fused protein which is derived and expressed is the fused protein GST-A01-GS-GroEL into which the peptide chain is inserted where the amino acid sequence of the above SEQ ID NO: 1 and the linker sequence GS are coupled between the C-terminal of the GST protein as a fusion partner and the N-terminal of the GroEL protein.

The glutathione sepharose used is previously treated for suppressing nonspecific absorption. That is, after the glutathione sepharose is washed (8000×g, 10 min., 4° C.) three times in the equal volume of PBS, the equal volume of 4% BSA-containing PBS is added thereto and the whole is treated at 4° C. for 1 hour. Following the treatment, the glutathione sepharose is washed twice in the equal volume of PBS and resuspended into ½ volume of PBS. To 10 mL of a cell-free extract (supernatant), 400 µL of the glutathione sepharose pretreated is added and the whole is gently stirred at 4° C. By this stirring, the fused protein GST-A01-GS-GroEL is absorbed to the glutathione sepharose.

After the absorption, the glutathione sepharose is collected by centrifugation (8000×g, 10 min., 4° C.) and washed three times in 5 ml of PBS. Subsequently, 40 µl of 10 mM glutathione is added and the whole is stirred at 4° C. for 1 hour to elute the fused protein which has been absorbed. The supernatant containing the fused protein is collected by centrifugation (8000×g, 3 min., 4° C.) and dialyzed against PBS to purify the GST-fused protein. Following the purification, a single band is shown by SDS-PAGE.

With PreScission protease (Amersham Pharmacia Biotech, 5U), 500 µg of each GST-fused protein is digested and the fusion partner GST portion at the N-terminal is separated by cleavage. This solution is loaded onto a glutathione sepharose column to remove protease and GST. The flow-through fraction of the glutathione sepharose column is further loaded onto the Sephadex G200 column equilibrated with PBS to obtain, as a final purified product, the peptide-fused protein A01-GS-GroEL/PBS.

3) Enzyme Activated Filter Using Affinity Peptide-Fused GroEL

The resulting A01-GS-GroEL and aluminum oxide nano-holes are immobilized by the following method.

Into an aluminum oxide nanoholes-embedded syringe filter (membrane-60 µm in thickness, 10 mm in diameter, pore size 0.2 µm, trade name: Anotop 10 Syringe Filter, manufactured by Whatman), 10 ml of the A01-GS-GroEL 1 µl-PBS solution obtained as above is injected at a speed of 0.1 ml/min. Subsequently, 30 ml of 0.05% Tween 20/phosphate aqueous solution is injected at a speed of 0.5 ml/min, followed by washing. This results in the filter which optimizes the stereo structure of a protein.

On the other hand, Yeast Enolase (manufactured by Oriented Yeast Corporation) which is denatured in 4 M guanidine hydrochloride to decrease activity is added into the renaturing buffer (10 mM Mg($CH_3COO$)$_2$, mM KCl, 5 mM ATP, 50 mM tris-Cl, pH 7.8) such that the final concentration is brought to 15 µg/ml. The mixture is then injected into the above filter at a speed of 2 µl/min to react.

The activity of the enolase after the completion of reaction is observed to have the ability of activity recovery, when 0.04 ml of the enolase solution is mixed with 0.96 ml of the substrate solution (50 mM tris-Cl, pH 7.8, 1 mM $MgCl_2$, 1 mM 2-PGA (2-phosphoglycericacid) and increase in the absorbance at 240 nm by the production of phosphoenol pyruvate at 37° C. is measured as a function of time. Comparing the enolase activity ability with GroEL composed of the subunits lacking the aluminum oxide affinity peptide, 95% of the ability of activity recovery is observed. For comparison, the ability of activity recovery of the GroEL in which the histidine tag remains added to all the subunits is examined and found to be 80% so that improvement can be confirmed.

Example 6

Aluminum Oxide Affinity Peptide Analog-Fused PHA Synthetic Enzyme

In order to confirm that the altered amino acid sequences having the deletion, substitution, or addition of the amino acid of the aluminum oxide affinity peptide, or the amino acid sequence in combination of two of them has an affinity, E. Coli expression vectors expressing the anodisc membrane-binding peptide-PHA synthetic enzyme fused products are constructed as follows, which are produced by fusing, to the N-terminal of the PHA synthetic enzyme through the linker sequence GGGS, the sequence having the deletion of 4 residues of the amino acid: Tyr-Ala-Gln-Thr-Pro-Pro-Ser-Arg (SEQ ID NO: 170), the sequence having the substitution of 4 residues of the amino acid: Leu-Tyr-Ala-Gln-Gln-Thr-Pro-Pro-Ser-Arg-Ser-Arg (SEQ ID NO: 171), the sequence having the addition of 4 residues of the amino acid: Val-Tyr-Ala-Asn-Gln-Thr-Pro-Pro-Ser-Arg-Ala-Arg-Ala-Lys-Ala-Arg (SEQ ID NO: 172), and the sequence combining SEQ ID NO: 1 and SEQ ID NO: 170: Val-Tyr-Ala-Asn-Gln-Thr-Pro-Pro-Ser-Lys-Ala-Arg-Tyr-Ala-Gln-Thr-Pro-Pro-Ser-Arg (SEQ ID NO: 173), respectively, relative to the affinity peptide of the peptide-fused protein A01-GS-YN2-C1 having a high affinity as indicated in Example 3, Val-Tyr-Ala-Asn-Gln-Thr-Pro-Pro-Ser-Lys-Ala-Arg (SEQ ID NO: 1).

The DNA fragment encoding this anodisc membrane binding peptide and the linker sequence portion is created as double-stranded DNA and ligated into the appropriate restriction cleavage sites (BamHI and SacI) of the pGEX-C1 plasmid for expressing the fused protein GST-YN2-C1. In this case, the ends of the synthesized oligonucleotides of SEQ ID NO: 174 to SEQ ID NO: 181 has been phosphorylated using T4 polynucleotide kinase (manufactured by Gibco) according to the manufacturer's instruction. Subsequently, two equimolar synthesized DNAs are mixed and heated at 80° C. for 5 minutes, followed by slow cooling to room temperature, thereby forming the double-stranded DNA fragment. The formed double-stranded DNA fragment is directly used for subsequent cloning. After that, gene transfer and the expression and purification of the fused product are carried out in the same manner as in Example 3-2 to obtain 10 U/ml of purified solutions of A01M-GS-YN2-C1 in which 4 residues of the amino acid are deleted from A01-GS-YN2-C1, A01S-GS-YN2-C1 in which 4 residues of the amino acid are substituted, A01P-GS-YN2-C1 in which 4 residues of the amino acid are added, and A01W-GS-YN2-C1 in which SEQ ID NO: 1 and SEQ ID NO: 170 are combined.

In addition, the affinity evaluation for the resulting peptide-fused proteins is carried out in the same manner as in Example 3-3 and the enzymatic activity is measured. The result is shown in Table 10.

TABLE 10

Enzymatic activity of each PHA synthetic enzyme protein bound on aluminum oxide particle

| PHA synthetic enzyme complex | Enzymatic activity (U) |
| --- | --- |
| A01-GS-YN2-C1 | 0.11 |
| A01M-GS-YN2-C1 | 0.10 |
| A01S-GS-YN2-C1 | 0.08 |
| A01P-GS-YN2-C1 | 0.07 |
| A01W-GS-YN2-C1 | 0.12 |
| YN2-C1 | 0.01 |

As compared to the control enzyme protein YN2-C1, similarly to the enzyme protein A01-GS-YN2-C1 fusing, at the N-terminal, the peptide chain of the amino acid sequence having the binding ability to aluminum oxide, A01M-GS-YN2-C1, A01S-GS-YN2-C1, A01P-GS-YN2-C1, and A01W-GS-YN2-C1 are observed to have higher enzymatic activity. This showed that, of the amino acid sequences of the above aluminum oxide affinity peptide, the enzyme protein in which any of the altered amino acid sequences having the deletion, substitution, or addition of a few amino acids or the amino acid sequence in combination of two or more of them had been fused was allowed to be effectively immobilized on the surface of the substrate composed of aluminum oxide through the N-terminal where they were located.

INDUSTRIAL APPLICABILITY

In the present invention, an organic substance-immobilized structure, for example, a substrate having a surface on which a biological substance is immobilized, is provided with an aluminum oxide layer as the substrate's surface on which the substance is to be immobilized. In the organic substance to be immobilized, on the other hand, the biological substance itself is provided as a functional domain, which is coupled with a binding domain having an ability to bind to the aluminum oxide layer. Thus, the biological substance portion provided as the functional domain can be allowed to be selectively immobilized by means of the binding ability to the aluminum oxide through the binding domain being coupled without directly contacting with the surface of the substrate. The biological substance being immobilized on the surface of the substrate through the independently-formed binding domain is free from any chemical reaction that affects the functions of the biological substance because of no influence of immobilization on the inherent functions and no reagent used for the immobilization. Therefore, in the biological substance-immobilized substrate, which can be obtained by applying the present invention, the biological substance being immobilized receives as small influence on its functions as possible, while being immobilized on the surface of the substrate effectively with high orientation.

In other words, the present invention is applicable to a technique of enhancing performance of a product by the utilization of a function of various biological substances, such as a biosensor or bioreactor in which the organic substance such as the biological substance is immobilized on the surface of the substrate, and various biological functions of the organic substance are utilized.

This application claims priority from Japanese Patent Application No. 2004-016858 filed Jan. 26, 2004, which is hereby incorporated by reference herein.

The invention claimed is:
1. A method of manufacturing a structure which comprises a protein and a substrate comprising the steps of:
 preparing a substrate having a surface at least part of which contains aluminum oxide;
 preparing a protein comprising the amino acid sequence of SEQ ID NO: 1 and having an ability to bind to the aluminum oxide; and
 bringing the protein into contact with the surface of the substrate to obtain the structure which comprises the protein and the substrate.

* * * * *

SEQUENCE LISTING

<160> NUMBER OF SEQ ID NOS: 181

<210> SEQ ID NO 1
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 1

Val Tyr Ala Asn Gln Thr Pro Pro Ser Lys Ala Arg
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 2

Gln Ser Ser Ile Thr Thr Arg Asn Pro Phe Met Thr
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 3

Phe Met Asn His His Pro Asn Ser Gln Gln Tyr His
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 4

Gln Tyr Thr Ser Ser Gly Ile Ile Thr Ser Ser Ala
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 5

His His His Pro Glu Asn Leu Asp Ser Thr Phe Gln
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 6

```
Gln Pro His Met His Arg Ser Ser His Gln Asp Gly
  1               5                  10
```

```
<210> SEQ ID NO 7
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 7

Asn Thr Thr Met Gly Pro Met Ser Pro His Ser Gln
  1               5                  10
```

```
<210> SEQ ID NO 8
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 8

Ala Ala His Phe Glu Pro Gln Thr Met Pro Met Ile
  1               5                  10
```

```
<210> SEQ ID NO 9
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 9

Asp His Gln Leu His Arg Pro Pro His Met Met Arg
  1               5                  10
```

```
<210> SEQ ID NO 10
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 10

Val Ser Arg His Gln Ser Trp His Pro His Asp Leu
  1               5                  10
```

```
<210> SEQ ID NO 11
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 11

Met Met Gln Arg Asp His His Gln His Asn Ala Gln
  1               5                  10
```

```
<210> SEQ ID NO 12
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 12

Val Thr Leu His Thr Val Asp His Ala Pro Gln Asp
```

```
                1               5                   10

<210> SEQ ID NO 13
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 13

Ser Val Ser Val Gly Met Lys Pro Ser Pro Arg Pro
 1               5                   10

<210> SEQ ID NO 14
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 14

His Leu Gln Ser Met Lys Pro Arg Thr His Val Leu
 1               5                   10

<210> SEQ ID NO 15
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 15

Ile Pro Asn Ala Glu Thr Leu Arg Gln Pro Ala Arg
 1               5                   10

<210> SEQ ID NO 16
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 16

Val Gly Val Ile Ser Ser Trp His Pro His Asp Leu
 1               5                   10

<210> SEQ ID NO 17
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 17

Thr Val Pro Ile Tyr Asn Thr Gly Ile Leu Pro Thr
 1               5                   10

<210> SEQ ID NO 18
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 18

Tyr Thr Met His His Gly Ser Thr Phe Met Arg Arg
 1               5                   10
```

```
<210> SEQ ID NO 19
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 19

Ser Met Met His Val Asn Ile Arg Leu Gly Ile Leu
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 20

Ala Pro Met His His Met Lys Ser Leu Tyr Arg Ala
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 21

Met Met Gln Arg Asp His His Gln His Met Arg Arg
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 22

Met Lys Thr His His Gly Asn Asn Ala Val Phe Leu
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 23

Leu Glu Pro Leu Pro His Thr Pro Arg Met Tyr Ala
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 24

Gln Leu Tyr Glu Pro Asp Ser Gly Pro Trp Ala Pro
 1               5                  10
```

<210> SEQ ID NO 25
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 25

Trp Met Thr Lys Met Pro Thr Thr His Thr Arg Tyr
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 26

His His Pro Met Tyr Ser Met Thr Arg Ala Leu Pro
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 27

Gly Ser Ala His Ser Arg Asn Asp Ala Ala Pro Val
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 28

His Ser Pro Leu Met Gln Tyr His Met Ser Gly Thr
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 29

Thr Ala His Met Thr Met Pro Ser Arg Phe Leu Pro
 1               5                  10

<210> SEQ ID NO 30
<211> LENGTH: 10
<212> TYPE: PRT
<213> ORGANISM: Artificial Sequence
<220> FEATURE:
<223> OTHER INFORMATION: anodisk membrane-binding peptide

<400> SEQUENCE: 30

Ala Cys Pro Pro Thr Gln Ser Arg Tyr Cys
 1               5                  10

-continued

```
<210> SEQ ID NO 31
<211> LENGTH: 10
<212> TYPE: PRT
<213> ORGANISM: Artificial Sequence
<220> FEATURE:
<223> OTHER INFORMATION: anodisk membrane-binding peptide

<400> SEQUENCE: 31

Ala Cys Asn Gly Met Leu Ala Phe Gln Cys
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: anodisk membrane-binding peptide

<400> SEQUENCE: 32

Ala Cys Thr Pro Lys Pro Gly Lys His Cys
 1               5                  10

<210> SEQ ID NO 33
<211> LENGTH: 1680
<212> TYPE: DNA
<213> ORGANISM: Pseudomonas cichorii
<220> FEATURE:
<223> OTHER INFORMATION: Pseudomonas cichorii YN2 ; FERM BP-7375

<400> SEQUENCE: 33
atgagtaaca agagtaacga tgagttgaag tatcaagcct ctgaaaacac cttggggctt      60
aatcctgtcg ttgggctgcg tggaaaggat ctactggctt ctgctcgaat ggtgcttagg     120
caggccatca agcaaccggt gcacagcgtc aaacatgtcg cgcactttgg tcttgaactc     180
aagaacgtac tgctgggtaa atccgggctg caaccgacca gcgatgaccg tcgcttcgcc     240
gatccggcct ggagccagaa cccgctctat aaacgttatt tgcaaaccta cctggcgtgg     300
cgcaaggaac tccacgactg gatcgatgaa agtaacctcg ccccaaggga tgtggcgcgt     360
gggcacttcg tgatcaacct catgaccgaa gccatggcgc cgaccaacac gcggccaac      420 ccggcggcag tcaaacgctt tttcgaaacc ggtggcaaaa gcctgctcga cggcctctcg     480
cacctggcca aggatctggt acacaacggc ggcatgccga gccaggtcaa catgggtgca     540
ttcgaggtcg gcaagagcct gggcgtgacc gaaggcgcgg tggtgtttcg caacgatgtg     600
ctggaactga tccagtacaa gccgaccacc gagcaggtat acgaacgccc gctgctggtg     660
gtgccgccgc agatcaacaa gttctacgtt ttcgacctga gcccggacaa gagcctggcg     720
cggttctgcc tgcgcaacaa cgtgcaaacg ttcatcgtca gctggcgaaa tcccaccaag     780
gaacagcgag agtggggcct gtcgacctac atcgaagccc tcaaggaagc ggttgatgtc     840
gttaccgcga tcaccggcag caaagacgtg aacatgctcg gcgcctgctc cggcggcatc     900
acttgcaccg cgctgctggg ccattacgcg gcgattggcg aaaacaaggt caacgccctg     960
accttgctgg tgagcgtgct tgataccacc ctcgacagcg atgttgccct gttcgtcaat    1020 gaacagacccc ttgaagccgc caagcgccac tcgtaccagg ccggcgtact ggaaggccgc    1080
gacatggcga aggtcttcgc ctggatgcgc cccaacgatc tgatctggaa ctactgggtc    1140
aacaattacc tgctaggcaa cgaaccgccg gtgttcgaca tcctgttctg gaacaacgac    1200
accacacggt tgccccgcggc gttccacggc gacctgatcg aactgttcaa aaataaccca    1260
ctgattcgcc gaatgcact ggaagtgtgc ggcacccca tcgacctcaa gcaggtgacg    1320
```

```
gccgacatct tttccctggc cggcaccaac gaccacatca ccccgtggaa gtcctgctac   1380
aagtcggcgc aactgtttgg cggcaacgtt gaattcgtgc tgtcgagcag cgggcatatc   1440
cagagcatcc tgaacccgcc gggcaatccg aaatcgcgct acatgaccag caccgaagtg   1500
gcggaaaatg ccgatgaatg gcaagcgaat gccaccaagc ataccgattc ctggtggctg   1560
cactggcagg cctggcaggc caacgctcg  ggcgagctga aaaagtcccc gacaaaactg   1620
ggcagcaagg cgtatccggc aggtgaagcg cgccaggca cgtacgtgca cgaacggtaa    1680
```

<210> SEQ ID NO 34
<211> LENGTH: 1683
<212> TYPE: DNA
<213> ORGANISM: Pseudomonas cichorii
<220> FEATURE:
<223> OTHER INFORMATION: Pseudomonas cichorii YN2 ; FERM BP-7375

<400> SEQUENCE: 34

```
atgcgcgata aacctgcgag ggagtcacta cccaccccg ccaagttcat caacgcacaa     60
agtgcgatta ccggcctgcg tggccgggat ctggtttcga cttgcgcag tgtcgccgcc    120 catggcctgc gccaccccgt gcacaccgcg cgacacgcct tgaaactggg tggtcaactg    180
ggacgcgtgt tgctgggcga caccctgcat cccaccaacc cgcaagaccg tcgcttcgac    240
gatccggcgt ggagtctcaa tcccttttat cgtcgcagcc tgcaggcgta cctgagctgg    300
cagaagcagg tcaagagctg gatcgacgaa agcaacatga gcccggatga ccgcgcccgt    360
gcgcacttcg cgttcgccct gctcaacgat gccgtgtcgc cgtccaacag cctgctcaat    420
ccgctggcga tcaaggaaat cttcaactcc ggcggcaaca gcctggtgcg cgggatcggc    480
catctggtcg atgacctctt gcacaacgat ggcttgcccc ggcaagtcac caggcatgca    540
ttcgaggttg gcaagaccgt cgccaccacc accggcgccg tggtgtttcg caacgagctg    600
ctggagctga tccaatacaa gccgatgagc gaaaagcagt attccaaacc gctgctggtg    660
gtgccgccac agatcaacaa gtactacatt tttgacctca gccccataa  cagcttcgtc    720 cagttcgcgc tcaagaacgg cctgcaaaacc ttcgtcatca gctggcgcaa tccggatgta    780
cgtcaccgcg aatgggcct gtcgacctac gtcgaagcgg tggaagaagc catgaatgtc    840
tgccgggcaa tcaccggcgc gcgcgaggtc aacctgatgg gcgcctgcgc tggcgggctg    900
accattgctg ccctgcaggg ccacttgcaa gccaagcgac agctgcgccg cgtctccagc    960
gcgacgtacc tggtgagcct gctcgacagc caactggaca gcccggccac actcttcgcc   1020
gacgaacaga ccctggaggc ggccaagcgc cgctcctacc agaaaggtgt gctggaaggc   1080
cgcgacatgg ccaaggtttt cgcctggatg cgccccaacg atttgatctg gagctacttc   1140
gtcaacaatt acctgatggg caaggagccg ccggcgttcg acattctcta ctggaacaat   1200
gacaacacac gcctgccggc cgccctgcat ggtgacttgc tggacttctt caagcacaac   1260
ccgctgagcc atccgggtgg cctggaagtg tgcggcaccc cgatcgactt gcaaaaggtc   1320
accgtcgaca gtttcagcgt ggccggcatc aacgatcaca tcacgccgtg gacgcggtg    1380 tatcgctcaa ccctgttgct cggtggcgag cgtcgctttg tcctggccaa cagcggtcat   1440
gtgcagagca ttctcaaccc gccgaacaat ccgaaagcca actacctcga aggtgcaaaa   1500
ctaagcagcg accccaggc ctggtactac gacgccaagc ccgtcgacgg tagctggtgg   1560
acgcaatggc tgggctggat tcaggagcgc tcgggcgcgc aaaaagaaac ccacatggcc   1620
ctcggcaatc agaattatcc accgatggag gcggcgcccg ggacttacgt gcgcgtgcgc   1680
tga                                                                 1683
```

<210> SEQ ID NO 35
<211> LENGTH: 559
<212> TYPE: PRT
<213> ORGANISM: Pseudomonas cichorii YN2 ; FERM BP-7375

<400> SEQUENCE: 35

Met Ser Asn Lys Ser Asn Asp Glu Leu Lys Tyr Gln Ala Ser Glu Asn
1               5                   10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
        275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu

-continued

```
                370                 375                 380
Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
                420                 425                 430

Pro Ile Asp Leu Lys Gln Val Thr Ala Asp Ile Phe Ser Leu Ala Gly
                435                 440                 445

Thr Asn Asp His Ile Thr Pro Trp Lys Ser Cys Tyr Lys Ser Ala Gln
450                 455                 460

Leu Phe Gly Gly Asn Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
                500                 505                 510

Lys His Thr Asp Ser Trp Trp Leu His Trp Gln Ala Trp Gln Ala Gln
                515                 520                 525

Arg Ser Gly Glu Leu Lys Lys Ser Pro Thr Lys Leu Gly Ser Lys Ala
                530                 535                 540

Tyr Pro Ala Gly Glu Ala Ala Pro Gly Thr Tyr Val His Glu Arg
545                 550                 555

<210> SEQ ID NO 36
<211> LENGTH: 560
<212> TYPE: PRT
<213> ORGANISM: Pseudomonas cichorii YN2 ; FERM BP-7375

<400> SEQUENCE: 36

Met Arg Asp Lys Pro Ala Arg Glu Ser Leu Pro Thr Pro Ala Lys Phe
1               5                   10                  15

Ile Asn Ala Gln Ser Ala Ile Thr Gly Leu Arg Gly Arg Asp Leu Val
                20                  25                  30

Ser Thr Leu Arg Ser Val Ala Ala His Gly Leu Arg His Pro Val His
            35                  40                  45

Thr Ala Arg His Ala Leu Lys Leu Gly Gly Gln Leu Gly Arg Val Leu
        50                  55                  60

Leu Gly Asp Thr Leu His Pro Thr Asn Pro Gln Asp Arg Arg Phe Asp
65                  70                  75                  80

Asp Pro Ala Trp Ser Leu Asn Pro Phe Tyr Arg Arg Ser Leu Gln Ala
                85                  90                  95

Tyr Leu Ser Trp Gln Lys Gln Val Lys Ser Trp Ile Asp Glu Ser Asn
                100                 105                 110

Met Ser Pro Asp Asp Arg Ala Arg Ala His Phe Ala Phe Ala Leu Leu
            115                 120                 125

Asn Asp Ala Val Ser Pro Ser Asn Ser Leu Leu Asn Pro Leu Ala Ile
        130                 135                 140

Lys Glu Ile Phe Asn Ser Gly Gly Asn Ser Leu Val Arg Gly Ile Gly
145                 150                 155                 160

His Leu Val Asp Asp Leu Leu His Asn Asp Gly Leu Pro Arg Gln Val
                165                 170                 175

Thr Arg His Ala Phe Glu Val Gly Lys Thr Val Ala Thr Thr Thr Gly
                180                 185                 190
```

-continued

```
Ala Val Val Phe Arg Asn Glu Leu Leu Glu Leu Ile Gln Tyr Lys Pro
        195                 200                 205

Met Ser Glu Lys Gln Tyr Ser Lys Pro Leu Leu Val Val Pro Pro Gln
    210                 215                 220

Ile Asn Lys Tyr Tyr Ile Phe Asp Leu Ser Pro His Asn Ser Phe Val
225                 230                 235                 240

Gln Phe Ala Leu Lys Asn Gly Leu Gln Thr Phe Val Ile Ser Trp Arg
                245                 250                 255

Asn Pro Asp Val Arg His Arg Glu Trp Gly Leu Ser Thr Tyr Val Glu
            260                 265                 270

Ala Val Glu Glu Ala Met Asn Val Cys Arg Ala Ile Thr Gly Ala Arg
        275                 280                 285

Glu Val Asn Leu Met Gly Ala Cys Ala Gly Gly Leu Thr Ile Ala Ala
    290                 295                 300

Leu Gln Gly His Leu Gln Ala Lys Arg Gln Leu Arg Arg Val Ser Ser
305                 310                 315                 320

Ala Thr Tyr Leu Val Ser Leu Leu Asp Ser Gln Leu Asp Ser Pro Ala
                325                 330                 335

Thr Leu Phe Ala Asp Glu Gln Thr Leu Glu Ala Ala Lys Arg Arg Ser
            340                 345                 350

Tyr Gln Lys Gly Val Leu Glu Gly Arg Asp Met Ala Lys Val Phe Ala
        355                 360                 365

Trp Met Arg Pro Asn Asp Leu Ile Trp Ser Tyr Phe Val Asn Asn Tyr
    370                 375                 380

Leu Met Gly Lys Glu Pro Pro Ala Phe Asp Ile Leu Tyr Trp Asn Asn
385                 390                 395                 400

Asp Asn Thr Arg Leu Pro Ala Ala Leu His Gly Asp Leu Leu Asp Phe
                405                 410                 415

Phe Lys His Asn Pro Leu Ser His Pro Gly Gly Leu Glu Val Cys Gly
            420                 425                 430

Thr Pro Ile Asp Leu Gln Lys Val Thr Val Asp Ser Phe Ser Val Ala
        435                 440                 445

Gly Ile Asn Asp His Ile Thr Pro Trp Asp Ala Val Tyr Arg Ser Thr
    450                 455                 460

Leu Leu Leu Gly Gly Glu Arg Arg Phe Val Leu Ala Asn Ser Gly His
465                 470                 475                 480

Val Gln Ser Ile Leu Asn Pro Pro Asn Asn Pro Lys Ala Asn Tyr Leu
                485                 490                 495

Glu Gly Ala Lys Leu Ser Ser Asp Pro Arg Ala Trp Tyr Tyr Asp Ala
            500                 505                 510

Lys Pro Val Asp Gly Ser Trp Trp Thr Gln Trp Leu Gly Trp Ile Gln
        515                 520                 525

Glu Arg Ser Gly Ala Gln Lys Glu Thr His Met Ala Leu Gly Asn Gln
    530                 535                 540

Asn Tyr Pro Pro Met Glu Ala Ala Pro Gly Thr Tyr Val Arg Val Arg
545                 550                 555                 560
```

<210> SEQ ID NO 37
<211> LENGTH: 20
<212> TYPE: DNA
<213> ORGANISM: Artificial Sequence
<220> FEATURE:
<223> OTHER INFORMATION: Primer for PCR multiplication

<400> SEQUENCE: 37

```
tgctggaact gatccagtac                                              20
```

<210> SEQ ID NO 38
<211> LENGTH: 23
<212> TYPE: DNA
<213> ORGANISM: Artificial Sequence
<220> FEATURE:
<223> OTHER INFORMATION: Primer for PCR multiplication

<400> SEQUENCE: 38

```
gggttgagga tgctctggat gtg                                          23
```

<210> SEQ ID NO 39
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 39

```
cgagcaagct tgctcctaca ggtgaaggc                                    29
```

<210> SEQ ID NO 40
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 40

```
gtattaagct tgaagacgaa ggagtgttg                                    29
```

<210> SEQ ID NO 41
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 41

```
ggaccaagct tctcgtctca gggcaatgg                                    29
```

<210> SEQ ID NO 42
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 42

```
catccaagct tcttatgatc gggtcatgcc                                   30
```

<210> SEQ ID NO 43
<211> LENGTH: 45
<212> TYPE: DNA
<213> ORGANISM: Artificial Sequence
<220> FEATURE:
<223> OTHER INFORMATION: Primer for PCR multiplication

<400> SEQUENCE: 43

```
agtggatcct ccgagctcag taacaagagt aacgatgagt tgaag                  45
```

<210> SEQ ID NO 44
<211> LENGTH: 45
<212> TYPE: DNA
<213> ORGANISM: Artificial Sequence

```
<220> FEATURE:
<223> OTHER INFORMATION: Primer for PCR multiplication

<400> SEQUENCE: 44
atactcgaga ctactagtcc gttcgtgcac gtacgtgcct ggcgc            45

<210> SEQ ID NO 45
<211> LENGTH: 45
<212> TYPE: DNA
<213> ORGANISM: Artificial Sequence
<220> FEATURE:
<223> OTHER INFORMATION: Primer for PCR multiplication

<400> SEQUENCE: 45
atactcgaga ctactagtgc gcacgcgcac gtaagtcccg ggcgc            45

<210> SEQ ID NO 46
<211> LENGTH: 45
<212> TYPE: DNA
<213> ORGANISM: Artificial Sequence
<220> FEATURE:
<223> OTHER INFORMATION: Primer for PCR multiplication

<400> SEQUENCE: 46
agtggatcct ccgagctccg cgataaacct gcgagggagt cacta            45

<210> SEQ ID NO 47
<211> LENGTH: 58
<212> TYPE: DNA
<213> ORGANISM: Artificial Sequence
<220> FEATURE:
<223> OTHER INFORMATION: Coding chain for peptide of SEQ ID:1

<400> SEQUENCE: 47
gatccgttta tgcgaatcag actccgcctt ctaaggcgcg gggtggaggt tcggagct    58

<210> SEQ ID NO 48
<211> LENGTH: 50
<212> TYPE: DNA
<213> ORGANISM: Artificial Sequence
<220> FEATURE:
<223> OTHER INFORMATION: Complimentary chain for ssDNA of SEQ ID:1

<400> SEQUENCE: 48
ccgaacctcc accccgcgcc ttagaaggcg gagtctgatt cgcataaacg         50

<210> SEQ ID NO 49
<211> LENGTH: 58
<212> TYPE: DNA
<213> ORGANISM: Artificial Sequence
<220> FEATURE:
<223> OTHER INFORMATION: Coding chain for peptide of SEQ ID:2

<400> SEQUENCE: 49
gatcccagtc ttcgattacg actcggaatc cttttatgac tggtggaggt tcggagct    58

<210> SEQ ID NO 50
<211> LENGTH: 50
<212> TYPE: DNA
<213> ORGANISM: Artificial Sequence
<220> FEATURE:
<223> OTHER INFORMATION: Complimentary chain for ssDNA of SEQ ID:2

<400> SEQUENCE: 50
ccgaacctcc accagtcata aaaggattcc gagtcgtaat cgaagactgg         50
```

<210> SEQ ID NO 51
<211> LENGTH: 58
<212> TYPE: DNA
<213> ORGANISM: Artificial Sequence
<220> FEATURE:
<223> OTHER INFORMATION: Coding chain for peptide of SEQ ID:3

<400> SEQUENCE: 51
gatcctttat gaatcatcat ccgaattcgc agcagtatca tggtggaggt tcggagct    58

<210> SEQ ID NO 52
<211> LENGTH: 50
<212> TYPE: DNA
<213> ORGANISM: Artificial Sequence
<220> FEATURE:
<223> OTHER INFORMATION: Complimentary chain for ssDNA of SEQ ID:3

<400> SEQUENCE: 52
ccgaacctcc accatgatac tgctgcgaat tcggatgatg attcataaag              50

<210> SEQ ID NO 53
<211> LENGTH: 58
<212> TYPE: DNA
<213> ORGANISM: Artificial Sequence
<220> FEATURE:
<223> OTHER INFORMATION: Coding chain for peptide of SEQ ID:4

<400> SEQUENCE: 53
gatcccagta tacgtcgtcg ggtattatta cgtcgtctgc tggtggaggt tcggagct    58

<210> SEQ ID NO 54
<211> LENGTH: 50
<212> TYPE: DNA
<213> ORGANISM: Artificial Sequence
<220> FEATURE:
<223> OTHER INFORMATION: Complimentary chain for ssDNA of SEQ ID:4

<400> SEQUENCE: 54
ccgaacctcc accagcagac gacgtaataa tacccgacga cgtatactgg              50

<210> SEQ ID NO 55
<211> LENGTH: 58
<212> TYPE: DNA
<213> ORGANISM: Artificial Sequence
<220> FEATURE:
<223> OTHER INFORMATION: Coding chain for peptide of SEQ ID:5

<400> SEQUENCE: 55
gatcccagcc gcatatgcat cggagttctc atcaggatgg gggtggaggt tcggagct    58

<210> SEQ ID NO 56
<211> LENGTH: 50
<212> TYPE: DNA
<213> ORGANISM: Artificial Sequence
<220> FEATURE:
<223> OTHER INFORMATION: Complimentary chain for ssDNA of SEQ ID:5

<400> SEQUENCE: 56
ccgaacctcc accccatcc tgatgagaac tccgatgcat atgcggctgg               50

<210> SEQ ID NO 57
<211> LENGTH: 58
<212> TYPE: DNA
<213> ORGANISM: Artificial Sequence
<220> FEATURE:
<223> OTHER INFORMATION: Coding chain for peptide of SEQ ID:6

<400> SEQUENCE: 57
gatccaatac tactatgggg ccgatgagtc ctcatagtca gggtggaggt tcggagct       58

<210> SEQ ID NO 58
<211> LENGTH: 50
<212> TYPE: DNA
<213> ORGANISM: Artificial Sequence
<220> FEATURE:
<223> OTHER INFORMATION: Complimentary chain for ssDNA of SEQ ID:6

<400> SEQUENCE: 58
ccgaacctcc accctgacta tgaggactca tcggccccat agtagtattg             50

<210> SEQ ID NO 59
<211> LENGTH: 58
<212> TYPE: DNA
<213> ORGANISM: Artificial Sequence
<220> FEATURE:
<223> OTHER INFORMATION: Coding chain for peptide of SEQ ID:7

<400> SEQUENCE: 59
gatcccatca tcatccggag aatttggatt ctacttttca gggtggaggt tcggagct       58

<210> SEQ ID NO 60
<211> LENGTH: 50
<212> TYPE: DNA
<213> ORGANISM: Artificial Sequence
<220> FEATURE:
<223> OTHER INFORMATION: Complimentary chain for ssDNA of SEQ ID:7

<400> SEQUENCE: 60
ccgaacctcc accctgaaaa gtagaatcca aattctccgg atgatgatgg             50

<210> SEQ ID NO 61
<211> LENGTH: 58
<212> TYPE: DNA
<213> ORGANISM: Artificial Sequence
<220> FEATURE:
<223> OTHER INFORMATION: Coding chain for peptide of SEQ ID:8

<400> SEQUENCE: 61
gatccgctgc tcattttgag cctcagacta tgcctatgat tggtggaggt tcggagct       58

<210> SEQ ID NO 62
<211> LENGTH: 50
<212> TYPE: DNA
<213> ORGANISM: Artificial Sequence
<220> FEATURE:
<223> OTHER INFORMATION: Complimentary chain for ssDNA of SEQ ID:8

<400> SEQUENCE: 62
ccgaacctcc accaatcata ggcatagtct gaggctcaaa atgagcagcg             50

<210> SEQ ID NO 63
<211> LENGTH: 58
<212> TYPE: DNA
<213> ORGANISM: Artificial Sequence
<220> FEATURE:
<223> OTHER INFORMATION: Coding chain for peptide of SEQ ID:9

<400> SEQUENCE: 63
gatccgatca tcagcttcat cgtcctccgc atatgatgag gggtggaggt tcggagct       58

<210> SEQ ID NO 64

```
<210> SEQ ID NO 64
<211> LENGTH: 50
<212> TYPE: DNA
<213> ORGANISM: Artificial Sequence
<220> FEATURE:
<223> OTHER INFORMATION: Complimentary chain for ssDNA of SEQ ID:9

<400> SEQUENCE: 64
ccgaacctcc acccctcatc atatgcggag gacgatgaag ctgatgatcg            50

<210> SEQ ID NO 65
<211> LENGTH: 58
<212> TYPE: DNA
<213> ORGANISM: Artificial Sequence
<220> FEATURE:
<223> OTHER INFORMATION: Coding chain for peptide of SEQ ID:10

<400> SEQUENCE: 65
gatccgtttc gcgtcatcag tcgtggcatc cgcatgatct tggtggaggt tcggagct   58

<210> SEQ ID NO 66
<211> LENGTH: 50
<212> TYPE: DNA
<213> ORGANISM: Artificial Sequence
<220> FEATURE:
<223> OTHER INFORMATION: Complimentary chain for ssDNA of SEQ ID:10

<400> SEQUENCE: 66
ccgaacctcc accaagatca tgcggatgcc acgactgatg acgcgaaacg            50

<210> SEQ ID NO 67
<211> LENGTH: 58
<212> TYPE: DNA
<213> ORGANISM: Artificial Sequence
<220> FEATURE:
<223> OTHER INFORMATION: Coding chain for peptide of SEQ ID:11

<400> SEQUENCE: 67
gatccatgat gcagagggat catcatcagc ataatgcgca gggtggaggt tcggagct   58

<210> SEQ ID NO 68
<211> LENGTH: 50
<212> TYPE: DNA
<213> ORGANISM: Artificial Sequence
<220> FEATURE:
<223> OTHER INFORMATION: Complimentary chain for ssDNA of SEQ ID:11

<400> SEQUENCE: 68
ccgaacctcc accctgcgca ttatgctgat gatgatccct ctgcatcatg            50

<210> SEQ ID NO 69
<211> LENGTH: 58
<212> TYPE: DNA
<213> ORGANISM: Artificial Sequence
<220> FEATURE:
<223> OTHER INFORMATION: Coding chain for peptide of SEQ ID:12

<400> SEQUENCE: 69
gatccgttac tcttcatacg gtggatcatg cgccgcaaga tggtggaggt tcggagct   58

<210> SEQ ID NO 70
<211> LENGTH: 50
<212> TYPE: DNA
<213> ORGANISM: Artificial Sequence
<220> FEATURE:
<223> OTHER INFORMATION: Complimentary chain for ssDNA of SEQ ID:12

<400> SEQUENCE: 70
```
ccgaacctcc accatcttgc ggcgcatgat ccaccgtatg aagagtaacg        50

<210> SEQ ID NO 71
<211> LENGTH: 58
<212> TYPE: DNA
<213> ORGANISM: Artificial Sequence
<220> FEATURE:
<223> OTHER INFORMATION: Coding chain for peptide of SEQ ID:13

<400> SEQUENCE: 71
gatcctctgt ttctgtgggt atgaagccga gtcctaggcc tggtggaggt tcggagct        58

<210> SEQ ID NO 72
<211> LENGTH: 50
<212> TYPE: DNA
<213> ORGANISM: Artificial Sequence
<220> FEATURE:
<223> OTHER INFORMATION: Complimentary chain for ssDNA of SEQ ID:13

<400> SEQUENCE: 72
ccgaacctcc accaggccta ggactcggct tcatacccac agaaacagag        50

<210> SEQ ID NO 73
<211> LENGTH: 58
<212> TYPE: DNA
<213> ORGANISM: Artificial Sequence
<220> FEATURE:
<223> OTHER INFORMATION: Coding chain for peptide of SEQ ID:14

<400> SEQUENCE: 73
gatcccatct tcagtctatg aagcctcgta ctcatgtgtt gggtggaggt tcggagct        58

<210> SEQ ID NO 74
<211> LENGTH: 50
<212> TYPE: DNA
<213> ORGANISM: Artificial Sequence
<220> FEATURE:
<223> OTHER INFORMATION: Complimentary chain for ssDNA of SEQ ID:14

<400> SEQUENCE: 74
ccgaacctcc acccaacaca tgagtacgag gcttcataga ctgaagatgg        50

<210> SEQ ID NO 75
<211> LENGTH: 58
<212> TYPE: DNA
<213> ORGANISM: Artificial Sequence
<220> FEATURE:
<223> OTHER INFORMATION: Coding chain for peptide of SEQ ID:15

<400> SEQUENCE: 75
gatccattcc taatgctgag actttgcgtc agcctgcgcg tggtggaggt tcggagct        58

<210> SEQ ID NO 76
<211> LENGTH: 50
<212> TYPE: DNA
<213> ORGANISM: Artificial Sequence
<220> FEATURE:
<223> OTHER INFORMATION: Complimentary chain for ssDNA of SEQ ID:15

<400> SEQUENCE: 76
ccgaacctcc accacgcgca ggctgacgca aagtctcagc attaggaatg        50

<210> SEQ ID NO 77
<211> LENGTH: 58
<212> TYPE: DNA

<213> ORGANISM: Artificial Sequence
<220> FEATURE:
<223> OTHER INFORMATION: Coding chain for peptide of SEQ ID:16

<400> SEQUENCE: 77
gatccgttcg cgtcatcagt tcgtggcatc cgcatgatct tggtggaggt tcggagct        58

<210> SEQ ID NO 78
<211> LENGTH: 50
<212> TYPE: DNA
<213> ORGANISM: Artificial Sequence
<220> FEATURE:
<223> OTHER INFORMATION: Complimentary chain for ssDNA of SEQ ID:16

<400> SEQUENCE: 78
ccgaacctcc accaagatca tgcggatgcc acgaactgat gacgcgaacg        50

<210> SEQ ID NO 79
<211> LENGTH: 58
<212> TYPE: DNA
<213> ORGANISM: Artificial Sequence
<220> FEATURE:
<223> OTHER INFORMATION: Coding chain for peptide of SEQ ID:17

<400> SEQUENCE: 79
gatccacggt gccgatttat aatacgggga ttttgaggac gggtggaggt tcggagct        58

<210> SEQ ID NO 80
<211> LENGTH: 50
<212> TYPE: DNA
<213> ORGANISM: Artificial Sequence
<220> FEATURE:
<223> OTHER INFORMATION: Complimentary chain for ssDNA of SEQ ID:17

<400> SEQUENCE: 80
ccgaacctcc acccgtcctc aaaatccccg tattataaat cggcaccgtg        50

<210> SEQ ID NO 81
<211> LENGTH: 58
<212> TYPE: DNA
<213> ORGANISM: Artificial Sequence
<220> FEATURE:
<223> OTHER INFORMATION: Coding chain for peptide of SEQ ID:18

<400> SEQUENCE: 81
gatcctatac tatgcatcat gggtcgacgt ttatacggcg gggtggaggt tcggagct        58

<210> SEQ ID NO 82
<211> LENGTH: 50
<212> TYPE: DNA
<213> ORGANISM: Artificial Sequence
<220> FEATURE:
<223> OTHER INFORMATION: Complimentary chain for ssDNA of SEQ ID:18

<400> SEQUENCE: 82
ccgaacctcc accccgccgt ataaacgtcg acccatgatg catagtatag        50

<210> SEQ ID NO 83
<211> LENGTH: 58
<212> TYPE: DNA
<213> ORGANISM: Artificial Sequence
<220> FEATURE:
<223> OTHER INFORMATION: Coding chain for peptide of SEQ ID:19

<400> SEQUENCE: 83
gatcctcgat gatgcatgtg aatattcgtc tcgggattct tggtggaggt tcggagct        58

<210> SEQ ID NO 84
<211> LENGTH: 50
<212> TYPE: DNA
<213> ORGANISM: Artificial Sequence
<220> FEATURE:
<223> OTHER INFORMATION: Complimentary chain for ssDNA of SEQ ID:19

<400> SEQUENCE: 84
ccgaacctcc accaagaatc ccgagacgaa tattcacatg catcatcgag        50

<210> SEQ ID NO 85
<211> LENGTH: 58
<212> TYPE: DNA
<213> ORGANISM: Artificial Sequence
<220> FEATURE:
<223> OTHER INFORMATION: Coding chain for peptide of SEQ ID:20

<400> SEQUENCE: 85
gatccgcgcc gatgcatcat atgaagagtc tgtatcgggc gggtggaggt tcggagct   58

<210> SEQ ID NO 86
<211> LENGTH: 50
<212> TYPE: DNA
<213> ORGANISM: Artificial Sequence
<220> FEATURE:
<223> OTHER INFORMATION: Complimentary chain for ssDNA of SEQ ID:20

<400> SEQUENCE: 86
ccgaacctcc acccgcccga tacagactct tcatatgatg catcggcgcg        50

<210> SEQ ID NO 87
<211> LENGTH: 58
<212> TYPE: DNA
<213> ORGANISM: Artificial Sequence
<220> FEATURE:
<223> OTHER INFORMATION: Coding chain for peptide of SEQ ID:21

<400> SEQUENCE: 87
gatccatgat gcagagggat catcatcagc atatgcgcag gggtggaggt tcggagct   58

<210> SEQ ID NO 88
<211> LENGTH: 50
<212> TYPE: DNA
<213> ORGANISM: Artificial Sequence
<220> FEATURE:
<223> OTHER INFORMATION: Complimentary chain for ssDNA of SEQ ID:21

<400> SEQUENCE: 88
ccgaacctcc acccctgcgc atatgctgat gatgatccct ctgcatcatg        50

<210> SEQ ID NO 89
<211> LENGTH: 58
<212> TYPE: DNA
<213> ORGANISM: Artificial Sequence
<220> FEATURE:
<223> OTHER INFORMATION: Coding chain for peptide of SEQ ID:22

<400> SEQUENCE: 89
gatccatgaa gactcatcat ggtaataatg cggtgtttct gggtggaggt tcggagct   58

<210> SEQ ID NO 90
<211> LENGTH: 50
<212> TYPE: DNA
<213> ORGANISM: Artificial Sequence
<220> FEATURE:

<223> OTHER INFORMATION: Complimentary chain for ssDNA of SEQ ID:22

<400> SEQUENCE: 90
ccgaacctcc acccagaaac accgcattat taccatgatg agtcttcatg              50

<210> SEQ ID NO 91
<211> LENGTH: 58
<212> TYPE: DNA
<213> ORGANISM: Artificial Sequence
<220> FEATURE:
<223> OTHER INFORMATION: Coding chain for peptide of SEQ ID:23

<400> SEQUENCE: 91
gatccttgga gccgcttcct catactcctc ggatgtatgc gggtggaggt tcggagct     58

<210> SEQ ID NO 92
<211> LENGTH: 50
<212> TYPE: DNA
<213> ORGANISM: Artificial Sequence
<220> FEATURE:
<223> OTHER INFORMATION: Complimentary chain for ssDNA of SEQ ID:23

<400> SEQUENCE: 92
ccgaacctcc acccgcatac atccgaggag tatgaggaag cggctccaag              50

<210> SEQ ID NO 93
<211> LENGTH: 58
<212> TYPE: DNA
<213> ORGANISM: Artificial Sequence
<220> FEATURE:
<223> OTHER INFORMATION: Coding chain for peptide of SEQ ID:24

<400> SEQUENCE: 93
gatcccagct gtatgagcct gattctgggc cgtgggctcc gggtggaggt tcggagct     58

<210> SEQ ID NO 94
<211> LENGTH: 50
<212> TYPE: DNA
<213> ORGANISM: Artificial Sequence
<220> FEATURE:
<223> OTHER INFORMATION: Complimentary chain for ssDNA of SEQ ID:24

<400> SEQUENCE: 94
ccgaacctcc acccggagcc cacggcccag aatcaggctc atacagctgg              50

<210> SEQ ID NO 95
<211> LENGTH: 58
<212> TYPE: DNA
<213> ORGANISM: Artificial Sequence
<220> FEATURE:
<223> OTHER INFORMATION: Coding chain for peptide of SEQ ID:25

<400> SEQUENCE: 95
gatcctggat gactaagatg cctactacgc atactaggta tggtggaggt tcggagct     58

<210> SEQ ID NO 96
<211> LENGTH: 50
<212> TYPE: DNA
<213> ORGANISM: Artificial Sequence
<220> FEATURE:
<223> OTHER INFORMATION: Complimentary chain for ssDNA of SEQ ID:25

<400> SEQUENCE: 96
ccgaacctcc accataccta gtatgcgtag taggcatctt agtcatccag              50

<210> SEQ ID NO 97
<211> LENGTH: 58
<212> TYPE: DNA
<213> ORGANISM: Artificial Sequence
<220> FEATURE:
<223> OTHER INFORMATION: Coding chain for peptide of SEQ ID:26

<400> SEQUENCE: 97
gatcccatca tcctatgtat tctatgacta gggcgttgcc tggtggaggt tcggagct        58

<210> SEQ ID NO 98
<211> LENGTH: 50
<212> TYPE: DNA
<213> ORGANISM: Artificial Sequence
<220> FEATURE:
<223> OTHER INFORMATION: Complimentary chain for ssDNA of SEQ ID:26

<400> SEQUENCE: 98
ccgaacctcc accaggcaac gccctagtca tagaatacat aggatgatgg        50

<210> SEQ ID NO 99
<211> LENGTH: 58
<212> TYPE: DNA
<213> ORGANISM: Artificial Sequence
<220> FEATURE:
<223> OTHER INFORMATION: Coding chain for peptide of SEQ ID:27

<400> SEQUENCE: 99
gatccggtag tgctcattct cggaatgatg ctgctcctgt gggtggaggt tcggagct        58

<210> SEQ ID NO 100
<211> LENGTH: 50
<212> TYPE: DNA
<213> ORGANISM: Artificial Sequence
<220> FEATURE:
<223> OTHER INFORMATION: Complimentary chain for ssDNA of SEQ ID:27

<400> SEQUENCE: 100
ccgaacctcc acccacagga gcagcatcat tccgagaatg agcactaccg        50

<210> SEQ ID NO 101
<211> LENGTH: 58
<212> TYPE: DNA
<213> ORGANISM: Artificial Sequence
<220> FEATURE:
<223> OTHER INFORMATION: Coding chain for peptide of SEQ ID:28

<400> SEQUENCE: 101
gatcccattc gcctttgatg cagtatcata tgtcgggtac gggtggaggt tcggagct        58

<210> SEQ ID NO 102
<211> LENGTH: 50
<212> TYPE: DNA
<213> ORGANISM: Artificial Sequence
<220> FEATURE:
<223> OTHER INFORMATION: Complimentary chain for ssDNA of SEQ ID:28

<400> SEQUENCE: 102
ccgaacctcc acccgtaccc gacatatgat actgcatcaa aggcgaatgg        50

<210> SEQ ID NO 103
<211> LENGTH: 58
<212> TYPE: DNA
<213> ORGANISM: Artificial Sequence
<220> FEATURE:
<223> OTHER INFORMATION: Coding chain for peptide of SEQ ID:29

```
<400> SEQUENCE: 103
gatcctatgc gcatatgacg atgccgtctc ggttttgcc gggtggaggt tcggagct        58

<210> SEQ ID NO 104
<211> LENGTH: 50
<212> TYPE: DNA
<213> ORGANISM: Artificial Sequence
<220> FEATURE:
<223> OTHER INFORMATION: Complimentary chain for ssDNA of SEQ ID:29

<400> SEQUENCE: 104
ccgaacctcc acccggcaaa aaccgagacg gcatcgtcat atgcgcatag                50

<210> SEQ ID NO 105
<211> LENGTH: 52
<212> TYPE: DNA
<213> ORGANISM: Artificial Sequence
<220> FEATURE:
<223> OTHER INFORMATION: Coding chain for peptide of SEQ ID:30

<400> SEQUENCE: 105
gatccgcttg tccgcctacg cagtctcggt attgcggtgg aggttcggag ct             52

<210> SEQ ID NO 106
<211> LENGTH: 44
<212> TYPE: DNA
<213> ORGANISM: Artificial Sequence
<220> FEATURE:
<223> OTHER INFORMATION: Complimentary chain for ssDNA of SEQ ID:30

<400> SEQUENCE: 106
ccgaacctcc accgcaatac cgagactgcg taggcggaca agcg                      44

<210> SEQ ID NO 107
<211> LENGTH: 52
<212> TYPE: DNA
<213> ORGANISM: Artificial Sequence
<220> FEATURE:
<223> OTHER INFORMATION: Coding chain for peptide of SEQ ID:31

<400> SEQUENCE: 107
gatccgcttg taatggcatg ttggcctttc agtgcggtgg aggttcggag ct             52

<210> SEQ ID NO 108
<211> LENGTH: 44
<212> TYPE: DNA
<213> ORGANISM: Artificial Sequence
<220> FEATURE:
<223> OTHER INFORMATION: Complimentary chain for ssDNA of SEQ ID:31

<400> SEQUENCE: 108
ccgaacctcc accgcactga aaggccaaca tgccattaca agcg                      44

<210> SEQ ID NO 109
<211> LENGTH: 52
<212> TYPE: DNA
<213> ORGANISM: Artificial Sequence
<220> FEATURE:
<223> OTHER INFORMATION: Coding chain for peptide of SEQ ID:32

<400> SEQUENCE: 109
gatccgcttg tacgccgaag ccgggcaagc attgcggtgg aggttcggag ct             52

<210> SEQ ID NO 110
<211> LENGTH: 44
```

```
<212> TYPE: DNA
<213> ORGANISM: Artificial Sequence
<220> FEATURE:
<223> OTHER INFORMATION: Complimentary chain for ssDNA of SEQ ID:32

<400> SEQUENCE: 110
ccgaacctcc accgcaatgc ttgcccggct tcggcgtaca agcg                44

<210> SEQ ID NO 111
<211> LENGTH: 972
<212> TYPE: DNA
<213> ORGANISM: Artificial Sequence
<220> FEATURE:
<223> OTHER INFORMATION: HPR coding artificial sense-sequence

<400> SEQUENCE: 111
gtttatgcca accaaacccc accaagcaag gcgaggggtg gaggttcgca acttaccct     60 accttctacg acaattcatg tcctaatgtc tctaacatcg tacgggatac tattgtcaat   120
gagctaagat cagaccctcg tattgccgcg agcatccttc gtcttcactt ccacgactgc   180
tttgttaatg gttgtgacgc atcgatcttg ttagacaaca caacatcatt tcgaacagag   240
aaagatgcgt ttggaaacgc aaactcggca agaggatttc cagtgattga taagatgaaa   300
gccgcggtgg agagtgcatg cccaagaacc gtttcatgcg cagatttgct caccattgca   360
gctcaacaat ctgtcacttt ggcgggaggt ccttcttgga gagttccttt gggcagaaga   420
gatagcttac aagcatttct ggatcttgct aatgcaaatc ttccagctcc attcttcaca   480
cttccacaac ttaaagacag cttagaaat gttggcctca accgttcttc tgatctcgtt    540
gcactgtccg ggggccacac atttggtaaa aatcagtgtc ggtttattat ggacagatta   600
tacaacttca gcaacaccgg tttacccgat cctactctca acactactta tctccaaact   660
cttcgtggac tatgtcccct caatggtaat ctaagcgctt tggtggattt tgatctacgt   720
acgccaacga ttttgacaa caaatactat gtgaatctcg aagaggaaaa aggacttatc    780
caaagcgacc aagagttgtt ctctagcccc aatgccactg cacacaatcc ttggtgaga    840 tcatttgcta atagcacaca acattcttc aatgcatttg tggaggcgat ggataggatg    900
ggaaacatta cacctcttac aggaactcaa ggacagatca ggttgaattg tagggtggtg   960
aactccaact ct                                                      972

<210> SEQ ID NO 112
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 112
gtttatgcca accaaacccc accaagcaag gcgaggggtg gaggttcgca acttaccct     60 accttctacg acaattcatg tcctaatgtc tctaacatcg tacgggatac tattgtcaat   120

<210> SEQ ID NO 113
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 113
gtttatgcca accaaacccc accaagcaag                                    30
```

<210> SEQ ID NO 114
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 114
tgttgtctaa caagatcgat gcgtcacaac cattaacaaa gcagtcgtgg aagtgaagac     60
gaaggatgct cgcggcaata cgagggtctg atcttagctc attgacaata gtatcccgta    120

<210> SEQ ID NO 115
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 115
tgttgtctaa caagatcgat gcgtcacaac                                      30

<210> SEQ ID NO 116
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 116
atcgatcttg ttagacaaca caacatcatt tcgaacagag aaagatgcgt ttggaaacgc     60
aaactcggca agaggatttc cagtgattga tagaatgaaa gccgcggtgg agagtgcatg    120

<210> SEQ ID NO 117
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 117
atcgatcttg ttagacaaca caacatcatt                                      30

<210> SEQ ID NO 118
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 118
tcttctgccc aaaggaactc tccaagaagg acctcccgcc aaagtgacag attgttgagc     60
tgcaatggtg agcaaatctg cgcatgaaac ggttcttggg catgcactct ccaccgcggc    120

<210> SEQ ID NO 119
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 119
tcttctgccc aaaggaactc tccaagaagg                                      30

```
<210> SEQ ID NO 120
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 120
gagttccttt gggcagaaga gatagcttac aagcatttct ggatcttgct aatgcaaatc      60
ttccagctcc attcttcaca cttccacaac ttaaagacag ctttagaaat gttggcctca     120

<210> SEQ ID NO 121
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 121
gagttccttt gggcagaaga gatagcttac                                       30

<210> SEQ ID NO 122
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 122
ccggtgttgc tgaagttgta taatctgtcc ataataaacc gacactgatt tttaccaaat      60
gtgtggcccc cggacagtgc aacgagatca gaagaacggt tgaggccaac atttctaaag    120

<210> SEQ ID NO 123
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 123
ccggtgttgc tgaagttgta taatctgtcc                                       30

<210> SEQ ID NO 124
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 124
tacaacttca gcaacaccgg tttacccgat cctactctca acactactta tctccaaact      60
cttcgtggac tatgtcccct caatggtaat ctaagcgctt tggtggattt tgatctacgt     120

<210> SEQ ID NO 125
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 125
tacaacttca gcaacaccgg tttacccgat                                       30

<210> SEQ ID NO 126
```

```
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 126
cagtggcatt ggggctagag aacaactctt ggtcgctttg gataagtcct ttttcctctt      60
cgagattcac atagtatttg ttgtcaaaaa tcgttggcgt acgtagatca aaatccacca     120

<210> SEQ ID NO 127
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 127
cagtggcatt ggggctagag aacaactctt                                       30

<210> SEQ ID NO 128
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 128
ctctagcccc aatgccactg acacaatccc tttggtgaga tcatttgcta atagcacaca      60
aacattcttc aatgcatttg tggaggcgat ggataggatg ggaaacatta cacctcttac     120

<210> SEQ ID NO 129
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 129
ctctagcccc aatgccactg acacaatccc                                       30

<210> SEQ ID NO 130
<211> LENGTH: 72
<212> TYPE: DNA
<213> ORGANISM: Artificial Sequence
<220> FEATURE:
<223> OTHER INFORMATION: Primer for PCR multiplication

<400> SEQUENCE: 130
agagttggag ttcaccaccc tacaattcaa cctgatctgt ccttgagttc ctgtaagagg      60
tgtaatgttt cc                                                          72

<210> SEQ ID NO 131
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 131
agagttggag ttcaccaccc tacaattcaa                                       30

<210> SEQ ID NO 132
<211> LENGTH: 58
```

<212> TYPE: DNA
<213> ORGANISM: Artificial Sequence
<220> FEATURE:
<223> OTHER INFORMATION: Primer for PCR multiplication

<400> SEQUENCE: 132
agtcggatcc gtttatgcga atcagactcc gccttctaag gcgcggggtg gaggttcg    58

<210> SEQ ID NO 133
<211> LENGTH: 34
<212> TYPE: DNA
<213> ORGANISM: Artificial Sequence
<220> FEATURE:
<223> OTHER INFORMATION: Primer for PCR multiplication

<400> SEQUENCE: 133
aggcctcgag agagttggag ttcaccaccc taca    34

<210> SEQ ID NO 134
<211> LENGTH: 1695
<212> TYPE: DNA
<213> ORGANISM: Artificial Sequence
<220> FEATURE:
<223> OTHER INFORMATION: GroEL coding artificial sense-sequence

<400> SEQUENCE: 134
gtttatgcga atcagactcc gccttctaag gcgcggggtg gaggttcgat ggcagctaaa    60
gacgtaaaat tcggtaacga cgctcgtgtg aaaatgctgc gcggcgtaaa cgtactggca   120
gatgcagtga aagttaccct cggtccaaaa ggccgtaacg tagttctgga taaatctttc   180
ggtgcaccga ccatcaccaa agatggtgtt tccgttgctc gtgaaatcga actggaagac   240
aagttcgaaa atatgggtgc gcagatggtg aaagaagttg cctctaaagc aaacgacgct   300
gcaggcgacg gtaccaccac tgcaaccgta ctggctcagg ctatcatcac tgaaggtctg   360 aaaagctgttg ctgcgggcat gaacccgatg gacctgaaac gtggtatcga caaagcggtt   420
accgctgcag ttgaagaact gaaagcgctg tccgtaccat gctctgactc taaagcgatt   480
gctcaggttg gtaccatctc cgctaactcc gacgaaaccg taggtaaact gatcgctgaa   540
gcgatggaca agtcggtaa agaaggcgtt atcaccgttg aagacggtac cggtctgcag   600
gacgaactgg acgtggttga aggtatgcag ttcgaccgtg gctacctgtc tccttacttc   660
atcaacaagc cggaaactgg cgcagtagaa ctggaaagcc cgttcatcct gctggctgac   720
aagaaaatct ccaacatccg cgaaatgctg ccggttctgg aagctgttgc caaagcaggc   780
aaaccgctgc ttatcatcgc tgaagatgta gaaggcgaag cgctggcaac tgctgttgtt   840
aacaccattc gtggcatcgt gaaagtcgct gcggttaaag caccgggctt cggcgatcgt   900
cgtaaagcta tgctgcagga tatcgcaacc ctgactggcg gtaccgtgat ctctgaagag   960
atcggtatgg agctggaaaa agcaaccctg gaagacctgg tcaggctaa acgtgttgtg  1020 atcaacaaag acaccaccac tatcatcgat ggcgtgggtg aagaagctgc aatccagggc  1080
cgtgttgctc agatccgtca gcagattgaa gaagcaactt ctgactacga ccgtgaaaaa  1140
ctgcaggaac gcgtagcgaa actggcaggc ggcgttgcag ttatcaaagt gggtgctgct  1200
accgaagttg aaatgaaaga gaaaaagca cgcgttgaag atgccctgca cgcgacccgt  1260
gctgcggtag aagaaggcgt ggttgctggt ggtggtgttg cgctgatccg cgtagcgtct  1320
aaactggctg acctgcgtgg tcagaacgaa gaccagaacg tgggtatcaa agttgcactg  1380
cgtgcaatgg aagctccgct gcgtcagatc gtattgaact gcggcgaaga accgtctgtt  1440

```
gttgctaaca ccgttaaagg cggcgacggc aactacggtt acaacgcagc aaccgaagaa    1500
tacggcaaca tgatcgacat gggtatcctg gacccaacca aagtaactcg ttctgctctg    1560
cagtacgcag cttctgtggc tggcctgatg atcaccaccg aatgcatggt taccgacctg    1620
ccgaaaaacg atgcagctga cttaggcgct gctggcggta tgggcggcat gggtggcatg    1680
ggcggcatga tgtaa                                                     1695
```

<210> SEQ ID NO 135
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 135

```
gtttatgcga atcagactcc gccttctaag gcgcggggtg gaggttcgat ggcagctaaa     60
gacgtaaaat tcggtaacga cgctcgtgtg aaaatgctgc gcggcgtaaa cgtactggca    120
```

<210> SEQ ID NO 136
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 136

```
gtttatgcga atcagactcc gccttctaag                                      30
```

<210> SEQ ID NO 137
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 137

```
gagcaacgga aacaccatct ttggtgatgg tcggtgcacc gaaagattta tccagaacta     60
cgttacggcc ttttggaccg agggtaactt tcactgcatc tgccagtacg tttacgccgc    120
```

<210> SEQ ID NO 138
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 138

```
gagcaacgga aacaccatct ttggtgatgg                                      30
```

<210> SEQ ID NO 139
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 139

```
agatggtgtt tccgttgctc gtgaaatcga actggaagac aagttcgaaa atatgggtgc     60
gcagatggtg aaagaagttg cctctaaagc aaacgacgct gcaggcgacg gtaccaccac    120
```

<210> SEQ ID NO 140
<211> LENGTH: 30

-continued

<212> TYPE: DNA
<213> ORGANISM: Artificial Sequence
<220> FEATURE:
<223> OTHER INFORMATION: Primer for PCR multiplication

<400> SEQUENCE: 140
agatggtgtt tccgttgctc gtgaaatcga                                30

<210> SEQ ID NO 141
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 141
aaccgctttg tcgataccac gtttcaggtc catcgggttc atgcccgcag caacagcttt    60
cagaccttca gtgatgatag cctgagccag tacggttgca gtggtggtac cgtcgcctgc   120

<210> SEQ ID NO 142
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 142
aaccgctttg tcgataccac gtttcaggtc                                30

<210> SEQ ID NO 143
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 143
gtggtatcga caaagcggtt accgctgcag ttgaagaact gaaagcgctg tccgtaccat    60
gctctgactc taaagcgatt gctcaggttg gtaccatctc cgctaactcc gacgaaaccg   120

<210> SEQ ID NO 144
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 144
gtggtatcga caaagcggtt accgctgcag                                30

<210> SEQ ID NO 145
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 145
tcaaccacgt ccagttcgtc ctgcagaccg gtaccgtctt caacggtgat aacgccttct    60
ttaccgactt tgtccatcgc ttcagcgatc agtttaccta cggtttcgtc ggagttagcg   120

<210> SEQ ID NO 146
<211> LENGTH: 30
<212> TYPE: DNA

<213> ORGANISM: Artificial Sequence
<220> FEATURE:
<223> OTHER INFORMATION: Primer for PCR multiplication

<400> SEQUENCE: 146
tcaaccacgt ccagttcgtc ctgcagaccg                                      30

<210> SEQ ID NO 147
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 147
gacgaactgg acgtggttga aggtatgcag ttcgaccgtg gctacctgtc tccttacttc     60
atcaacaagc cggaaactgg cgcagtagaa ctggaaagcc cgttcatcct gctggctgac    120

<210> SEQ ID NO 148
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 148
gacgaactgg acgtggttga aggtatgcag                                      30

<210> SEQ ID NO 149
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 149
cttcgccttc tacatcttca gcgatgataa gcagcggttt gcctgctttg caacagctt      60 ccagaaccgg cagcatttcg cggatgttgg agattttctt gtcagccagc aggatgaacg    120

<210> SEQ ID NO 150
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 150
cttcgccttc tacatcttca gcgatgataa                                      30

<210> SEQ ID NO 151
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 151
tgaagatgta aaggcgaag cgctggcaac tgctgttgtt aacaccattc gtggcatcgt      60
gaaagtcgct gcggttaaag caccgggctt cggcgatcgt cgtaaagcta tgctgcagga    120

<210> SEQ ID NO 152
<211> LENGTH: 30
<212> TYPE: DNA
<213> ORGANISM: Artificial Sequence

```
<220> FEATURE:
<223> OTHER INFORMATION: Primer for PCR multiplication

<400> SEQUENCE: 152
tgaagatgta gaaggcgaag cgctggcaac                                          30

<210> SEQ ID NO 153
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 153
cacaacacgt ttagcctgac ccaggtcttc cagggttgct ttttccagct ccataccgat         60
ctcttcagag atcacggtac cgccagtcag ggttgcgata tcctgcagca tagctttacg        120

<210> SEQ ID NO 154
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 154
cacaacacgt ttagcctgac ccaggtcttc                                          30

<210> SEQ ID NO 155
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 155
gtcaggctaa acgtgttgtg atcaacaaag acaccaccac tatcatcgat ggcgtgggtg         60
aagaagctgc aatccagggc cgtgttgctc agatccgtca gcagattgaa gaagcaactt        120

<210> SEQ ID NO 156
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 156
gtcaggctaa acgtgttgtg atcaacaaag                                          30

<210> SEQ ID NO 157
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 157
tctttcattt caacttcggt agcagcaccc actttgataa ctgcaacgcc gcctgccagt         60
ttcgctacgc gttcctgcag ttttcacgg tcgtagtcag aagttgcttc ttcaatctgc        120

<210> SEQ ID NO 158
<211> LENGTH: 30
<212> TYPE: DNA
<213> ORGANISM: Artificial Sequence
<220> FEATURE:
```

<223> OTHER INFORMATION: Primer for PCR multiplication

<400> SEQUENCE: 158
tctttcattt caacttcggt agcagcaccc                                             30

<210> SEQ ID NO 159
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 159
accgaagttg aaatgaaaga gaaaaaagca cgcgttgaag atgccctgca cgcgacccgt            60
gctgcggtag aagaaggcgt ggttgctggt ggtggtgttg cgctgatccg cgtagcgtct          120

<210> SEQ ID NO 160
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 160
accgaagttg aaatgaaaga gaaaaaagca                                             30

<210> SEQ ID NO 161
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 161
agttcaatac gatctgacgc agcggagctt ccattgcacg cagtgcaact ttgataccca            60
cgttctggtc ttcgttctga ccacgcaggt cagccagttt agacgctacg cggatcagcg          120

<210> SEQ ID NO 162
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 162
agttcaatac gatctgacgc agcggagctt                                             30

<210> SEQ ID NO 163
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 163
gcgtcagatc gtattgaact gcggcgaaga accgtctgtt gttgctaaca ccgttaaagg            60
cggcgacggc aactacggtt acaacgcagc aaccgaagaa tacggcaaca tgatcgacat          120

<210> SEQ ID NO 164
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 164
gcgtcagatc gtattgaact gcggcgaaga                                    30

<210> SEQ ID NO 165
<211> LENGTH: 120
<212> TYPE: DNA
<213> ORGANISM: Artificial Sequence
<220> FEATURE:
<223> OTHER INFORMATION: Primer for PCR multiplication

<400> SEQUENCE: 165
caggtcggta accatgcatt cggtggtgat catcaggcca gccacagaag ctgcgtactg    60
cagagcagaa cgagttactt tggttgggtc caggataccc atgtcgatca tgttgccgta   120

<210> SEQ ID NO 166
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 166
caggtcggta accatgcatt cggtggtgat                                    30

<210> SEQ ID NO 167
<211> LENGTH: 95
<212> TYPE: DNA
<213> ORGANISM: Artificial Sequence
<220> FEATURE:
<223> OTHER INFORMATION: Primer for PCR multiplication

<400> SEQUENCE: 167
ttacatcatg ccgcccatgc cacccatgcc gcccataccg ccagcagcgc ctaagtcagc    60
tgcatcgttt ttcggcaggt cggtaaccat gcatt                              95

<210> SEQ ID NO 168
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 168
aggcctcgag ttacatcatg ccgcccatgc                                    30

<210> SEQ ID NO 169
<211> LENGTH: 33
<212> TYPE: DNA
<213> ORGANISM: Artificial Sequence
<220> FEATURE:
<223> OTHER INFORMATION: Primer for PCR multiplication

<400> SEQUENCE: 169
ttacatcatg ccgcccatgc cacccatgcc gcc                                33

<210> SEQ ID NO 170
<211> LENGTH: 8
<212> TYPE: PRT
<213> ORGANISM: Artificial Sequence
<220> FEATURE:
<223> OTHER INFORMATION: anodisk membrane-binding peptide

<400> SEQUENCE: 170

Tyr Ala Gln Thr Pro Pro Ser Arg
 1               5

<210> SEQ ID NO 171
<211> LENGTH: 12
<212> TYPE: PRT
<213> ORGANISM: Artificial Sequence
<220> FEATURE:
<223> OTHER INFORMATION: anodisk membrane-binding peptide

<400> SEQUENCE: 171

Leu Tyr Ala Gln Gln Thr Pro Pro Ser Arg Ser Arg
 1               5                  10

<210> SEQ ID NO 172
<211> LENGTH: 16
<212> TYPE: PRT
<213> ORGANISM: Artificial Sequence
<220> FEATURE:
<223> OTHER INFORMATION: anodisk membrane-binding peptide

<400> SEQUENCE: 172

Val Tyr Ala Asn Gln Thr Pro Pro Ser Arg Ala Arg Ala Lys Ala Arg
 1               5                  10                  15

<210> SEQ ID NO 173
<211> LENGTH: 20
<212> TYPE: PRT
<213> ORGANISM: Artificial Sequence
<220> FEATURE:
<223> OTHER INFORMATION: anodisk membrane-binding peptide

<400> SEQUENCE: 173

Val Tyr Ala Asn Gln Thr Pro Pro Ser Lys Ala Arg Tyr Ala Gln
 1               5                  10                  15

Thr Pro Pro Ser Arg
            20

<210> SEQ ID NO 174
<211> LENGTH: 46
<212> TYPE: DNA
<213> ORGANISM: Artificial Sequence
<220> FEATURE:
<223> OTHER INFORMATION: Coding chain for peptide of SEQ ID:170

<400> SEQUENCE: 174
gatcctatgc gcagactccg ccttctcggg gtggaggttc ggagct                   46

<210> SEQ ID NO 175
<211> LENGTH: 38
<212> TYPE: DNA
<213> ORGANISM: Artificial Sequence
<220> FEATURE:
<223> OTHER INFORMATION: Complimentary chain for ssDNA of SEQ ID:170

<400> SEQUENCE: 175
ccgaacctcc accccgagaa ggcggagtct gcgcatag                            38

<210> SEQ ID NO 176
<211> LENGTH: 58
<212> TYPE: DNA
<213> ORGANISM: Artificial Sequence
<220> FEATURE:
<223> OTHER INFORMATION: Coding chain for peptide of SEQ ID:171

<400> SEQUENCE: 176

```
gatccctcta tgcgcaacag actccgcctt ctcggtctcg gggtggaggt tcggagct      58
```

<210> SEQ ID NO 177
<211> LENGTH: 50
<212> TYPE: DNA
<213> ORGANISM: Artificial Sequence
<220> FEATURE:
<223> OTHER INFORMATION: Complimentary chain for ssDNA of SEQ ID:171

<400> SEQUENCE: 177

```
ccgaacctcc accccgagac cgagaaggcg gagtctgttg cgcataagag               50
```

<210> SEQ ID NO 178
<211> LENGTH: 70
<212> TYPE: DNA
<213> ORGANISM: Artificial Sequence
<220> FEATURE:
<223> OTHER INFORMATION: Coding chain for peptide of SEQ ID:1

<400> SEQUENCE: 178

```
gatccgttta tgcgaatcag actccgcctt ctcgcgcacg cgcaaaggcg cggggtggag    60
gttcggagct                                                          70
```

<210> SEQ ID NO 179
<211> LENGTH: 62
<212> TYPE: DNA
<213> ORGANISM: Artificial Sequence
<220> FEATURE:
<223> OTHER INFORMATION: Complimentary chain for ssDNA of SEQ ID:1

<400> SEQUENCE: 179

```
ccgaacctcc accccgcgcc tttgcgcgtg cgcgagaagg cggagtctga ttcgcataaa    60
cg                                                                  62
```

<210> SEQ ID NO 180
<211> LENGTH: 82
<212> TYPE: DNA
<213> ORGANISM: Artificial Sequence
<220> FEATURE:
<223> OTHER INFORMATION: Coding chain for peptide of SEQ ID:1

<400> SEQUENCE: 180

```
gatccgttta tgcgaatcag actccgcctt ctaaggcgcg gtatgcgcag actccgcctt    60
ctcggggtgg aggttcggag ct                                            82
```

<210> SEQ ID NO 181
<211> LENGTH: 74
<212> TYPE: DNA
<213> ORGANISM: Artificial Sequence
<220> FEATURE:
<223> OTHER INFORMATION: Complimentary chain for ssDNA of SEQ ID:1

<400> SEQUENCE: 181

```
ccgaacctcc accccgagaa ggcggagtct gcgcataccg cgccttagaa ggcggagtct    60
gattcgcata aacg                                                     74
```